(12) United States Patent
Stadler et al.

(10) Patent No.: US 10,154,794 B2
(45) Date of Patent: Dec. 18, 2018

(54) IMPLANTABLE CARDIOVERTER-DEFIBRILLATOR (ICD) TACHYARRHYTHMIA DETECTION MODIFICATIONS RESPONSIVE TO DETECTED PACING

(71) Applicant: Medtronic, Inc., Minneapolis, MN (US)

(72) Inventors: Robert W. Stadler, Shoreview, MN (US); Xusheng Zhang, Shoreview, MN (US); Vinod Sharma, Maple Grove, MN (US); James D. Reinke, Maple Grove, MN (US); Barbara J. Schmid, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 683 days.

(21) Appl. No.: 14/687,010

(22) Filed: Apr. 15, 2015

(65) Prior Publication Data
US 2015/0305641 A1 Oct. 29, 2015

Related U.S. Application Data

(60) Provisional application No. 61/984,214, filed on Apr. 25, 2014.

(51) Int. Cl.
*A61B 5/04* (2006.01)
*A61B 5/0464* (2006.01)
(Continued)

(52) U.S. Cl.
CPC ........ *A61B 5/0464* (2013.01); *A61B 5/04017* (2013.01); *A61B 5/686* (2013.01);
(Continued)

(58) Field of Classification Search
CPC ... A61B 5/0464; A61B 5/686; A61B 5/04017; A61N 1/37264; A61N 1/3621;
(Continued)

(56) References Cited

U.S. PATENT DOCUMENTS 4,226,245 A 10/1980 Bennett, Jr.
4,328,807 A 5/1982 Jirak et al.
(Continued)

FOREIGN PATENT DOCUMENTS

CN 103736206 A 4/2014
EP 09239630 6/1999

OTHER PUBLICATIONS

Zhang, "Method and Apparatus for Discriminating Tachycardia Events in a Medical Device Using Two Sensing Vectors", U.S. Appl. No. 14/250,040, filed Apr. 10, 2014, 52 pages.
(Continued)

*Primary Examiner* — Mallika D Fairchild

(57) ABSTRACT

An implantable medical device comprises a sensing module configured to obtain electrical signals from one or more electrodes and a control module configured to process the electrical signals from the sensing module in accordance with a tachyarrhythmia detection algorithm to monitor for a tachyarrhythmia. The control module detects initiation of a pacing train delivered by a second implantable medical device, determines a type of the detected pacing train, and modifies the tachyarrhythmia detection algorithm based on the type of the detected pacing train.

38 Claims, 22 Drawing Sheets

(51) Int. Cl.
*A61B 5/00* (2006.01)
*A61N 1/372* (2006.01)
*A61N 1/375* (2006.01)
*A61N 1/39* (2006.01)
*A61N 1/362* (2006.01)

(52) U.S. Cl.
CPC .......... *A61N 1/3621* (2013.01); *A61N 1/3756* (2013.01); *A61N 1/37264* (2013.01); *A61N 1/37288* (2013.01); *A61N 1/3962* (2013.01); *A61N 1/3987* (2013.01)

(58) Field of Classification Search
CPC .. A61N 1/3756; A61N 1/3962; A61N 1/3987; A61N 1/37288
See application file for complete search history.

(56) References Cited

U.S. PATENT DOCUMENTS

| | | |
|---|---|---|
| 4,539,999 A | 9/1985 | Mans |
| 4,787,389 A | 11/1988 | Tarjan |
| 4,832,041 A | 5/1989 | Wang et al. |
| 5,010,888 A | 4/1991 | Hossein et al. |
| 5,127,401 A | 7/1992 | Grevious et al. |
| 5,331,966 A | 7/1994 | Bennett et al. |
| 5,448,997 A | 9/1995 | Kruse et al. |
| 5,660,184 A | 8/1997 | Donehoo et al. |
| 5,682,902 A | 11/1997 | Herleikson |
| 5,772,692 A | 6/1998 | Armstrong |
| 5,776,167 A | 7/1998 | Levine et al. |
| 5,913,828 A | 6/1999 | Russell |
| 5,951,483 A | 9/1999 | Joo |
| 6,721,597 B1 | 4/2004 | Bardy et al. |
| 6,754,528 B2 | 6/2004 | Bardy et al. |
| 6,819,953 B2 | 11/2004 | Yonce et al. |
| 6,834,204 B2 | 12/2004 | Ostroff et al. |
| 6,856,835 B2 | 2/2005 | Bardy et al. |
| 6,937,907 B2 | 8/2005 | Bardy et al. |
| 6,952,610 B2 | 10/2005 | Ostroff et al. |
| 6,988,003 B2 | 1/2006 | Bardy et al. |
| 7,027,858 B2 | 4/2006 | Cao et al. |
| 7,043,299 B2 | 5/2006 | Erlinger et al. |
| 7,065,410 B2 | 6/2006 | Bardy et al. |
| 7,069,080 B2 | 6/2006 | Bardy et al. |
| 7,076,294 B2 | 7/2006 | Bardy et al. |
| 7,076,296 B2 | 7/2006 | Rissmann et al. |
| 7,090,682 B2 | 8/2006 | Sanders et al. |
| 7,092,754 B2 | 8/2006 | Bardy et al. |
| 7,146,212 B2 | 12/2006 | Bardy et al. |
| 7,149,575 B2 | 12/2006 | Ostroff et al. |
| 7,181,274 B2 | 2/2007 | Rissmann et al. |
| 7,194,302 B2 | 3/2007 | Bardy et al. |
| 7,239,925 B2 | 7/2007 | Bardy et al. |
| 7,248,921 B2 | 7/2007 | Palreddy et al. |
| 7,274,962 B2 | 9/2007 | Bardy et al. |
| 7,277,754 B2 | 10/2007 | McCabe et al. |
| 7,299,092 B2 | 11/2007 | Bardy et al. |
| 7,299,097 B2 | 11/2007 | Bardy et al. |
| 7,302,300 B2 | 11/2007 | Bardy et al. |
| 7,330,757 B2 | 2/2008 | Ostroff et al. |
| 7,349,736 B2 | 3/2008 | Ostroff et al. |
| 7,376,458 B2 | 5/2008 | Palreddy et al. |
| 7,379,772 B2 | 5/2008 | Bardy et al. |
| 7,392,085 B2 | 6/2008 | Warren et al. |
| 7,406,350 B2 | 7/2008 | Erlinger et al. |
| 7,444,182 B2 | 10/2008 | Ostroff et al. |
| 7,463,924 B2 | 12/2008 | Bardy et al. |
| 7,471,977 B2 | 12/2008 | Zinser, Jr. et al. |
| 7,477,935 B2 | 1/2009 | Palreddy et al. |
| 7,502,645 B2 | 3/2009 | Ostroff et al. |
| 7,536,222 B2 | 5/2009 | Bardy et al. |
| 7,623,909 B2 | 11/2009 | Sanghera et al. |
| 7,623,913 B2 | 11/2009 | Phillips |
| 7,627,367 B2 | 12/2009 | Warren et al. |
| 7,627,375 B2 | 12/2009 | Bardy et al. |
| 7,655,014 B2 | 2/2010 | Ko et al. |
| 7,657,311 B2 | 2/2010 | Bardy et al. |
| 7,657,322 B2 | 2/2010 | Bardy et al. |
| 7,720,534 B2 | 5/2010 | Bardy et al. |
| 7,720,536 B2 | 5/2010 | Rissman et al. |
| 7,751,885 B2 | 7/2010 | Bardy et al. |
| 7,761,150 B2 | 7/2010 | Ghanem et al. |
| 7,774,058 B2 | 8/2010 | Ostroff et al. |
| 7,774,059 B2 | 8/2010 | Ostroff et al. |
| 7,783,340 B2 | 8/2010 | Sanghera et al. |
| 7,835,790 B2 | 11/2010 | Ostroff et al. |
| 7,894,894 B2 | 2/2011 | Stadler et al. |
| 7,953,489 B2 | 5/2011 | Warren et al. |
| 7,991,459 B2 | 8/2011 | Palreddy et al. |
| 7,991,467 B2 | 8/2011 | Markowitz et al. |
| 7,996,082 B2 | 8/2011 | Palreddy et al. |
| 7,996,087 B2 | 8/2011 | Cowan et al. |
| 8,014,851 B2 | 9/2011 | Ostroff et al. |
| 8,014,862 B2 | 9/2011 | Ostroff et al. |
| 8,027,720 B2 | 9/2011 | Bardy et al. |
| 8,050,754 B2 | 11/2011 | Ostroff et al. |
| 8,073,532 B2 | 12/2011 | Palreddy et al. |
| 8,090,438 B2 | 1/2012 | Bardy et al. |
| 8,116,867 B2 | 2/2012 | Ostroff |
| 8,145,305 B2 | 3/2012 | Ostroff et al. |
| 8,157,813 B2 | 4/2012 | Ko et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,185,198 B2 | 5/2012 | Palreddy et al. |
| 8,200,341 B2 | 6/2012 | Sanghera et al. |
| 8,229,563 B2 | 7/2012 | Warren et al. |
| 8,244,349 B2 | 8/2012 | Sanghera et al. |
| 8,249,702 B2 | 8/2012 | Warren et al. |
| 8,265,737 B2 | 9/2012 | Warren et al. |
| 8,265,749 B2 | 9/2012 | Allavatam et al. |
| 8,285,375 B2 | 10/2012 | Bardy et al. |
| 8,346,357 B2 | 1/2013 | Palreddy et al. |
| 8,364,251 B2 | 1/2013 | Phillips |
| 8,386,037 B2 | 2/2013 | Ostroff et al. |
| 8,391,990 B2 | 3/2013 | Smith et al. |
| 8,412,320 B2 | 4/2013 | Ostroff et al. |
| 8,437,838 B2 | 5/2013 | Warren et al. |
| 8,447,398 B2 | 5/2013 | Bardy et al. |
| 8,457,737 B2 | 6/2013 | Bardy et al. |
| 8,457,742 B2 | 6/2013 | Jacobson |
| 8,483,841 B2 | 7/2013 | Sanghera et al. |
| 8,483,843 B2 | 7/2013 | Sanghera et al. |
| 8,494,630 B2 | 7/2013 | Palreddy et al. |
| 8,548,573 B2 | 10/2013 | Keefe |
| 8,565,878 B2 | 10/2013 | Allavatam et al. |
| 8,577,454 B2 | 11/2013 | Bardy et al. |
| 8,588,895 B2 | 11/2013 | Sanghera et al. |
| 8,588,896 B2 | 11/2013 | Allavatam et al. |
| 8,600,489 B2 | 12/2013 | Warren et al. |
| 8,626,280 B2 | 1/2014 | Allavatam et al. |
| 8,626,285 B2 | 1/2014 | Palreddy et al. |
| 8,644,926 B2 | 2/2014 | Ostroff et al. |
| 8,660,668 B2 | 2/2014 | Bardy et al. |
| 8,666,489 B2 | 3/2014 | Ostroff |
| 8,670,826 B2 | 3/2014 | Warren et al. |
| 8,700,152 B2 | 4/2014 | Palreddy et al. |
| 8,712,523 B2 | 4/2014 | Sanghera et al. |
| 8,718,760 B2 | 5/2014 | Bardy et al. |
| 8,718,793 B2 | 5/2014 | O'Connor |
| 8,744,555 B2 | 6/2014 | Allavatam et al. |
| 8,744,572 B1 | 6/2014 | Greenhut et al. |
| 8,750,989 B2 | 6/2014 | Bardy et al. |
| 8,781,567 B2 | 7/2014 | Phillips |
| 8,781,602 B2 | 7/2014 | Sanghera et al. |
| 8,788,023 B2 | 7/2014 | Sanghera et al. |
| 8,801,729 B2 | 8/2014 | Ko et al. |
| 8,825,157 B2 | 9/2014 | Warren et al. |
| 8,831,711 B2 | 9/2014 | Freer et al. |
| 8,831,720 B2 | 9/2014 | Bardy et al. |
| 8,838,234 B2 | 9/2014 | Ostroff et al. |
| 8,855,780 B2 | 10/2014 | Hansen et al. |
| 8,880,161 B2 | 11/2014 | Warren et al. |

(56) References Cited

U.S. PATENT DOCUMENTS

| | | |
|---|---|---|
| 2002/0035379 A1 | 3/2002 | Bardy et al. |
| 2002/0095184 A1 | 7/2002 | Bardy et al. |
| 2002/0107544 A1 | 8/2002 | Ostroff et al. |
| 2004/0230128 A1 | 11/2004 | Brockway et al. |
| 2005/0049643 A9 | 3/2005 | Rissmann et al. |
| 2005/0096703 A1 | 5/2005 | Sanders |
| 2005/0107835 A1 | 5/2005 | Bardy et al. |
| 2006/0173498 A1 | 8/2006 | Banville et al. |
| 2006/0206151 A1 | 9/2006 | Lu |
| 2006/0241700 A1 | 10/2006 | Ghanem et al. |
| 2007/0232944 A1 | 2/2007 | Inagaki |
| 2007/0055314 A1 | 3/2007 | Bardy et al. |
| 2007/0088394 A1 | 4/2007 | Jacobson |
| 2007/0135851 A1 | 6/2007 | Gilkerson et al. |
| 2007/0232948 A1 | 10/2007 | Stadler et al. |
| 2007/0233196 A1 | 10/2007 | Stadler et al. |
| 2007/0233198 A1 | 10/2007 | Ghanem et al. |
| 2007/0239044 A1 | 10/2007 | Ghanem et al. |
| 2007/0239045 A1 | 10/2007 | Ghanem et al. |
| 2007/0239046 A1 | 10/2007 | Ghanem et al. |
| 2007/0239047 A1 | 10/2007 | Ghanem et al. |
| 2007/0239048 A1 | 10/2007 | Ghanem et al. |
| 2007/0239049 A1 | 10/2007 | Ghanem et al. |
| 2007/0239050 A1 | 10/2007 | Ghanem et al. |
| 2007/0239051 A1 | 10/2007 | Ghanem et al. |
| 2007/0270704 A1 | 11/2007 | Ghanem et al. |
| 2007/0276452 A1 | 11/2007 | Sanghera et al. |
| 2008/0103535 A1 | 5/2008 | Ostroff et al. |
| 2008/0132965 A1 | 6/2008 | Ostroff et al. |
| 2008/0272216 A1 | 11/2008 | Kraft et al. |
| 2008/0275517 A1 | 11/2008 | Ghanem et al. |
| 2008/0275518 A1 | 11/2008 | Ghanem et al. |
| 2008/0275519 A1 | 11/2008 | Ghanem et al. |
| 2010/0030093 A1 | 2/2010 | Zhang et al. |
| 2010/0069986 A1 | 3/2010 | Stahl et al. |
| 2010/0114208 A1 | 5/2010 | Donofrio et al. |
| 2010/0152799 A1 | 6/2010 | Sanghera et al. |
| 2010/0331904 A1 | 12/2010 | Warren et al. |
| 2011/0137360 A1 | 6/2011 | Ternes et al. |
| 2011/0307024 A1 | 12/2011 | Ostroff et al. |
| 2012/0029335 A1 | 2/2012 | Sudam et al. |
| 2012/0053477 A1 | 3/2012 | Zhang et al. |
| 2012/0095520 A1 | 4/2012 | Zhang et al. |
| 2012/0197147 A1 | 8/2012 | Allavatam et al. |
| 2012/0271185 A1 | 10/2012 | Sanghera et al. |
| 2012/0316612 A1 | 12/2012 | Warren et al. |
| 2012/0316613 A1 | 12/2012 | Keefe et al. |
| 2013/0053908 A1 | 2/2013 | Smith et al. |
| 2013/0103109 A1 | 4/2013 | Jacobson et al. |
| 2013/0138170 A1 | 5/2013 | Ternes et al. |
| 2013/0268013 A1 | 10/2013 | Sanghera et al. |
| 2014/0046204 A1 | 2/2014 | Allavatam et al. |
| 2014/0046206 A1 | 2/2014 | Sanghera et al. |
| 2014/0046394 A1 | 2/2014 | Allavatam et al. |
| 2014/0094868 A1 | 4/2014 | Allavatam et al. |
| 2014/0172032 A1 | 6/2014 | Palreddy et al. |
| 2014/0200592 A1 | 7/2014 | O'Connor |
| 2014/0214104 A1 | 7/2014 | Greenhut et al. |
| 2014/0221857 A1 | 8/2014 | Allavatam et al. |
| 2014/0222097 A1 | 8/2014 | Bardy et al. |
| 2014/0257120 A1 | 9/2014 | Warren et al. |
| 2014/0257421 A1 | 9/2014 | Sanghera et al. |
| 2014/0275917 A1 | 9/2014 | Allavatam et al. |
| 2014/0276155 A1 | 9/2014 | Zhang |
| 2014/0276158 A1 | 9/2014 | Zhang |
| 2014/0276159 A1 | 9/2014 | Zhang |
| 2014/0276160 A1 | 9/2014 | Zhang et al. |
| 2014/0296932 A1 | 10/2014 | Sanghera et al. |
| 2014/0324068 A1 | 10/2014 | Ko et al. |

OTHER PUBLICATIONS (PCT/US2015/026096 PCT Notification of Transmittal of the International Search Report and the Written Opinion of the International Searching Authority, dated Aug. 21, 2015, 9 pages.

IMPLANTABLE CARDIOVERTER-DEFIBRILLATOR (ICD) TACHYARRHYTHMIA DETECTION MODIFICATIONS RESPONSIVE TO DETECTED PACING

This application claims the benefit of U.S. Provisional Application No. 61/984,214, filed on Apr. 25, 2014, the content of which is incorporated herein by reference in its entirety.

TECHNICAL FIELD

This application relates to medical devices, and, more particularly, to implantable medical devices configured to detect and treat cardiac arrhythmias.

BACKGROUND

ICD systems may be used to deliver high energy cardioversion or defibrillation shocks to a patient's heart to terminate a detected tachyarrhythmia, such as an atrial or ventricular fibrillation. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by the ICD. Additionally, ICD systems may also deliver high energy cardioversion or defibrillation shocks to terminate certain types of ventricular tachycardia (VT).

ICD systems generally include an ICD that is coupled to one or more electrical leads placed within or attached to the heart. The electrical leads include one or more electrodes positioned in or on the heart by the leads and used for therapy and/or sensing functions. Cardioversion and defibrillation shocks (e.g., anti-tachyarrhythmia or high voltage shocks) are generally applied between a coil electrode carried by one of the leads and the ICD housing, which acts as an active can electrode.

In addition, or as an alternative to cardioversion and defibrillation shocks, the ICD system may provide pacing therapy to the heart. Conventional ICD systems provide the pacing therapy via the electrodes of the lead that are positioned near or against the cardiac tissue to provide sufficient transmission of electrical energy to the cardiac tissue in order to capture the heart. The pacing therapy may, for example, include cardiac pacing to suppress or convert tachyarrhythmias to sinus rhythm. Such pacing is often referred to as anti-tachycardia pacing or ATP. The ICD system may provide ATP in an attempt to terminate arrhythmias that would otherwise need to be treated by a cardioversion or defibrillation shock, which are uncomfortable for the patient. The ICD system may also provide anti-bradycardia pacing when the natural pacemaker and/or conduction system of the heart fails to provide synchronized atrial and ventricular contractions at rates and intervals sufficient to sustain healthy patient function.

SUMMARY

Subcutaneous ICD systems have also been developed that do not include leads that are within or attached to the heart. In the subcutaneous ICD system, the lead is instead placed subcutaneously above the ribcage and/or sternum. Such systems do not generally provide ATP because of the amount of energy required for such pacing pulses as well as the discomfort experienced by the subject in which the device is implanted. Systems have been proposed in which a leadless pacing device (LPD) is implanted along with the subcutaneous ICD to provide the desired ATP.

In situations in which a subcutaneous ICD operates in conjunction with a co-implanted LPD (or other artificial pacemaker) it may be important that the subcutaneous ICD knows when pacing, such as ATP, is being or has been delivered by the LPD. Based on the knowledge that pacing is being or has been delivered, the subcutaneous ICD may make some sort of adjustment to account for the pacing. For example, the subcutaneous ICD may blank the sensing channel to remove the pacing pulse from the sensed electrical signal, adjust a tachyarrhythmia detection algorithm, make another adjustment, or a combination thereof. This disclosure describes the implementation of a pace detector and techniques for adjusting operation based on the detection of the pacing pulses.

In one example, this disclosure is directed to a method that comprises detecting, with an extravascular implantable medical device (IMD), initiation of a pacing train delivered by a second implantable medical device, determining a type of the detected pacing train, and modifying a tachyarrhythmia detection algorithm based on the type of the detected pacing train.

In another example, this disclosure is directed to an implantable medical device, such as a subcutaneous ICD, that comprises a sensing module configured to obtain electrical signals from one or more electrodes and a control module configured to process the electrical signals from the sensing module in accordance with a tachyarrhythmia detection algorithm to monitor for a tachyarrhythmia, detect initiation of a pacing train delivered by a second implantable medical device, determine a type of the detected pacing train, and modify the tachyarrhythmia detection algorithm based on the type of the detected pacing train.

In further example, this disclosure is directed to a system comprising an implantable pacemaker device and an extravascular implantable cardioverter-defibrillator (ICD) system, such as a subcutaneous ICD system. The extravascular ICD system includes an ICD device electrically connected to at least one lead having one or more electrodes. The ICD device includes a sensing module configured to obtain electrical signals from the one or more electrodes and a control module configured to process the electrical signals from the sensing module in accordance with a tachyarrhythmia detection algorithm to monitor for a tachyarrhythmia, wherein the control module is further configured to detect initiation of a pacing train delivered by the implantable medical device, determine a type of the detected pacing train, and modify the tachyarrhythmia detection algorithm based on the type of the detected pacing train.

The details of one or more examples are set forth in the accompanying drawings and the description below. Other features, objects, and advantages will be apparent from the description and drawings, and from the claims.

DETAILED DESCRIPTION

Figure 1:
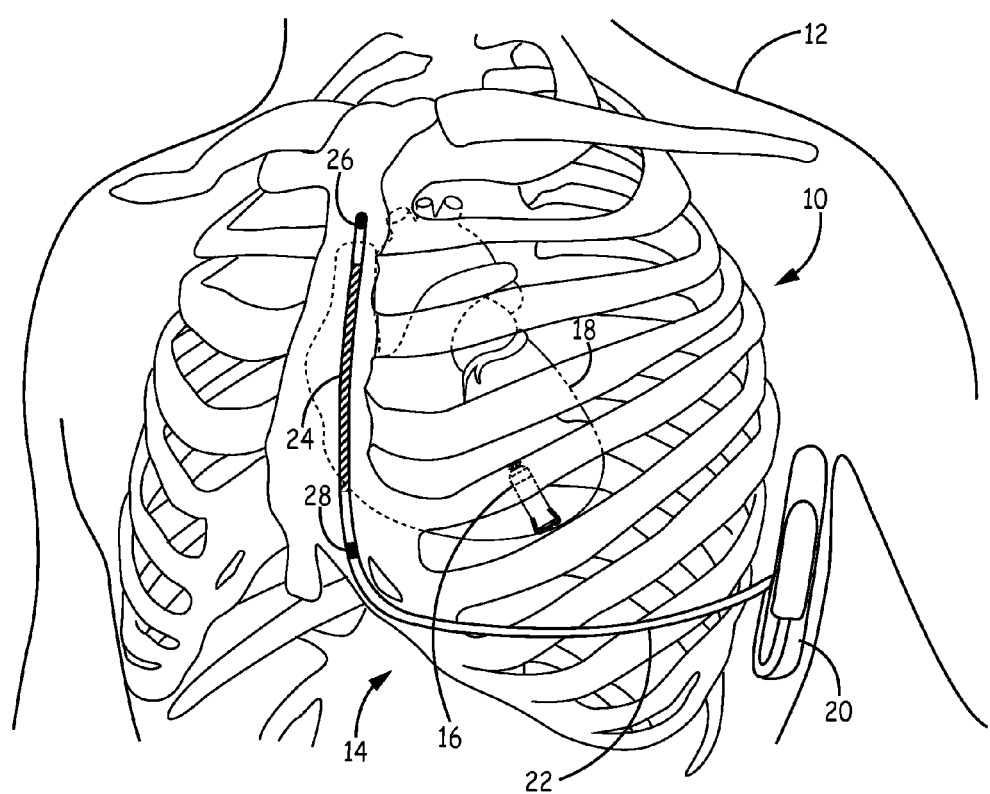
FIG. 1 is a conceptual drawing illustrating an example cardiac system having coexistent ICD system and pacing system implanted within a patient.

FIG. 1 is a conceptual drawing illustrating an example cardiac system 10 implanted within a patient 12. Cardiac system 10 includes a subcutaneous ICD system 14 implanted above the ribcage and sternum and a leadless cardiac pacing device 16 implanted within a heart 18 of patient 12. As will be described in further detail herein, subcutaneous ICD system 14 is configured to detect pacing therapy delivered by pacing device 16 by analyzing sensed electrical signals and, in response to detecting the pacing therapy, modify sensing and/or tachyarrhythmia detection.

Subcutaneous ICD system 14 includes an implantable cardiac defibrillator (ICD) 20 connected to at least one implantable cardiac defibrillation lead 22. ICD 20 of FIG. 1 is implanted subcutaneously on the left side of patient 12 under the skin but above the ribcage. Defibrillation lead 22 extends subcutaneously under the skin but above the ribcage from ICD 20 toward a center of the torso of patient 12, bends or turns near the center of the torso, and extends subcutaneously superior under the skin but above the ribcage and/or sternum. Defibrillation lead 22 may be offset laterally to the left or the right of the sternum or located over the sternum. Defibrillation lead 22 may extend substantially parallel to the sternum or be angled lateral from the sternum at either the proximal or distal end.

Defibrillation lead 22 includes an insulative lead body having a proximal end that includes a connector configured to be connected to ICD 20 and a distal portion that includes one or more electrodes. Defibrillation lead 22 also includes one or more conductors that form an electrically conductive path within the lead body and interconnect the electrical connector and respective ones of the electrodes.

Defibrillation lead 22 includes a defibrillation electrode 24 toward the distal portion of defibrillation lead 22, e.g., toward the portion of defibrillation lead 22 extending along the sternum. Defibrillation lead 22 is placed along sternum such that a therapy vector between defibrillation electrode 24 and a housing electrode formed by or on ICD 20 (or other second electrode of the therapy vector) is substantially across a ventricle of heart 18. The therapy vector may, in one example, be viewed as a line that extends from a point on defibrillation electrode 24 (e.g., a center of the defibrillation electrode 24) to a point on the housing electrode of ICD 20. Defibrillation electrode 24 may, in one example, be an elongated coil electrode.

Defibrillation lead 22 may also include one or more sensing electrodes, such as sensing electrodes 26 and 28, located along the distal portion of defibrillation lead 22. In the example illustrated in FIG. 1, sensing electrodes 26 and 28 are separated from one another by defibrillation electrode 24. In other examples, however, sensing electrodes 26 and 28 may be both distal of defibrillation electrode 24 or both proximal of defibrillation electrode 24. In other examples, lead 22 may include more or fewer electrodes.

ICD system 14 may sense electrical signals via one or more sensing vectors that include combinations of electrodes 26 and 28 and the housing electrode of ICD 20. For example, ICD 20 may obtain electrical signals sensed using a sensing vector between electrodes 26 and 28, obtain electrical signals sensed using a sensing vector between electrode 26 and the conductive housing electrode of ICD 20, obtain electrical signals sensed using a sensing vector between electrode 28 and the conductive housing electrode of ICD 20, or a combination thereof. In some instances, ICD 20 may even sense cardiac electrical signals using a sensing vector that includes defibrillation electrode 24 and one of electrodes 26 and 28 or the housing electrode of ICD 20.

The sensed electrical intrinsic signals may include electrical signals generated by cardiac muscle and indicative of depolarizations and repolarizations of heart 18 at various times during the cardiac cycle. Additionally, the sensed electrical signals may also include electrical signals, e.g., pacing pulses, generated and delivered to heart 18 by pacing device 16. ICD 20 analyzes the electrical signals sensed by the one or more sensing vectors to detect tachyarrhythmia, such as ventricular tachycardia or ventricular fibrillation. In response to detecting the tachycardia, ICD 20 may begin to charge a storage element, such as a bank of one or more capacitors, and, when charged, deliver one or more shocks via defibrillation electrode 24 of defibrillation lead 22 if the tachyarrhythmia is still present and determined to require defibrillation therapy. As used herein, the term "shock" or "shocks" refers to a defibrillation shock(s), cardioversion shock(s), or other shock delivered to convert a tachyarrhythmia to a sinus rhythm. As will be described in further detail herein, ICD 20 analyzes the sensed electrical signals on lead 22 to detect pacing therapy provided by pacing device 16 and, in response to detecting the pacing therapy, modifies the sensing and/or tachyarrhythmia detection to reduce the likelihood that the pacing therapy negatively impacts the sensing and detection of ICD 20.

As described above, cardiac system 10 also includes at least one cardiac pacing device 16. In the example illustrated in FIG. 1, cardiac pacing device 16 is an implantable leadless pacing device that provides pacing therapy to heart 18 via a pair of electrodes carried on the housing of pacing device 16. An example cardiac pacing device is described in U.S. patent application Ser. No. 13/756,085 to Greenhut et al., entitled "SYSTEMS AND METHODS FOR LEADLESS PACING AND SHOCK THERAPY," the entire content of which is incorporated herein by reference. Since cardiac pacing device 16 includes two or more electrodes carried on the exterior its housing, no other leads or structures need to reside in other chambers of heart 18.

In the example of FIG. 1, cardiac pacing device 16 is implanted within right ventricle of heart 18 to sense electrical activity of heart 18 and deliver pacing therapy, e.g., anti-tachycardia pacing (ATP) therapy, bradycardia pacing therapy, and/or post-shock pacing therapy, to heart 18. Pacing device 16 may be attached to a wall of the right ventricle of heart 18 via one or more fixation elements that penetrate the tissue. These fixation elements may secure pacing device 16 to the cardiac tissue and retain an electrode (e.g., a cathode or an anode) in contact with the cardiac tissue. However, in other examples, system 10 may include additional pacing devices 16 within respective chambers of heart 12 (e.g., right or left atrium and/or left ventricle). In further examples, pacing device 16 may be attached to an external surface of heart 18 (e.g., in contact with the epicardium) such that pacing device 16 is disposed outside of heart 18.

Pacing device 16 may be capable sensing electrical signals using the electrodes carried on the housing of pacing device 16. These electrical signals may be electrical signals generated by cardiac muscle and indicative of depolarizations and repolarizations of heart 18 at various times during the cardiac cycle. Pacing device 16 may analyze the sensed electrical signals to detect tachyarrhytmias, such as ventricular tachycardia or ventricular fibrillation. In response to detecting the tachyarrhytmia, pacing device 16 may, e.g., depending on the type of tachyarrhythmia, begin to deliver ATP therapy via the electrodes of pacing device 16. In addition to or instead of ATP therapy, pacing device 16 may also deliver bradycardia pacing therapy and post-shock pacing therapy.

Cardiac pacing device 16 and subcutaneous ICD system 14 are configured to operate completely independent of one another. In other words, pacing device 16 and subcutaneous ICD system 14 are not capable of establishing telemetry communication sessions with one another to exchange information about sensing and/or therapy using one-way or two-way communication. Instead, each of pacing device 16 and subcutaneous ICD system 14 analyze the data sensed via their respective electrodes to make tachyarrhythmia detection and/or therapy decisions. As such, each device does not know if the other will detect the tachyarrhythmia, if or when it will provide therapy, and the like.

During a tachyarrhythmia that could be treated with either ATP or a shock(s) (e.g., defibrillation or cardioversion shock(s)), it is important to ensure that ATP therapies do not overlap or take place after the shock. Applying ATP after a shock could be pro-arrhythmic and present a hazard to the patient. Moreover, the delivery of the pacing from pacing device 16 could interference with sensing and tachyarrhythmia detection of subcutaneous ICD 20. This interference could take the form of decreased sensitivity (e.g., inability to detect ventricular tachycardia (VT) and/or ventricular fibrillation (VF)) or decreased specificity (e.g., inability to withhold therapy for tachyarrhythmia's determined to not require a shock, such as supraventricular tachycardia (SVT), sinus tachycardia (ST), normal sinus rhythm, atrial fibrillation, atrial flutter, or the like). Systems could be designed to provide device-to-device communication between subcutaneous ICD system 14 and pacing device 16, but this may add complexity to the system and not be highly effective or fast enough to prevent unwanted ATP therapies post shock. The techniques described herein reduce and, in some cases, eliminate the interference with sensing and tachyarrhythmia detection of subcutaneous ICD 20.

Although FIG. 1 is described in the context of a subcutaneous ICD system 14 and a leadless pacing device 16, the techniques may be applicable to other coexistent systems. For example, an ICD system that includes a lead having a distal portion that is implanted at least partially under the sternum (or other extra-pericardial location) instead of being implanted above the ribs and/or sternum. As another example, instead of a leadless pacing device, a pacing system may be implanted having a pacemaker and one or more leads connected to and extending from the pacemaker into one or more chambers of the heart or attached to the outside of the heart to provide pacing therapy to the one or more chambers. As such, the example of FIG. 1 is illustrated for exemplary purposes only and should not be considered limiting of the techniques described herein.

Figure 2:
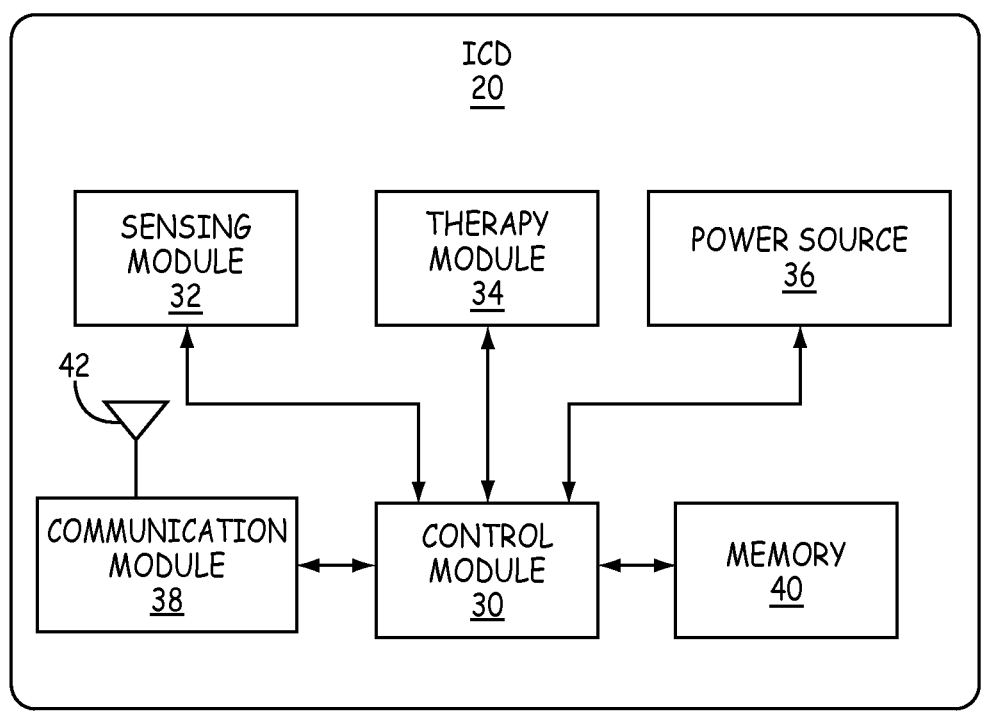
FIG. 2 is a functional block diagram of an example configuration of electronic components of an example ICD.

FIG. 2 is a functional block diagram of an example configuration of electronic components of an example ICD 20. ICD 20 includes a control module 30, sensing module 32, therapy module 34, communication module 38, and memory 40. The electronic components may receive power from a power source 36, which may, for example, be a rechargeable or non-rechargeable battery. In other embodiments, ICD 20 may include more or fewer electronic components. The described modules may be implemented together on a common hardware component or separately as discrete but interoperable hardware, firmware or software components. Depiction of different features as modules is intended to highlight different functional aspects and does not necessarily imply that such modules must be realized by separate hardware, firmware or software components. Rather, functionality associated with one or more modules may be performed by separate hardware, firmware or software components, or integrated within common or separate hardware, firmware or software components.

Sensing module 32 is electrically coupled to some or all of electrodes 24, 26, and 28 via conductors of lead 22 and one or more electrical feedthroughs, and is also electrically coupled to the housing electrode via conductors internal to the housing of ICD 20. Sensing module 32 is configured to obtain electrical signals sensed via one or more combinations of electrodes 24, 26, and 28, and the housing electrode of ICD 20, and process the obtained electrical signals.

Sensing module 32 may include one or more analog components, digital components or a combination thereof. Sensing module 32 may convert the sensed signals to digital form and provide the digital signals to control module 30 for processing or analysis. For example, sensing module 32 may amplify signals from the sensing electrodes and convert the amplified signals to multi-bit digital signals using an analog-to-digital converter (ADC). Sensing module 32 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 30. Sensing module 32 may also process the sensed signals to output an electrocardiogram to control module 30.

Control module 30 may process the signals from sensing module 32 to monitor for a tachyarrhythmia, such as VT or VF. In response to detecting the tachyarrhythmia, control module 30 may control therapy module 34 to charge a storage element within therapy module 34, and, when necessary, deliver a cardioversion or defibrillation pulse to terminate the tachyarrhythmia. The cardioversion or defibrillation pulse may be provided using a therapy vector between defibrillation electrode 24 of lead 22 and the housing electrode of ICD 20. Therapy module 34 may, for example, include one or more capacitors, transformers, switches, and the like. Control module 30 may control therapy module 34 to generate and deliver cardioversion or defibrillation shocks having any of a number of waveform properties, including leading-edge voltage, tilt, delivered energy, pulse phases, and the like.

As described above with respect to FIG. 1, pacing device 16 independently detects a tachyarrhythmia and, in some instances, provides ATP in an attempt to terminate the tachyarrhythmia. The ATP therapy provided by pacing device 16 may interfere with sensing and detection of tachyarrhythmia by sensing module 32 of ICD 20. This interference could take the form of decreased sensitivity (e.g., inability to detect VT or VF) or decreased specificity (e.g., detecting VT or VF for rhythms in which no therapy is necessary). ICD 20 is configured to detect the ATP provided by pacing device 16 by analyzing the sensed electrical signals from lead 22 and, adjust sensing and/or detection in response to detecting the ATP. To this end, sensing module 32 may include additional components configured to detect pacing spikes within the sensed electrical signals from lead 22. For example, sensing module 32 may include a pace pulse detector as described in further detail with respect to FIGS. 3 and 5.

Communication module 38 includes any suitable hardware, firmware, software or any combination thereof for communicating with an external device, such as a clinician programmer or patient monitoring device. For example, communication module 38 may include appropriate modulation, demodulation, frequency conversion, filtering, and amplifier components for transmission and reception of data via antenna 42. Antenna 42 may be located within the connector block of ICD 20 or within housing ICD 20.

The various modules of ICD 20 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 40 may include computer-readable instructions that, when executed by control module 30 or other component of ICD 20, cause one or more components of ICD 20 to perform various functions attributed to those components in this disclosure. Memory 40 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
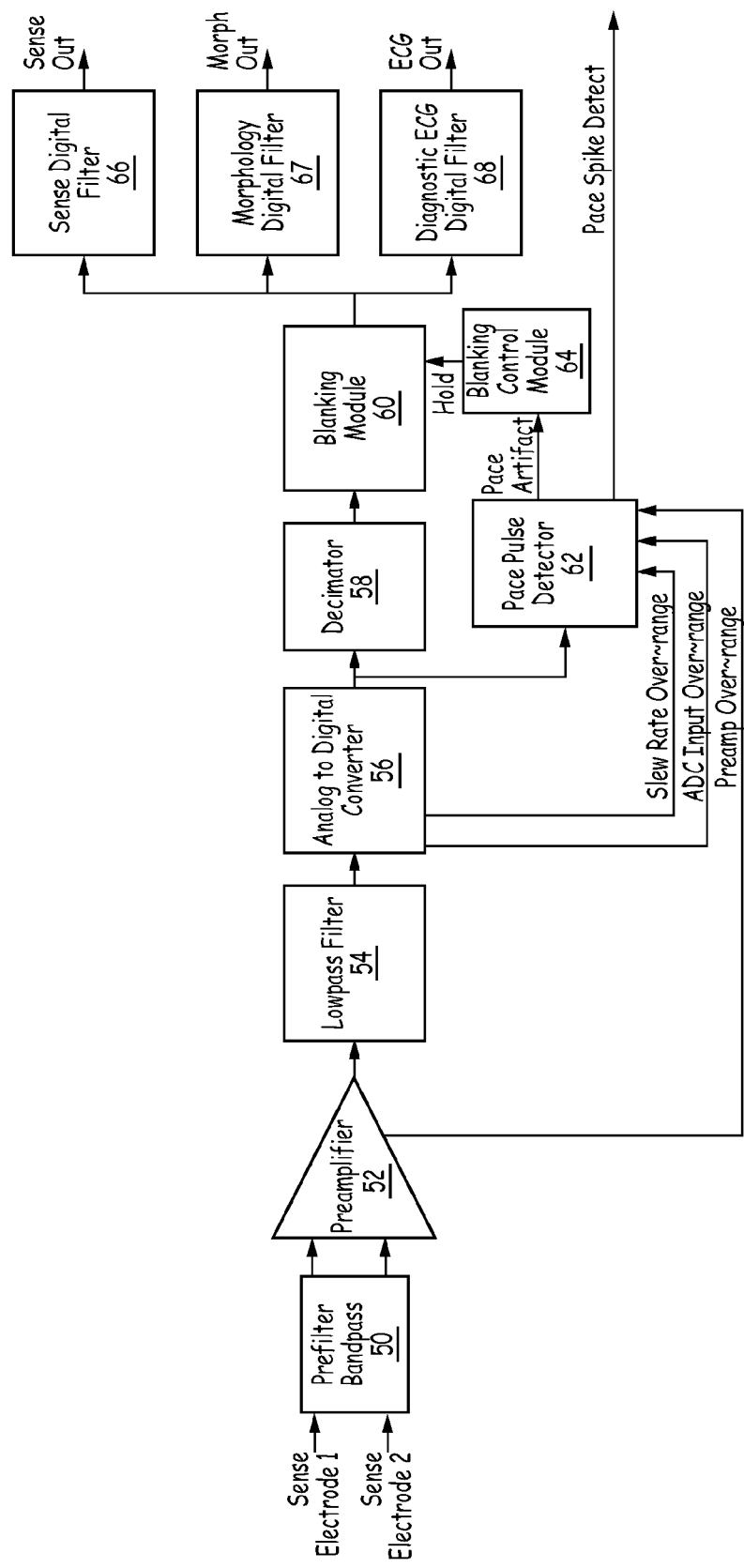
FIG. 3 is a block diagram of an example sensing channel of a sensing module of an ICD with pace detection and blanking.

FIG. 3 is a block diagram of an example sensing channel of a sensing module, such as sensing module 32 of FIG. 2. The sensing channel may, for example, be a sensing channel for processing sensed signals on a first sensing vector. Sensing module 32 may include a similar sensing channel for each of the sensing vectors to be processed. In the case of multiple sensing channels, sensing module 32 may include duplicate components or each sensing filter may share one or more components.

The sensing channel illustrated in FIG. 3 includes a prefilter 50, preamplifier 52, low-pass filter 54, analog-to-digital converter (ADC) 56, decimator 58, blanking module 60, pace pulse detector 62, blanking control module 64, sense digital filter 66, ECG morphology digital filter 67, and ECG filter 68. The configuration of the sensing channel is exemplary in nature and should not be considered limiting of the techniques a described herein. The sensing channel of sensing module 32 may include more or fewer components than illustrated and described in FIG. 3.

The electrical signals sensed on a sensing vector of lead 22 are provided to prefilter 50 of sensing module 32. The electrical signals provided to prefilter 50 are differential signals. Prefilter 50 may include one or more passive resistor-capacitor (RC) band-pass filters and protection diodes to filter out direct current, high frequency, and high voltage transient signals. The prefiltered signal from prefilter 50 is provided to preamplifier 52, which amplifies the input signals by a gain and converts the prefiltered differential signals to a single-ended signal.

Preamplifier 52 may, in some instances, also generate a signal when an input or output level exceeds a range of the preamplifier (labeled "preamp over-range" in FIG. 3). The range of preamplifier may be between ±10-20 millivolts (mV). However, the range may be smaller or larger in other embodiments. Preamplifier 52 may generate the preamp over-range signal when the input signal causes the preamplifier to be over-range. Such a condition may be indicative of an input signal greater than approximately 10-20 mV, which is much larger than the expected amplitude of an electrical signal corresponding to a ventricular contraction, which would be closer to 1-5 mV. The preamp over-range signal is provided to pace pulse detector 62 for analysis in determining whether or not a pace spike or a pace artifact are detected as will be described further below.

The preamplified signal is output by preamplifier 52 to low pass filter 54. Low pass filter 54 may provide anti-alias filtering and noise reduction prior to digitization. The filtered signal output by low pass filter 54 is provided to ADC 56, which converts the analog signal to a digital bit stream. In one example, ADC 56 may be a sigma-delta converter (SDC), but other types of ADCs may be used. The output of ADC 56 is provided to decimator 58, which functions as a digital low-pass filter that increases the resolution and reduces the sampling rate. In one example, ADC may have an 8-bit resolution and 16 kiloHertz (kHz) sampling rate. Decimator 58 may have a 16-bit resolution and a 1 kHz sampling rate. These values are for example purposes only and should not be considered limiting of the techniques described herein.

ADC 56 may also have other characteristics, such as an input range and a slew rate range. In one example, the input range of ADC 56 may be between 25-825 mV and the slew rate range may be 0 to 6.24 mV/ms, 3.12 mV/ms, 1.56 mV/ms, or 0.78 mV/ms. ADC 56 may be configured to generate an ADC input over-range signal when the input signal is greater than the input range of ADC 56. Such a condition may, for example, be indicative of a sensed signal greater than approximately 10-20 mV peak which is much larger than an expected ventricular contraction 1-5 mV. Alternatively or additionally, ADC 56 may be configured to generate a slew rate over-range signal when the slew rate is faster than can be tracked by ADC 56. For example, the accumulated voltage error signal internal to ADC 56 may be monitored with a comparator and when the error signal exceeds the comparator threshold, the slew over-range is tripped. The slew-rate overange may, in one instance, may be generated or asserted when the slew rate of the input signal is greater than or equal to 4 mV/ms. The ADC input over-range signal and/or the slew rate over-range signal are provided to pace pulse detector 62 for analysis in determining whether a pace spike or a pace artifact are detected.

In conventional sensing channels, the digitized signal is provided directly to sense filter 66 and ECG filter 68. Sense digital filter 66 includes a bandpass filter (e.g., 10 to 32 Hz), rectifier, and a threshold detector. The sense digital filter 66 may, in one example, include an auto-adjusting threshold that dynamically varies between a percentage of the peak value of the signal input to sense digital filter 66 and a programmed minimum value. The output of sense digital filter 66, which is provided to control module 30, indicates that a cardiac event is detected, e.g., an R-wave in the case of ventricular sensing channel or a P-wave in the case of a atrial sensing channel, whenever the sensed electrical signal exceeds the threshold. In parallel with the processing by sense digital filter 66, diagnostic ECG filter 68 applies a wide bandwidth filter to output an ECG signal and a morphology ECG filter 67 applies a filter (e.g. with a bandwidth of 2.5 to 32 Hz) go output a signal for morphology analysis (including gross-morphology analysis and beat-based morphology analysis described below in further detail) by control module 30.

Figure 4A:
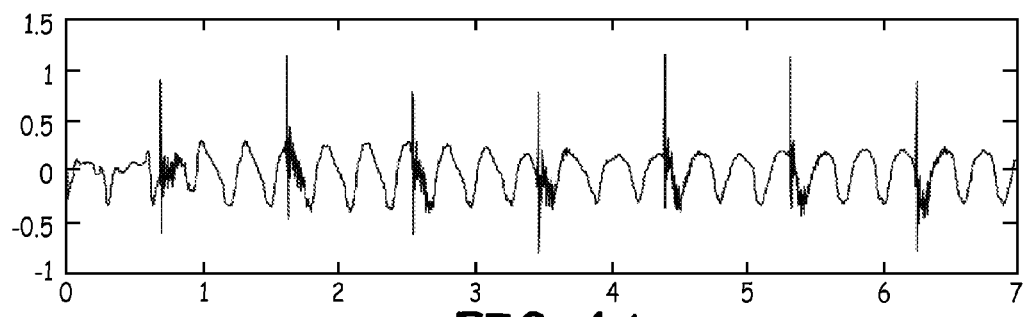
FIG. 4A illustrates a plot of an ECG of a ventricular tachycardia with pacing spikes.
Figure 4B:
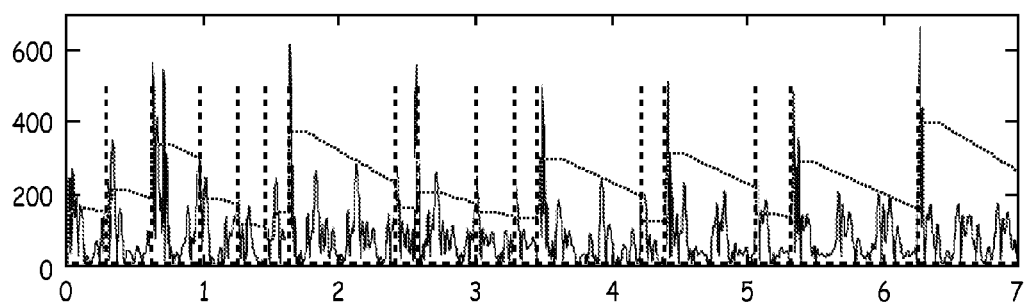
FIG. 4B illustrates a plot representing operations performed on the ECG and occurring within sense digital filter showing the impact of pacing artifacts on sensing performance.

As described above, the pacing pulses delivered by pacing device 16 could interfere with sensing and tachyarrhythmia detection of subcutaneous ICD 20 either by decreasing sensitivity and/or specificity. FIGS. 4A and 4B illustrate example electrical signals in which pacing pulses are delivered on top of a ventricular tachycardia. FIG. 4A illustrates an ECG of the rhythm and FIG. 4B illustrates a plot representing operations occurring within sense digital filter 66. In the plot illustrated in FIG. 4B, the solid line signal is the bandpass filtered and rectified ECG. The dotted line signal is the auto-adjusting sensing threshold of sense digital filter 66, which as described above, may dynamically vary between a percentage of the peak value of the signal input to sense digital filter 66 and a programmed minimum value. When the ECG signal exceeds the auto-adjusting sensing threshold, a sensed event is detected, as indicated by the vertical bold dashed lines. The sense digital filter outputs these detected sensed events to control module 30 for further processing/analysis.

As can be seen from the illustrations of FIGS. 4A and 4B, the large amplitude of the pacing pulses cause the auto adjusting sensing threshold to increase to a value that is too large to detect at least some of the cardiac events of the underlying rhythm subsequent to the pacing pulse. In turn, control module 30 does not have an accurate representation of cardiac events for use in detecting a tachyarrhythmia. The large pacing pulse may also cause artifacts in the ECG signal for a short time after the pacing pulse due to the pacing pulse exceeding the input range of the preamplifier, the input range of the ADC, the slew rate of the ADC, or otherwise affecting a component of the sensing channel.

To account for the possible interference in sensing and tachyarrhythmia detection of ICD 20 caused by the independent pacing therapy provided by pacing device 16, ICD 20 includes pace pulse detector 62, blanking module 60, and blanking control module 64 within the sensing channel(s). Pace pulse detector 62 obtains the signal output by ADC 56 in parallel with decimator 58. Pace pulse detector 62 may include one or more components to process the signal obtained from ADC 56 to identify characteristics of a pacing pulse. In one example, pace pulse detector 62 may process the signal input from ADC 56 to analyze an amplitude of the signal, a slew rate of the signal, and/or a pulse width of the signal. Pace pulse detector 62 may include a filter configured to pass electrical signals corresponding to pacing pulses and reject cardiac electrical signals (e.g., a band-pass filter that passes signals having frequencies between approximately 100 Hz and 2000-4000 Hz, for example or a high-pass filter that passes signals having frequencies greater than 100 Hz). Alternatively or additionally, pace pulse detector 62 may include a differentiator, difference filter, or a first order derivative filter that may be used to obtain a signal representative of the slew rate of the sensed signal.

Pace pulse detector 62 may also include one or more threshold detectors. For example, pace pulse detector may include a slew rate threshold detector that compares the output of a differentiator or a first order derivative filter to a slew rate threshold. If the slew rate exceeds the slew rate threshold, pace pulse detector 62 determines that the signal corresponds to a pacing pulse. Pace pulse detector 62 may likewise analyze the amplitude of the input signal. In some instances, pace pulse detector 62 may analyze a combination of slew rate and amplitude to detect the presence of a pacing pulse. For example, if the slew rate exceeds the slew rate threshold, pace pulse detector 62 may compare the amplitude of the sensed signal to one or more amplitude thresholds using amplitude threshold detectors.

In some instances, pace pulse detector 62 may include two pace pulse detectors. A first detector, e.g., referred to herein as a pace artifact detector, has a first threshold that is configured to detect only pacing pulses that are large enough in amplitude, slew rate, or pulse width to impact the sensitivity for tachyarrhythmia detection of ICD 20. Such pacing pulses will be referred to herein as pace artifacts. A second detector, e.g., referred to herein as a pace spike detector, has a second threshold that is configured to detect all pacing pulses regardless of whether they are large enough to impact tachyarrhythmia detection. These pacing pulses will be referred to herein as pace spikes. Although no blanking will occur for these smaller pacing spikes, control module 30 may still utilize this information in its tachyarrhythmia detection. The pace spike detector will have a higher sensitivity than the pace artifact detector so that it can detect pacing pulses having small amplitudes and/or pulse widths. As such, pace artifacts will also be detected as pace spikes. In other instances, pace pulse detector 62 may include only a single detector. As such, pace pulse detector 62 may analyze the slew rate, amplitude, pulse width or other characteristic to detect pace artifacts and pace spikes.

In addition to inputting the signal from ADC 56, pace pulse detector 62 also obtains the preamp over-range signal from preamplifier 52, the ADC input over-range signal from ADC 56, and the slew rate over-range signal from ADC 56. All or at least some of these signals may be indicative of a pacing artifact. For example, a preamplifier over-range signal that is present or asserted for a threshold period of time is likely indicative of a sensed signal that is much larger than an expected ventricular contraction 1-5 mV. As another example, an ADC slew rate over-range signal that is present or asserted for more than a threshold amount of time, e.g., approximately 1 ms, is likely indicative of a pacing artifact as the slew rate limit of ADC 56 would not be exceeded for a very long time for EMI (e.g., less than 1 ms) and never exceeded for sensed ventricular contractions. In some instances, the threshold time may be adjustable. In a further example, an ADC input over-range signal that is present or asserted for more than a threshold amount of time, e.g., about 1 ms, is likely indicative of a sensed signal that is has a high amplitude for much longer than a ventricular contraction. As such, each of these over-range signals may meet particular criteria that is likely indicative of the presence of a pace pulse that is high enough in amplitude and/or pulse width to impact the sensitivity for tachyarrhythmia detection by ICD 20, i.e., a pace artifact. These criteria will be referred to as over-range conditions. In other examples, the simple fact the over-range condition occurs (regardless of how long it occurs for) may be an over-range condition.

Pace pulse detector 62 analyzes these over-range signals as well as the pace spike analysis and/or pace artifact analysis performed as described above and outputs a pace artifact detection signal and a pace spike detection signal based on the analyses. In one example, pace pulse detector 62 generates and/or asserts the pace artifact detect signal when any of the over-range conditions are met or the amplitude, slew rate, and pulse width analysis indicates that the presences of a pacing artifact. Likewise, pace pulse detector 62 generates and/or asserts the pace spike detect signal when any of the overrange conditions are met or the amplitude, slew rate, and pulse width analysis indicates that the presences of a pacing spike. The pace artifact analysis and the pace spike analysis may be capable of detecting pace artifacts and pace spikes that are not large enough to trigger the over-range conditions described above.

Pace spike detector 62 outputs the pace artifact detect signal to blanking control module 64 and outputs the pace spike detect signal to control module 30.

Blanking control module 64 initiates blanking when the pace artifact detect signal is asserted. As such, blanking control module 64 initiates blanking when any one of the over-range conditions is met or the pace artifact detection analysis indicates the presence of a pacing pulse that is high enough in amplitude and/or pulse width to impact the sensitivity for tachyarrhythmia detection. The blanking may continue for a predetermined period of time, until the pace artifact detect signal is deasserted, or until the pace artifact signal has been deasserted for a certain period of time. In one example, blanking control module 64 may initiate blanking on only the sensing channel on which the pacing artifact was detected. In another example, blanking control module 64 may initiate blanking on all of the sensing channels when a pacing artifact is detected on any one of the sensing channels. When blanking is desired, blanking control module 64 provides a control signal to blanking module 60 to initiate blanking of the signal output from decimator 58. Blanking module 60 may include a sample and hold circuit that holds the value of the signal in response to receiving the control signal from blanking control module 64. Blanking module 60 continues to hold the value of the sensed electrical signal until the blanking control module 64 removes the control signal. In one example, blanking control module 64 may apply the hold signal, and thus cause blanking, for less than or equal to approximately twenty (20) milliseconds (ms). In other embodiments, blanking module 60 may provide a linear interpolation or other interpolation between the value at the start of blanking and the value at the end of blanking.

Blanking module 60 may, in some instances, also include a delay block that introduces a delay into the electrical signal prior to the sample and hold circuit to allow for detection of the pacing pulse by pace pulse detector 62 and analysis of the inputs by blanking control module 64 to determine whether to blank the electrical signal before the artifact from the pacing pulse has a chance to propagate into the sense and ECG outputs. The delay introduced into the sensing channel may be between approximately 1-20 ms depending up on where in the sensing channel the blanking occurs and whether or not blanking module 60 performs interpolation as described above. In some instances, this delay block may not exist or may be for a shorter period of time since the decimator 58 also provides some delay between the ADC output and the blanking module 60.

Figure 5A:
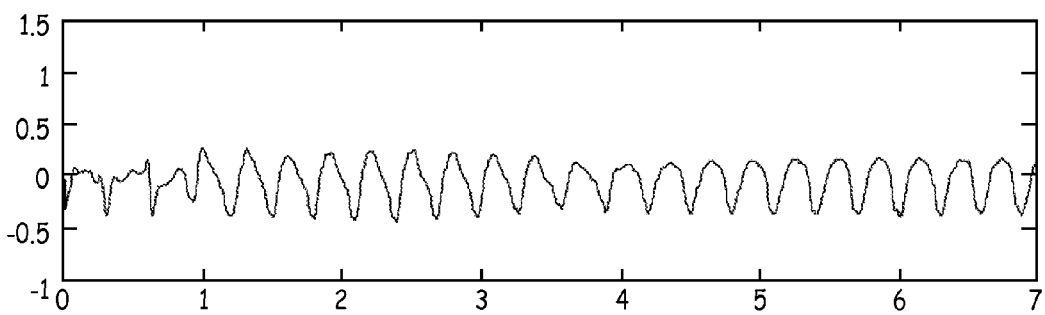
FIG. 5A illustrates a plot of the ECG of FIG. 4A after blanking in accordance with techniques of this disclosure.
Figure 5B:
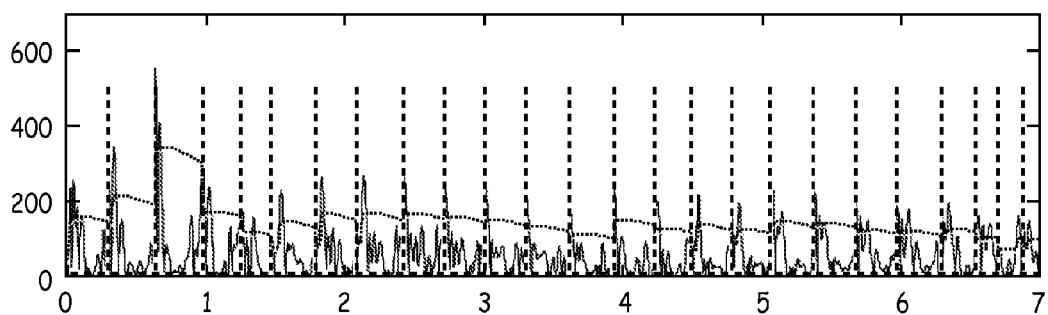
FIG. 5B illustrates a plot representing operations performed by sense digital filter on the ECG after blanking in accordance with techniques of this disclosure.

The output of blanking module 60 is provided to sense digital filter 66, ECG morphology filter 67, and diagnostic digital ECG filter 68, whose operation are described above. By providing the blanking described above, the pace artifact is significantly reduced as illustrated in the plots in FIG. 5A and FIG. 5B. FIG. 5A illustrates the same signal as FIG. 4A, but with a 24 ms blanking applied to each of the detected pace artifacts. Likewise, FIG. 5B illustrates the plot of operations within the digital sense filter 66. As can be seen in FIG. 5B, by blanking the sensing channel in response to detecting pace artifacts, the auto-adjusting threshold remains in a zone that is capable of detecting all of the cardiac events. Thus, control module 30 would have more accurate sensing information to monitor for tachyarrhythmia.

The sensing channel illustrated in FIG. 3 is one example sense channel. Other configurations of a sense channel or arrangement of components in the sense channel may be utilized without departing from the scope of this disclosure. In other embodiments, for example, pace pulse detector 62 may obtain its input from other components earlier in the sensing channel processing stage, e.g., from prefilter 50, preamplifier 52, or low-pass filter 54. In another example, blanking module 60 may be located elsewhere within the sensing channel, such as between preamplifier 52 and low-pass filter 54. In such an example, the blanking may be implemented using a resister in series with a switch to create a sample and hold circuit.

Figure 6:
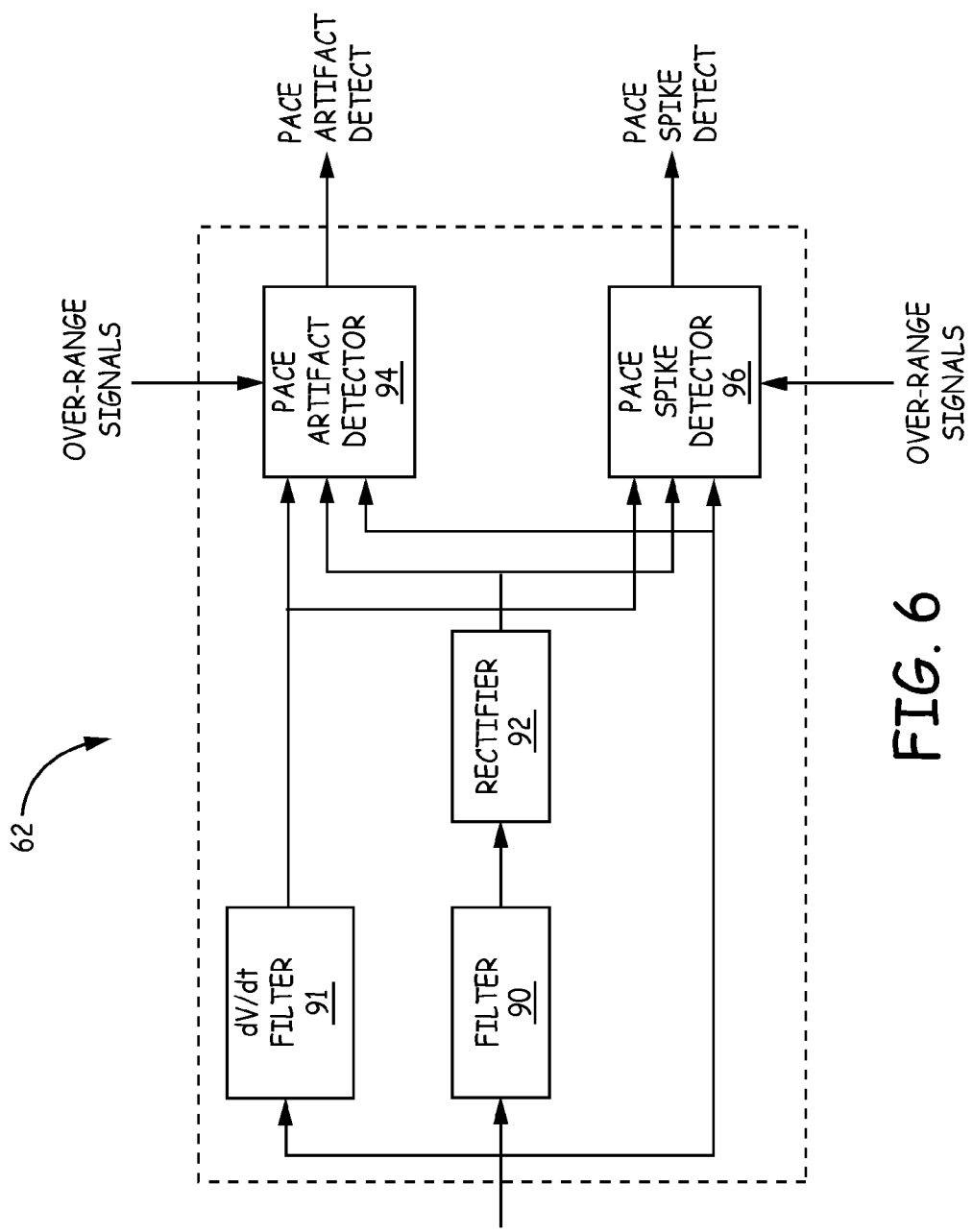
FIG. 6 is block diagram illustrating an example pace pulse detector.

FIG. 6 is block diagram illustrating an example pace pulse detector 62. Pace pulse detector 62 includes a filter 90, a derivative (dV/dt) filter 91, a rectifier 92, a pace artifact detector 94, and a pace spike detector 96. Pace pulse detector 62 inputs the signal output by ADC 56. This signal is provided to filter 91, dV/dt filter 91, pace artifact detector 94 and pace spike detector 96. However, the various components of pace pulse detector 62 may obtain the signal from other components of the sensing channel, such as directly from the preamplifier 52.

Filter 90 of pace pulse detector 62 filters the signal output from ADC 56. Filter 90 may be configured to pass electrical signals corresponding to pacing pulses and reject cardiac electrical signals. Filter 90 may, in one example, be a band-pass filter that passes signals having frequencies between approximately 100 Hz and 1000-4000 Hz. In another example, filter 90 may be a high-pass filter that passes signals having frequencies greater than 100 Hz. In other examples, filter 90 may be another type of filter, such as a derivative filter. In a further example, the signal may not be filtered at all. Rectifier 92 rectifies the filtered signal from filter 90. The rectified signal is then is provided to pace artifact detector 94 and pace spike detect detector 96.

The dV/dt filter 91 generates a difference signal (e.g., x(n)−x(n−1) of the output of ADC 56. The difference signal includes spikes the correspond with portions of the signal having high slew rates. The difference signal is also provided to pace artifact detector 94 and pace spike detect detector 96.

Pace artifact detector 94 and pace spike detector 96 analyze some or all of the raw input signal from ADC 56, the rectified signal from rectifier 92, the difference signal from dV/dt filter 91 to detect the presence of a pace artifact and a pace spike, respectively. In one example, pace artifact detector 94 and pace spike detect detector 96 may detect the pace artifact and pace spike, respectively, using only amplitude or only slew rate. In another example, pace artifact detector 94 and pace spike detect detector 96 may detect the pace the pace artifact and pace spike, respectively, using a combination of amplitude, slew rate, and pulse width.

Pace artifact detector 94 and pace spike detect detector 96 may compare raw input signal from ADC 56, the rectified signal from rectifier 92, the difference signal from dV/dt filter 91 to respective thresholds to detect the pace artifact and/or the pace spike. The thresholds of pace artifact detector 94 and pace spike detector 96 may be different such that the pace artifact detector 94 is configured to only detect pace artifacts having large enough amplitudes to impact the tachyarrhythmia detection algorithm performed by control module 30 while pace spike detector 94 is configured to detect pacing pulses regardless of whether they are large enough to impact the tachyarrhythmia detection algorithm performed by control module 30. Therefore, the pace artifact threshold(s) (e.g., artifact slew rate threshold or amplitude threshold) therefore are generally larger than the pace spike threshold(s) (e.g., spike slew rate threshold or amplitude threshold). As such, pace spike detector 94 will have a higher sensitivity than the pace artifact detector 96 so that it can detect pacing pulses with smaller amplitudes and pulse widths.

In some instances, some or all of the pace artifact thresholds and the pace spike thresholds may be automatically adjustable. For example, one or both of pace artifact amplitude threshold and the pace spike amplitude threshold may be dynamically adjusted based on the peak amplitude of the detected pulse to allow threshold to be raised higher to avoid EMI if the detected pace pulses are large in amplitude. Alternatively or additionally, one or both of the pace artifact amplitude threshold and the pace spike amplitude threshold may be dynamically adjusted based on a baseline R-wave amplitude. In this case, if the R-waves are large, the threshold for sensing pace artifacts and/or pace spikes may need to set higher. In one example, the increase may be proportionate, e.g., a 50% increase in sensed R-wave amplitude would lead to a 50% increase in pacing artifact detection threshold.

As further illustrated in FIG. 6, pace artifact detector 94 and pace spike detector 96 also receive the over-range signals from the various components of the sensing channel (e.g., the preamp over-range signal from preamplifier 52, the ADC input over-range signal from ADC 56, and the slew rate over-range signal from ADC 56). Based on the analysis of the over-range signals and the processing of the signals output by ADC 56, pace artifact detector 94 and pace spike detector 96 output a pace artifact detect signal and a pace spike detect signal, respectively. In one example, pace artifact detector 94 generates and/or asserts the pace artifact detect signal when any of the over-range conditions are met or the amplitude, slew rate, and pulse width analysis of the ADC output indicates the presence of a pacing artifact. Likewise, pace spike detector 96 generates and/or asserts the pace spike detect signal when any of the over-range conditions are met or the amplitude, slew rate, and pulse width analysis indicates the presences of a pacing spike.

The pace artifact detect signal is provided to blanking control module 64 to initiate blanking of one or more of the sensing channels, described in further detail below. Because blanking of the sensing channel(s) may introduce an artifact in the ECG signal, it is desired that blanking is only done when necessary to obtain good tachyarrhythmia detection sensitivity, thus the higher pace artifact thresholds.

The pace spike detect signal and, in some instances, the pace artifact detect signal, may be provided to control module 30 to be used as part of the tachyarrhythmia detection. The pace artifact detect signal and the pace spike detect signal may be provided directly to control module 30 by pace pulse detector 62 or relayed to control module via blanking control module 64. The pace artifact signal and the pace spike detect signal may be provided individually to control module 30. Alternatively, the pace artifact detect signal and the pace spike detect signal could be logically combined (e.g., logically OR'ed) and provided to control module 30. In instances in which multiple sensing channels are analyzed, the pace artifact signal and the pace spike detect signal for each of the sensing channels may be provided individually or logically combined.

The pace artifact detect signal and the pace spike detect signal may be provided to control module 30 using any of a number of techniques. For example, the pace artifact detect signal and the pace spike detect signal outputs from one or both of the sensing channels could be logically combined to generate a single output and used to generate an interrupt signal to control module 30. The advantage of combining signals and generating an interrupt is that it provides notification of the pacing event in a very short time allowing the control module 30 to quickly respond to a pacing pulse. The drawback is that it is possible that an excessive number of interrupts could be generated in certain conditions which may overload the ability of control module 30 to handle the interrupts or cause excessive current drain. Alternatively, the pace artifact detect signal and the pace spike detect signal from all active channels could be combined into a single register and continuously streamed over to control module 30 for storage in memory and later analysis. This provides the advantage of providing more information about the amplitude of the pacing pulse and which channel the pulse was detected on. It also allows control module 30 to process the pacing information on a regular schedule or when processing data for tachyarrhythmia detection rather than as an interrupt which reduce concerns with over-burdening control module 30 with interrupt handling. The drawback to this approach is that it requires additional memory and increases the latency from the pacing pulse being detected until control module 30 can act on the information.

Pace pulse detector 62 of FIG. 6 is one example of such a detector. In other embodiments, pace pulse detector 62 may include only a single detector instead of a pace artifact detector 94 and pace spike detector 96. In further embodiments, pace pulse detector 62 may include more than two threshold detectors. An example of a pace pulse detector that includes more than two threshold detectors is illustrated and described in concurrently filed U.S. Patent Application Publication No. 2015/0305642 and entitled, "PACE PULSE DETECTOR FOR AN IMPLANTABLE MEDICAL DEVICE," (e.g., in FIG. 8 and the associated description), which is incorporated herein by reference in its entirety.

Figure 7:
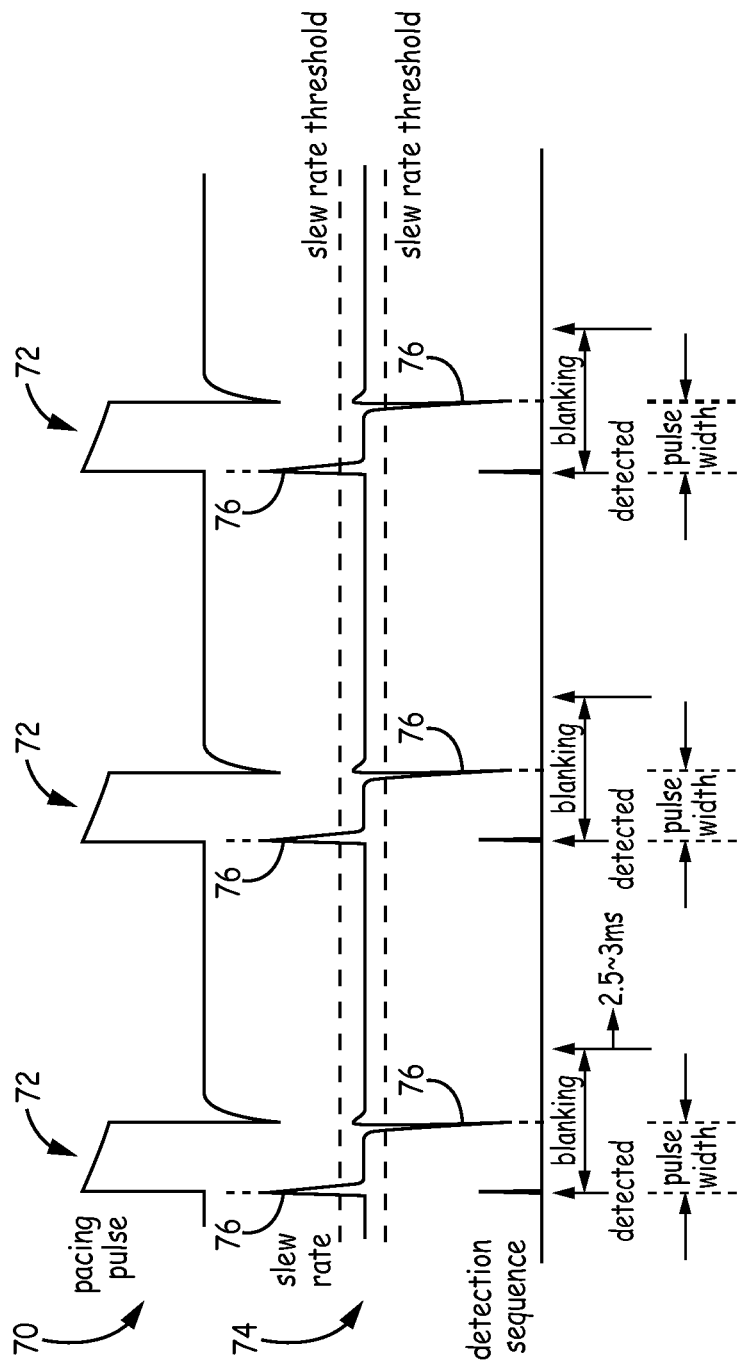
FIG. 7 is a conceptual diagram of a pace pulse detector analyzing the slew rate of the sensed electrical signals having pacing pulses.

FIG. 7 is a conceptual diagram illustrating example operation of pace pulse detector 62. FIG. 7 illustrates an example sensed electrical signal that includes a pacing train 70 that includes at least three pacing pulses 72. FIG. 7 also illustrates an example a slew rate signal 74, which may be output by filter 90 (e.g., a difference filter or first order derivative filter) of pace pulse detector 62. As illustrated in FIG. 7, slew rate signal 74 has spikes 76 that correspond with the edges of pacing pulses 72. Pace pulse detector 62 may compare slew rate signal 74 to a slew rate threshold 78 and when slew rate signal 74 exceeds the slew rate threshold, pace pulse detector 62 may detect the presence of a pacing spike. In order to avoid detecting the trailing edge of pacing pulse 72 as separate pace pulse, pace pulse detector 62 may not count any spike 76 that occurs within a particular period of time, e.g., 2 ms, from a previous spike 76 as a separate pacing pulse. In some instances, pace pulse detector 62 may, however, track these close proximity spikes to estimate pulse width of the pacing pulses. In other examples, detecting a slew rate that exceeds the slew rate threshold would result in further analysis of other characteristics of the detected signal, such as looking at the amplitude of the sensed electrical signal. In one instance, the example slew rate threshold may be equal to 4 mV/ms. However, other thresholds may be utilized.

Figure 8:
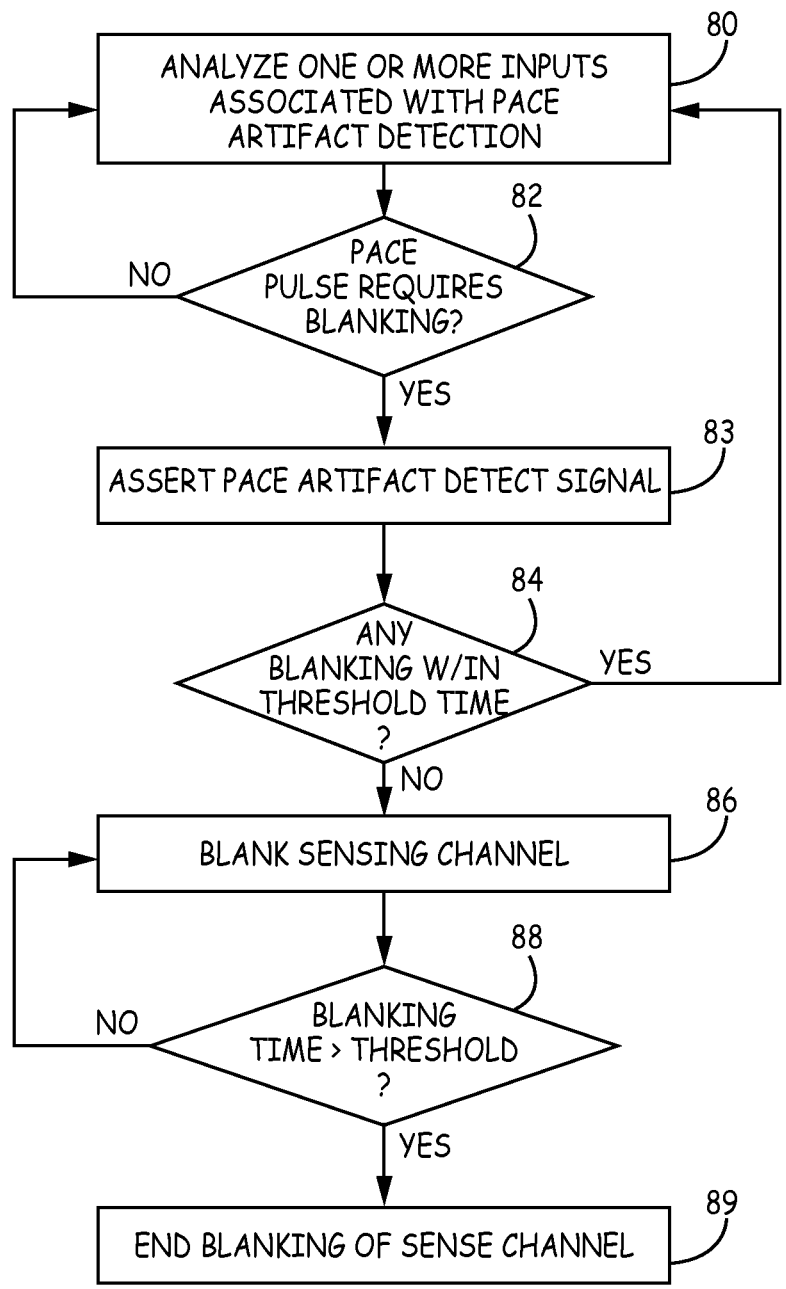
FIG. 8 is a flow diagram illustrating example operation of a sensing channel controlling the blanking of one or more sensing channels based on input indicative of a pacing pulse.

FIG. 8 is a flow diagram illustrating example operation of blanking of one or more sensing channels in accordance with the techniques described herein. Initially, pace pulse detector 62 obtains and analyzes one or more inputs associated with detection of a pacing pulse in the sensing channel (80). In the example sensing module 30 of FIG. 3, for example, pace pulse detector 62 analyzes some or all of a pace artifact detect signal (e.g., based on slew rate, amplitude, pulse width or other characteristic of the received signal), preamp over-range signal, ADC input over-range signal, and ADC slew rate over-range signal. However, in other embodiments, only one of these signals or any combination of two or more of these signals may be analyzed by pace pulse detector 62. Additionally, other signals indicative of a pacing pulse or other artifact in the sensing channel may be analyzed by pace pulse detector 62. Different approaches using a single input or multiple inputs will result in different tradeoffs between sensitivity, specificity, complexity. In some instances, pace pulse detector 62 attempts to limit the blanking of the sensing channel to situations in which the pace pulse is likely to affect tachyarrhythmia detection sensitivity or specificity, e.g., higher amplitude pace pulses or pace artifacts.

Pace pulse detector 62 determines whether any of the inputs are indicative of a pacing pulse requiring blanking, i.e., a pacing artifact (82). As described above with respect to FIG. 3, a pace pulse may have an amplitude, slew rate, or other characteristic that is different than sensed signals (e.g., sensed R-waves or P-waves). For example, pace pulses having amplitudes of greater than approximately 10-20 mV may result in preamplifier 52 and/or ADC 56 to operate in one or more of the input over-range conditions. As another example, pace pulses may have slew rates that exceed the slew rate limit of ADC 56, thus causing activation of the ADC slew rate over-range signal. Likewise, the pace artifact detector 94 may detect a pace pulse likely to cause an artifact based on the amplitude, slew rate, or other characteristic of the signal from ADC 56 or other component. When none of the input signals is indicative of a pacing pulse requiring blanking ("NO" branch of block 82), blanking control module 64 continues to analyze the one or more inputs (80).

When any one of the input signals is indicative of a pacing pulse requiring blanking ("YES" branch of block 82), pace pulse detector 62 asserts the pace artifact detect signal (83). In response to the assertion of the pace artifact detect signal, Blanking control module 64 determines whether the sensing channel has been blanked within a threshold period of time (84). In one example, blanking control 64 will not blank the sensing channel until a period of at least 30-60 ms has passed since the last time the sensing channel was previously blanked. This is intended to prevent excessive blanking in a continuous EMI environment, but still allow blanking on both atrial and ventricular paced events at intervals less than approximately 200 ms. When blanking has been triggered within the threshold period of time ("YES" branch of block 84), blanking control module 64 will not blank the sensing channel and will continue to analyze the one or more inputs (80).

When blanking has not been triggered within the threshold period of time ("NO" branch of block 84), blanking control module 64 initiates blanking of the sensing channel (86). In one example, blanking control module 64 may initiate the blanking of the sensing channel by providing a control signal to blanking module 60 to cause the blanking module to hold the value of the sensed signal, as described above with respect to FIG. 3. In one example, blanking control module 64 may initiate blanking on only the sensing channel on which the pacing artifact was detected. In another example, blanking control module 64 may initiate blanking on all of the sensing channels when a pacing artifact is detected on any one of the sensing channels.

After initiating the blanking of the sense channel, blanking control module 64 determines whether the amount of time that the channel has been blanked is greater than a blanking threshold (88). In some instances, blanking control module 64 may be configured to blank for a predetermined period of time, e.g., 20 ms. When the sensing channel has not been blanked for the predetermined amount of time, ("NO" branch of block 88), blanking control module 64 continues to blank the sensing channel. When the sensing channel has been blanked for the predetermined amount of time, ("YES" branch of block 88), blanking control module 64 discontinues the blanking of the sensing channel (89).

In another embodiment, blanking control module 64 may not blank the sensing channel for a predetermined period of time. Instead, blanking control module 64 may continue to blank the sensing channel until all of the inputs no longer indicate presence of a pacing pulse requiring blanking, all of the inputs no longer indicate presence of a pacing pulse for a threshold period of time, e.g., 5-20 ms, allowing for sensing channel components to settle, or the amount of time since initiating the blanking of the sensing channel is greater than or equal to a maximum blanking duration, e.g., approximately 10-30 ms.

Figure 9:
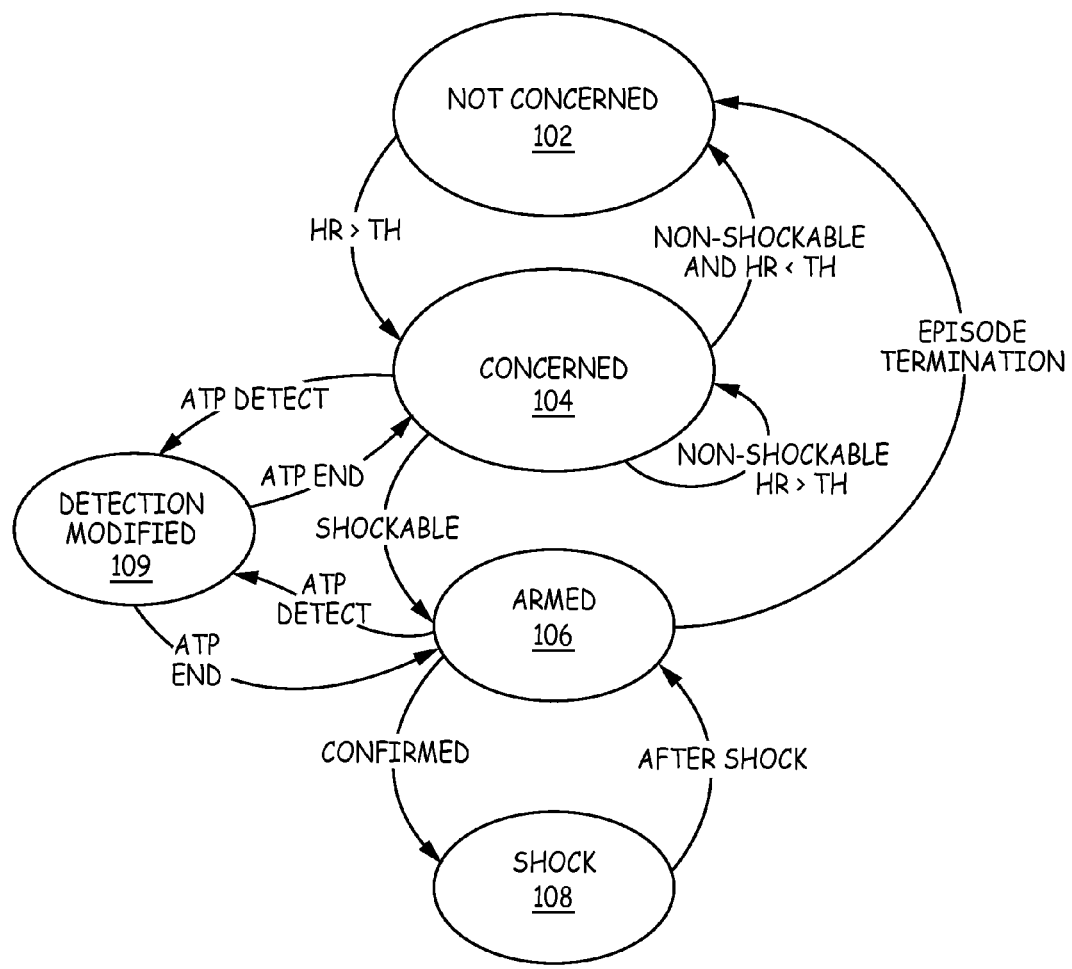
FIG. 9 is a state diagram of an example tachyarrhythmia detection algorithm.

FIG. 9 is a state diagram 100 of an example tachyarrhythmia detection algorithm. During normal operation, ICD 20 operates in a not concerned state 102 in which control module 30 estimates the heart rate of the sensed electrical signals on one or more sensing channels. Control module 30 of ICD 20 may measure a plurality of R-R intervals (i.e., intervals between consecutive sensed ventricular events) on the sensing channel and estimate the heart rate of the sensing channel based on the plurality of measured R-R intervals. In one example, control module 30 stores the most recent 12

R-R intervals on the sensing channel. However, control module 30 may store more or fewer than the 12 most recent R-R intervals. To estimate the heart rate, control module 30 may sort the stored R-R intervals from shortest to longest R-R intervals and estimate the heart rate using only a subset of the R-R intervals. In one example, control module 30 may estimate the heart rate as an average of a subset of the measured R-R intervals (e.g., the average of the 7th through 10th shortest R-R intervals of the most recent 12 R-R intervals). More or fewer R-R intervals may be used in the estimation of the heart rate. As another example, control module 30 may estimate the heart rate using the median of the measured R-R intervals or other specific R-R interval in the group, e.g., the $9^{th}$ shortest R-R interval. The example heart rate estimation techniques described above provide an estimate of the heart rate that is less susceptible to oversensing while maintaining reasonable sensitivity to short R-R intervals as in the case of VT or VF.

In the example described herein, ICD 20 independently estimates the heart rate on two of the sensing vectors described above with respect to FIG. 1 and compares the estimated heart rates to a tachyarrhythmia heart rate threshold, e.g., a VT/VF threshold. In one example, the tachyarrhythmia heart rate threshold may be set to 180 beats per minute. However, other thresholds may be used. Moreover, in other instances, control module 30 may analyze only a single sensing vector or more than two sensing vectors. Example operation in a "not concerned" state is described in paragraphs extending from col. 12, line 7 col. 14, line 61 of the specification as filed and FIG. 7A and FIG. 8 of U.S. Pat. No. 7,761,150 to Ghanem et al., entitled "METHOD AND APPARATUS FOR DETECTING ARRHYTHMIAS IN A MEDICAL DEVICE" (referred to herein as Ghanem et al.) The entire content of the referenced portions of Ghanem et al. are incorporated by reference herein in their entirety.

When control module 30 determines that the heart rate on one or both of the sensing vectors is above the tachyarrhythmia heart rate threshold, control module 30 transitions to a concerned state 104. In the concerned state 104, control module 30 discriminates rhythms requiring shock therapy from those that do not require shock therapy using a combination of heart rate and ECG signal morphology information. In the concerned state 104, for example, control module 30 analyzes the morphology metrics of a plurality of predetermined segments of the sensed electrical signals and classifies each segment as shockable or non-shockable. Control module 30 may perform this morphology analysis on the electrical signals in both sensing vectors in parallel.

In one example, control module 30 analyzes the morphology over a plurality of fixed size segments of the electrical signals, e.g., a pluarlity of 3-second segments. For each of the fixed size segments, control module 30 classifies the EGM in that particular fixed size segment as shockable or non-shockable. In other examples, the length of the fixed size segment analyzed by control module 30 in the concerned state may be shorter or longer than 3 seconds.

The morphology analysis in this concerned state may include a gross morphology analysis in which metrics are computed for the electrical signal over the entire segment, without regard for the location of QRS complexes. The morphology metrics may include, in one example, the signal energy level, noise to signal ratio, muscle noise pulse count, normalized mean rectified amplitude, the mean frequency, the spectral width, and the low slope content. These metrics are exemplary of the type of metrics that may be used and should not be considered limiting of the techniques described herein. Other gross morphology metrics may be used in addition to or instead of the metric listed above.

Control module 30 analyzes the gross morphology metrics to classify the segment as shockable or non-shockable. Control module 30 may analyze one or more of the gross morphology metrics of the segment to determine whether the signal in that particular segment is corrupted by noise and/or artifact. If so, control module 30 may classify the segment as non-shockable or classify the segment based on the classification of the same segment in the other sensing vector. If the control module determines that the signal in the segment is not corrupted by noise and/or artifact, control module 30 analyzes one or more of the gross morphology metrics to determine whether the signal in the segment is in either a VT or a VF shock zone and, if so, classifies the segment as shockable. If the segment is determined to not be in the VT or VF shock zone, the segment is classified as non-shockable. A more detailed description of one example gross morphology analysis is described herein. Another example analysis of gross morphology during operation in a "concerned" state is described in paragraphs extending from col. 14, line 62 col. 26, line 58 and col. 28, line 40-col. 29, line 32 of the specification as filed and FIGS. 7B-7E, 7H, 7I, FIGS. 9A-9C, FIG. 10, and FIGS. 11A-B of Ghanem et al. The entire content of the referenced portions of Ghanem et al. are incorporated by reference herein in their entirety.

If the gross morphology classification of the segment is shockable, control module 30 may, in some instances, also analyze a morphology of the QRS complexes or beats within the segment to classify the segment as shockable or non-shockable. This analysis may be referred to as beat-based morphology analysis since the control module 30 is only analyzing the morphology of windows around a beat instead of the entire segment. The window may, for example, have a range between 120-200 ms. In other instances, the shockable or non-shockable classification may be made solely based on the gross morphology in other examples.

In one example implementation of beat-based morphology analysis, control module 30 may compare the morphology of the beat within the window to a predetermined template morphology to determine if the beat matches the predetermined template (e.g., has a matching score threshold that is greater than or equal to 60%). If more than the threshold number of beats within the segment, e.g, more than 75% of the beats within the segment, do not match the template the segment is classified as shockable. Otherwise the segment is classified as non-shockable. As such, when gross morphology and beat-based morphology are both analyzed, the segment must satisfy both analyses to be classified as shockable. One example beat-based morphology analysis of segments of the sensed electrical signal is described further herein. Another example is described in U.S. patent application Ser. No. 14/250,040, entitled "METHOD AND APPARATUS FOR DISCRIMINATING TACHYCARDIA EVENTS IN A MEDICAL DEVICE USING TWO SENSING VECTORS," particularly in FIGS. 4, 10, and 11 and the associated description of those figures. The entire content of that application is referenced herein in its entirety.

Control module 30 stores the classification of the segments of both the sensing vectors and analyzes the classifications of the plurality of segments to determine whether or not to transition to an armed state in which capacitor charging begins. If control module 30 determines that the rhythm does not require shock therapy (e.g., less than a threshold number of segments are classified as shockable) and the heart rate on at least one sensing vector is less than or equal to the threshold heart rate, control module 30 transitions to the not concerned state 102. If control module 30 determines that rhythm does not require shock therapy, but the heart rate in both sensing vectors is greater than the threshold heart rate, control module 30 continues analyzing the morphology metrics over subsequent fixed size (e.g., 3-second) segments of the electrical signals in the concerned state 104. If control module 30 determines that the rhythm is shockable during the concerned state 104 (e.g., greater than 2 of 3 segments classified as shockable in both sensing channels), control module 30 transitions to an armed state 106. This process is described in further detail with respect to FIG. 13.

In the armed state 106, control module 30 initiates charging of the defibrillation capacitors. Additionally, control module 30 continues to analyze signal morphology (gross morphology alone or gross and beat-based morphology) for termination of the shockable rhythm. Control module 30 may, for example, continue to classify segments of the sensed signal as shockable or non-shockable as described above with respect to the concerned state 104 and analyze the number of segments classified during either the concerned state 104 or the armed state 106 as shockable. If control module 30 determines that the rhythm requiring shock therapy has terminated, control module 30 returns to the not concerned state 102. Control module 30 may determine that the rhythm has terminated, for example, when less than 3 of the last 8 segments are classified as shockable in both sensed signals and the heart rate in at least one of the sensed signals is less that the tachyarrhythmia heart rate threshold. If control module 30 determines the rhythm requiring shock therapy is still present once the charging of the capacitors is completed, e.g., at least five out of the last eight fixed size segments are classified as being shockable, control module 30 transitions from the armed state 106 to a shock state 108. Example operation in an "armed" state is described in paragraphs extending from col. 26, line 59-col. 28, line 16 of the specification as filed and FIG. 7F of Ghanem et al. The entire content of the referenced portions of Ghanem et al. are incorporated by reference herein in their entirety.

In the shock state 108, control module 30 controls therapy module 34 to deliver a shock via a therapy vector that includes defibrillation electrode 24 and returns to the armed state 106 to evaluate the success of the therapy delivered. For example, control module 30 may determine whether the tachyarrhythmia has terminated and transition to the non-concerned state or determine whether the tachyarrhythmia is redetected. The control module 30 may, for instance, redetect the tachyarrythmia when at least 2 of 3 segments are classified as shockable in both sensing channels. Example operation in a "shock" state is described in paragraph extending from col. 28, lines 17-39 of the specification as filed and FIG. 7G of Ghanem et al. The entire content of the referenced portions of Ghanem et al. are incorporated by reference herein in their entirety.

One example technique for operating in the non-concerned state, the concerned state, the armed state and the shock state is described in Ghanem et al., which is incorporated by reference herein in its entirety.

When operating in a detection state in which the morphology metrics of predetermined segments of the sensed electrical signal are being analyzed, e.g., in the concerned state 104 or the armed state 106 of FIG. 8, control module 30 may detect a pacing train and, in response to detecting the pacing train, transition to a modified detection state 109 in which one or more tachyarrhythmia detection modifications are made. The pacing train may be ATP or a non-ATP high rate pacing train or in some instances even conventional pacing trains (e.g., for bradycardia pacing). As described above, delivery of pacing by pacing device 16 may interfere with tachyarrhythmia detection by control module 30. Therefore, control module 30 responds to delivery of pacing by modifying the tachyarrhythmia detection analysis to reduce the likelihood of corruption. As will be described further with respect to flow diagrams below, tachyarrhythmia detection will be modified during the pacing provided by pacing device 16. In some instances, the modification to the tachyarrhythmia detection algorithm will result in delaying delivery of the shock when ATP is detected. The delay in delivery of the shock may be up to 10 seconds in one example. In another example, the delay in delivery of the shock may be between 3-6 seconds.

Figure 10:
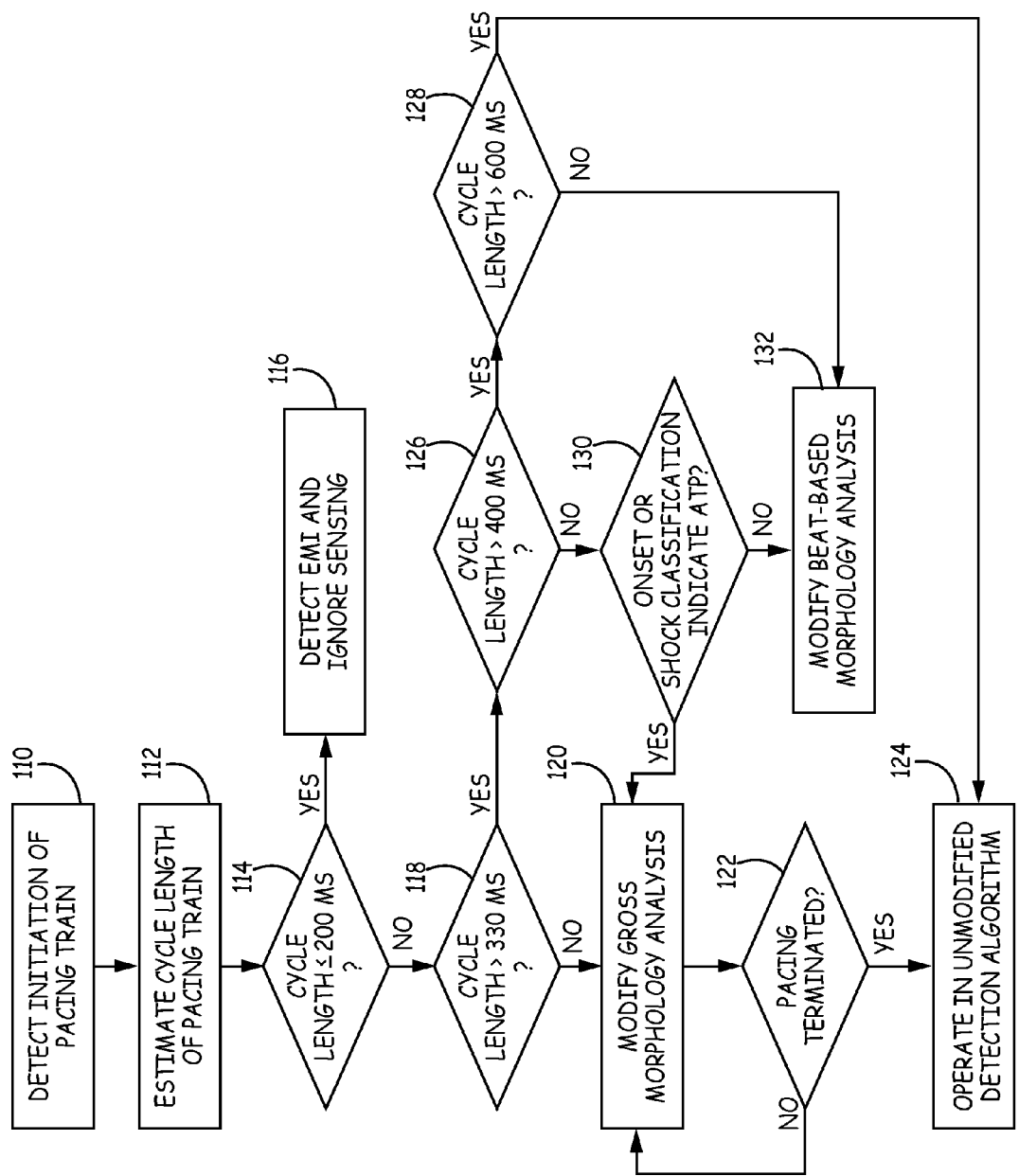
FIG. 10 is a flow diagram illustrating example operation of a control module detecting a pacing train and modifying tachyarrhythmia detection in response to detecting the pacing train.

FIG. 10 is a flow diagram illustrating example operation of control module 30 detecting a pacing train and modifying tachyarrhythmia detection in response to detecting the pacing train. Initially, control module 30 analyzes the pace spike detect signal (or the logical combination of the pace spike detect signal and the pace artifact detect signal) from one or more sensing channels to detect initiation of a pacing train (110). In one example, control module 30 detects the initiation of the pacing train when pace spike detect signal identifies two pacing spikes within 1500 milliseconds of one another. In other words, the start of a pacing train is detected upon the detection of a single paced cycle of less than 1500 ms. However, control module 30 may use a different threshold than 1500 ms to detect the initiation of the pacing train.

Control module 30 estimates a cycle length of the pacing train (112). In one example, control module 30 may compute the two most recent cycle lengths of the pacing train using the three most recently detected pacing spikes and estimate the cycle length of the pacing train as the shortest of the two most recent cycle lengths. This allows for some underdetection of pacing spikes within the pacing train. For example, if 3 out of the last 4 paces are detected, the observed cycle lengths might be X and 2X, control module 30 would estimate the cycle length of the pacing train to be X. In other instances, control module 30 may use more than two most recent cycle lengths (e.g., by using the 3, 4, 5, or more most recent cycle lengths) or only a single cycle length. Moreover, control module 30 may estimate the cycle length of the pacing train using other techniques, such as an average or median of the plurality of most recent cycle lengths instead of selecting the shortest of the two most recent cycle lengths as the estimated cycle length of the pacing train.

Control module 30 determines whether the estimated cycle length is less than or equal to a first cycle length threshold (114). The first cycle threshold may be minimum cycle length that may be confidently classified as ATP. In one example, the minimum cycle length threshold may be equal to 200 milliseconds. When the estimated cycle length is less than or equal to the first cycle length threshold ("YES" branch of block 114), control module 30 determines that the detected pacing train is likely EMI and the signal is ignored (116).

Figure 11:
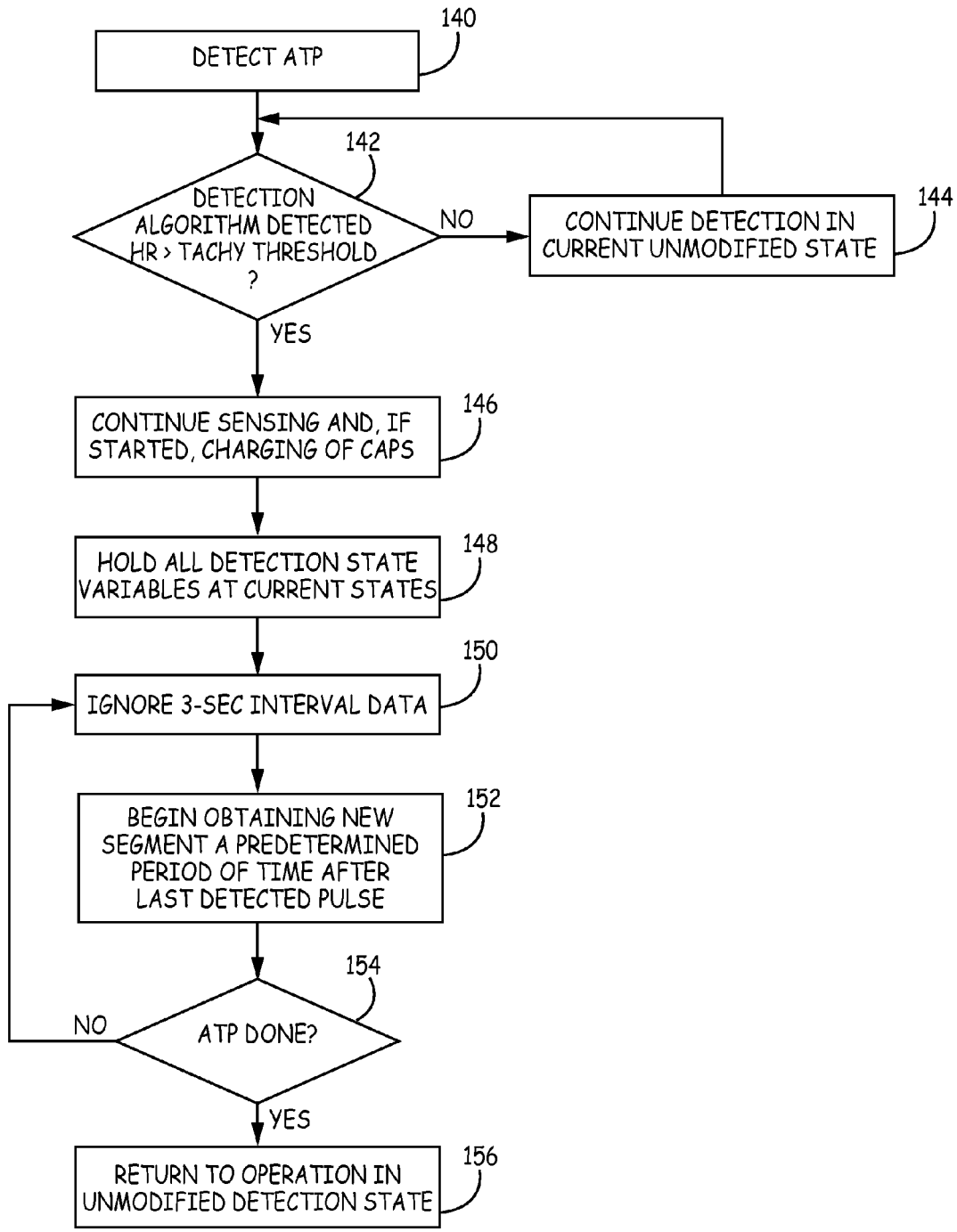
FIG. 11 is a flow diagram illustrating example operation of a control module implementing a modified tachyarrhythmia detection algorithm to account for ATP.

When the estimated cycle length is greater than the minimum cycle length threshold ("YES" branch of block 114), control module 30 compares the estimated cycle length to a second cycle length threshold (118). The second cycle length threshold may be a maximum cycle length that can be confidently classified as ATP. In one example, the second cycle length threshold may be equal to 330 milliseconds. When the estimated cycle length is less than or equal to the second cycle length threshold ("NO" branch of block 118), control module 30 determines the pacing train is ATP and modifies the detection algorithm to account for the presence of ATP (120). FIG. 11 below describes one example of detection modifications made to account for ATP in the sensed electrical signal. In that example, the tachyarrhythmia detection is partially inhibited until ATP has terminated. Such a modification may result in delaying delivery of the shock when ATP is detected. The delay in delivery of the shock may be up to 10 seconds in one example. In another example, the delay in delivery of the shock may be between 3-6 seconds. Other modifications, however, may be made to account for the ATP in the sensed signals. In other examples, additional analysis other than looking at the estimated cycle length may be performed to more confidently conclude that the detected pacing train with the estimated cycle length is ATP. For example, control module 30 may analyze a regularity of the pacing pulse intervals, consistency of the pacing artifact amplitude, consistency of the pacing pulse slew rate, and/or consistency of the pacing pulse polarity. Typically, ATP would be consistent in some, if not all, of these aspects.

Control module 30 continues to analyze the pace spike detect signal and/or the pace artifact detect signal from sensing module 32 to determine whether the pacing train has terminated (122). For instance, control module 30 may detect that the pacing train has terminated when one of two conditions are met: (1) a pacing spike has not been detected for a threshold period of time or (2) the amount of time since detecting the initiation of the pacing train exceeds a threshold amount of time. In one example, control module 30 may detect the end of the pacing train when no pace pulse has been detected on the pace spike detect signal and/or the pace artifact detect signal for at least a multiple of the estimated cycle length of the pacing spikes. The multiple may be any number greater than 2. In one particular example, the multiple may be 2.25 times the estimated cycle length. In other instances, however, control module 30 may utilize a different multiple. Alternatively, control module 30 may detect the end of the pacing train after a particular amount of time has elapsed from initiation of the pacing train. For example, control module 30 may detect the end of the pacing train 3 seconds, 4, seconds, 5 seconds, or other predetermined period of time after initiation of the pacing train. Such a feature sets a maximum duration allowed for detecting ATP.

When control module 30 determines that the pacing train has not terminated ("NO" branch of block 122), control module 30 continues to modify the detection algorithm to account for the presence of ATP (120). When control module 30 determines that the pacing train has terminated ("YES" branch of block 122), control module 30 reverts to the unmodified tachyarrhythmia detection algorithm (124).

Referring back to decision block 118, when the estimated cycle length is greater than the second cycle length threshold ("YES" branch of block 118), control module 30 determines whether the cycle length is greater than a third cycle length threshold (126). In one example, the third cycle length may be equal to 400 ms. When the estimated cycle length is greater than 330 ms and less than 400 ms ("NO" branch of block 126), the pacing train cannot be confidently classified as ATP or fast bradycardia pacing based on the estimated cycle length alone. Control module 30 thus determines whether there is onset leading up to the pacing or shockable rhythm classification leading up to the pacing (130). If the pacing is ATP, it will be preceded by a sudden increase in HR (an "onset"), and likely will have a shockable rhythm classification for segments prior to the pacing. In contrast, if the pacing is fast bradycardia pacing, it will have a slow rise in heart rate over time (i.e., no onset), and likely will have a non-shockable classification for those segments prior to pacing. In other examples, additional analysis other than looking at onset or rhythm classifications leading up to the pacing may be performed to more confidently conclude that the detected pacing train with the estimated cycle length is ATP. For example, control module 30 may analyze a regularity of the pacing pulse intervals, consistency of the pacing artifact amplitude, consistency of the pacing pulse slew rate, and/or consistency of the pacing pulse polarity. Typically, ATP would be consistent in some, if not all, of these aspects.

When control module 30 determines that there is onset leading up to the pacing or shockable rhythm classifications leading up to the pacing ("YES" branch of block 130), control module 30 determines the pacing train is ATP and modifies the detection algorithm to account for the presence of ATP (120). When control module 30 determines that there is no onset leading up to the pacing or non-shockable rhythm classifications leading up to the pacing ("NO" branch of block 130), control module 30 detects fast bradycardia pacing and modifies the detection algorithm to account for the fast bradycardia pacing (132). In one example, a new beat-based morphology consistency discriminator is added to the tachyarrhytmia detection algorithm. Other modifications, however, may be made to account for the fast bradycardia pacing in the sensed signals. Control module 30 continues to operate in the modified beat-based detection algorithm until the cycle length (e.g., heart rate) of the rhythm falls outside of the VT/VF zone.

Returning to decision block 126, when the estimated cycle length is greater than the third cycle length threshold ("YES" branch of block 126), control module 30 compares the estimated cycle length to a fourth cycle length threshold (128). The fourth cycle length threshold may correspond to a maximum fast bradycardia cycle length and may, in one example, be equal to 600 ms. When the estimated cycle length is greater than the fourth cycle length threshold ("YES" branch of block 128), control module operates in the unmodified detection algorithm. When the estimated cycle length is greater than the fourth cycle length threshold ("NO" branch of block 128), control module 30 detects fast bradycardia pacing and modifies the detection algorithm to account for the fast bradycardia pacing (132).

The thresholds used in the example described in FIG. 10 may be used to detect pacing spike trains of a single chamber pacemaker. The thresholds may be different for dual chamber or CRT pacemakers as there may be different timing between paces (e.g., AV delay or VV delay). Other analysis techniques may need to be performed for pacing trains provided to more than one chamber of the heart.

FIG. 11 is a flow diagram illustrating example operation of control module 30 implementing a modified tachyarrhythmia detection algorithm to account for ATP. Initially, control module 30 detects an ATP train (140). In one example, control module 30 may detect the ATP train when an estimate a cycle length of the detected pacing train is between 200-330 ms or between 330-400 ms with heart rate onset of shockable classifications immediately prior to the detection of ATP. However, in other examples, control module may detect ATP pacing using different cycle length ranges.

Control module 30 determines whether the tachyarrhythmia detection algorithm has detected a heart rate that exceeds the tachyarrhythmia detection threshold (142). As described above with respect to FIG. 9, control module 30 operates in non-concerned state 102 in which only the heart rate is analyzed on the selected sensing vectors until the heart rate exceeds the tachyarrhythmia detection threshold, e.g., 180 beats per minute. When the estimated heart rate on both of the sensing vectors does not exceed the tachyarrhythmia detection threshold ("NO" branch of block 142), control module 30 continues to operate in the unmodified non-concerned state 102 (144).

When the tachyarrhythmia detection algorithm detects or previously detected, e.g., prior to detecting the ATP train, that the heart rate exceeds the tachyarrhythmia detection threshold ("YES" branch of block 142), control module 30 is most likely operating in one of the concerned state 104 or the armed state 106 of FIG. 9. As described above with respect to FIG. 9, during the concerned state 104 and the armed state 106, control module 30 is classifying segments of the sensed electrical signal as shockable or non-shockable based on the analysis of the gross morphology of the segments and/or the beat-based morphology within the segments.

Control module 30 continues sensing on the sensing channels and, if operating in the armed state 106, continues charging the defibrillation capacitors (146). Control module 30 holds all detection state variables at current states (148). For example, the buffer maintaining the most recent, e.g., eight, classifications of the segments as shockable and non-shockable will be maintained. Control module 30 will ignore any incomplete segment of the EGM or retrospective segment of the EGM that includes the ATP train (150).

Control module 30 begins a new segment (e.g., 3-second segment) a predetermined period of time after the last detected pace pulse (152). For example, control module 30 may begin a new 3-second segment 330 ms after the last detected pace pulse. In other instances, control module 30 may begin the new segment (e.g., 3-second segment) of the signal after the last detected pace pulse based on the estimated cycle length. Control module 30 determines whether the ATP train has terminated (154). As described above, for example, control module 30 may detect that the pacing train has terminated when one of two conditions are met: (1) a pacing pulse has not been detected for a threshold period of time (e.g., 2.25× the estimated cycle length or some predetermined threshold) or (2) the amount of time since detecting the initiation of the pacing train exceeds a threshold amount of time (e.g., 5 seconds). Note that the criteria for detecting the end of a pacing train will be met after initiation of obtaining the new 3-second morphology segment. In other words, the start of a possible 3 second morphology analysis window may be initiated before the end of a pacing train is detected.

When the end of the pacing train is not detected ("NO" branch of block 154), control module 30 ignores the segment of data and a new possible morphology segment will again be initiated a predetermined period of time after the most recently detected pacing pulse (150, 152). In another example, control module 30 may not obtain the morphology segment (e.g., 3-second segment) until after detecting the ATP has terminated in block 154. When control module 30 determines that the ATP train has terminated ("YES" branch of block 154), control module 30 returns to normal detection operation and performs the morphology analysis of the new morphology segment to determine whether the segment is shockable or non-shockable (156). Control module 30 will therefore update the detection state as if it were contiguous with the pre-ATP analysis. As a result, the modification to the tachyarrhythmia detection algorithm will result in delaying delivery of the shock when ATP is detected. The delay in delivery of the shock may be up to 10 seconds in one example. In another example, the delay in delivery of the shock may be between 3-6 seconds.

Figure 12:
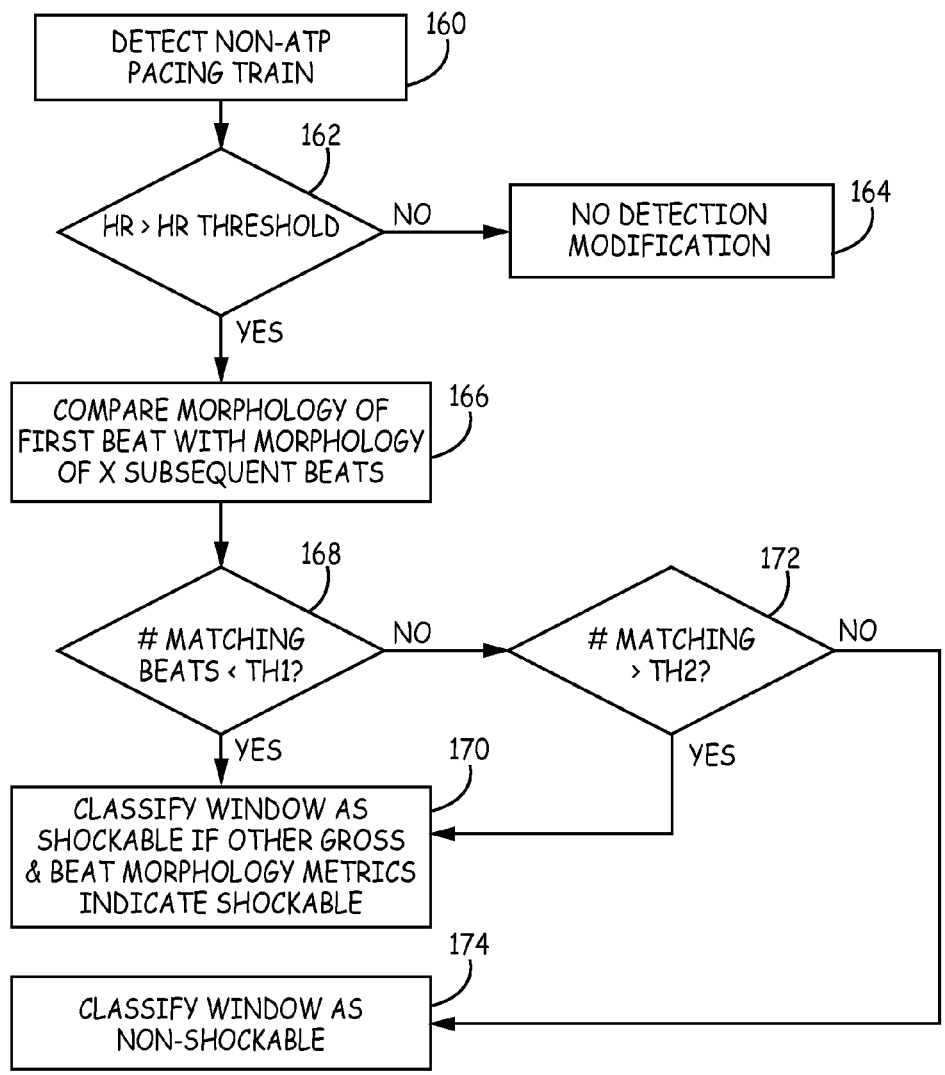
FIG. 12 is a flow diagram illustrating example operation of a control module modifying a tachyarrhythmia detection algorithm to account for fast bradycardia pacing.

FIG. 12 is a flow diagram illustrating example operation of control module 30 modifying a tachyarrhythmia detection algorithm to account for fast bradycardia pacing. Initially, control module 30 detects a fast bradycardia pacing train (160). In one example, control module 30 may estimate a cycle length of a detected pacing train and detect the fast bradycardia pacing train when the estimated cycle length of the detected pacing train is greater than 400 ms, as described above with respect to FIG. 10. However, in other examples, control module may detect fast bradycardia pacing using a different cycle length threshold or other technique.

Control module 30 determines whether the heart rate as sensed on both of the sensing vectors is above a tachyarrhythmia heart rate threshold, e.g., 180 beats per minute (162). When control module 30 determines that the heart rate is not above the tachyarrhythmia heart rate threshold ("NO" branch of block 162), control module 30 does not make any tachyarrhythmia detection modifications (164). When control module 30 determines that the heart rate is above the threshold heart rate ("YES" branch of block 162), control module 30 implements an additional beat-based morphology analysis to monitor the consistency of the morphology. One example scenario that may result in a shockable classification when no shock is necessary is when the paced evoked response results in double counting because of the wide QRS and large T-waves. The ECG morphology surrounding such a scenario would be an A-B-A-B pattern caused by the consistent oversensing and if the pacing pulses lead to consistent capture.

To identify this scenario, or other scenarios that may cause inappropriate shock classifications, control module 30 compares a morphology of a first sensed event within the current segment with a morphology of a predetermined number of subsequent sensed events within the segment and classify each of the comparisons as a match or non-match (166). Each sensed event or beat may be classified as matching when a matching score that is greater than or equal to a threshold, e.g., 60%, otherwise the beat is classified as non-matching. In other instances, control module 30 may compare a morphology of first sensed event after detection of ATP with the morphology of the subsequent sensed events within the segments and classify each of the comparisons as a match or non-match. Whereas the beat-based morphology analysis performed in the concerned state 104 and the armed state 106 described above in FIG. 9 compares the morphology of the beat window to a predetermined template of an intrinsic heart rate morphology, the additional beat-based morphology consistency discriminator compares the morphology of the first sensed event of the tachyarrhythmia with morphology of a predetermined number of subsequent sensed events. In one example, the predetermined number of subsequent sensed events is equal to 11. However, the predetermined number may be greater than or less than 11.

Control module 30 determines whether the number of subsequent sensed events having morphologies that match the morphology of the first sensed event of the segment is less than a first threshold (168). In one example, the first threshold may be equal to 3 when the predetermined number of subsequent sensed events is equal to 11. However, the first threshold may be equal to other values, particularly when the predetermined number of subsequent sensed events is greater than or less than 11. When control module 30 determines that the number of the subsequent sensed events having morphologies that match the morphology of the first sensed event of the segment is less than the first threshold ("YES" branch of block 168), control module 30 characterizes the segment as shockable if the other gross and beat-based morphology analyses indicate shockable (170). This may occur, for example, when the tachyarrhythmia is VF or polymorphic VT.

When control module 30 determines that the number of the subsequent sensed events having morphologies that match the morphology of the first sensed event of the segment is greater than or equal to the first threshold ("NO" branch of block 168), control module 30 determines whether the number of subsequent sensed events having morphologies that match the morphology of the first sensed event of the segment is greater than a second threshold (172). In one example, the second threshold may be equal to 7 when the predetermined number of subsequent sensed events is equal to 11. However, the second threshold may be equal to other values, particularly when the predetermined number of subsequent sensed events is greater than or less than 11.

When control module 30 determines that the number of the subsequent sensed events having morphologies that match the morphology of the first sensed event of the segment is greater than the second threshold ("YES" branch of block 172), control module 30 characterizes the segment as shockable (170) if the other gross and beat-based morphology analyses indicate shockable. This may occur, for example, when the tachyarrhythmia is a monomorphic VT. When control module 30 determines that the number of the subsequent sensed events having morphologies that match the morphology of the first sensed event of the tachyarrhythmia (or segment) is less than or equal to the second threshold ("NO" branch of block 172), control module 30 characterizes the tachyarrhythmia (or segment) as non-shockable regardless of whether the other gross and beat-based morphology analyses indicate shockable (174). This may occur, for example, when the detection of the tachyarrhythmia is likely a result of oversensing.

Figure 13:
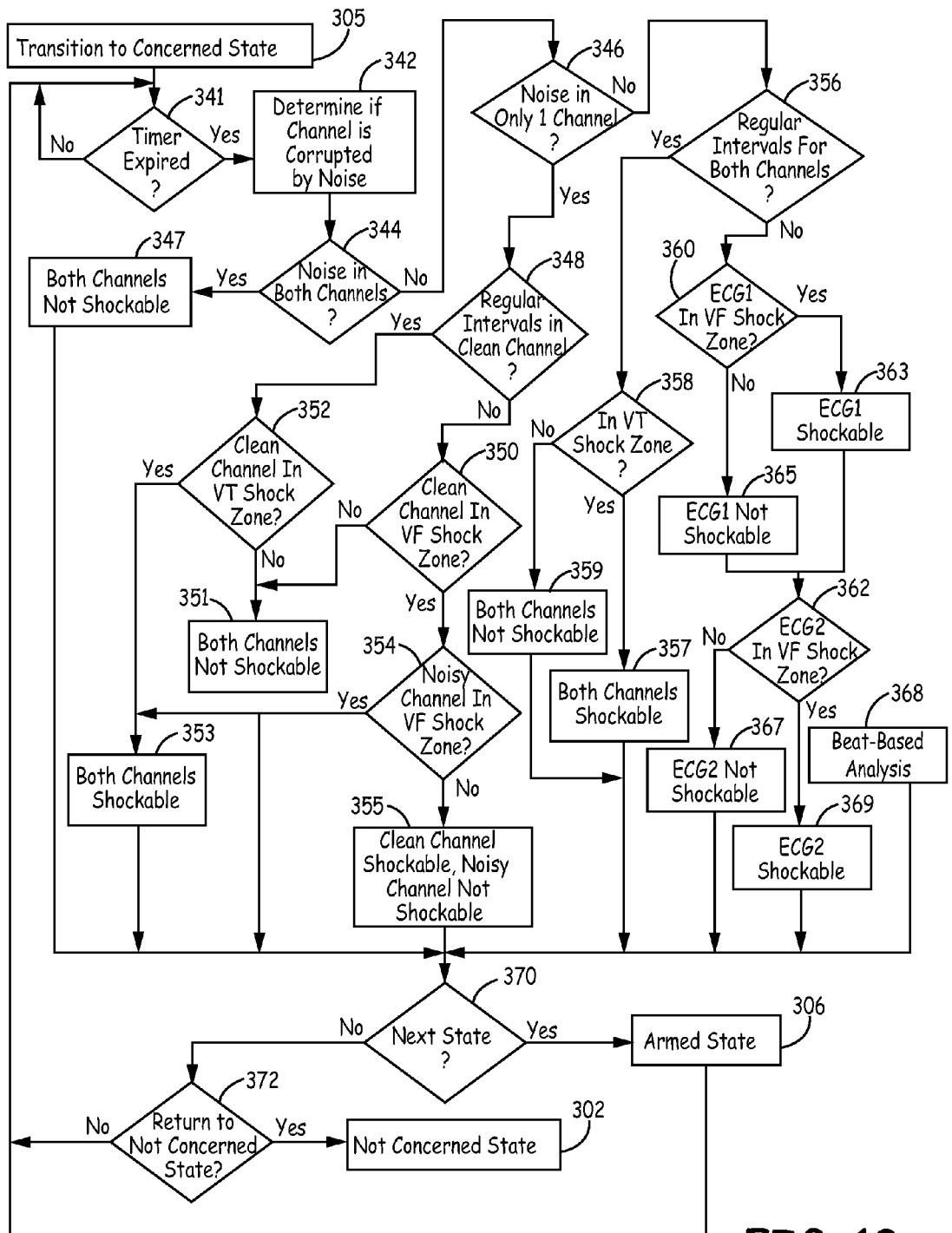
FIG. 13 is a flowchart illustrating an example implementation of the concerned state 104 of FIG. 9.

FIG. 13 is a flowchart illustrating an example implementation of the concerned state 104 of FIG. 9. Initially, control module 30 transitions to the concerned state 104 (305), e.g., in response to the heart rate on one or both of the sensing vectors is above the tachyarrhythmia heart rate threshold. Control module 30 may store ECG data on two ECG channels (ECG1 and ECG2) until a timer expires to obtain a fixed size segment (341). As described in one example above, the timer may be equal to three seconds such that when the time expires a first 3-second segment of data is obtained on ECG1 and ECG2. In this manner, processing is triggered in the concerned state 104 by a predetermined timeout (e.g., 3-second timeout), rather than by the sensing of an R-wave as in the not concerned state 102.

It is understood that while the processing is described as being triggered over a three second period, other times periods for the processing time utilized when in the concerned state 104 may be chosen, but should preferably be within a range of 0.5 to 10 seconds. As a result, although sensing of individual R-waves continues to occur in both channels ECG1 and ECG2 when in the concerned state 104, and the buffer of 12 R-R intervals continues to be updated, the opportunities for changing from the concerned state 104 to another state and the estimates of heart rate only occur once the three-second timer expires. Upon initial entry to the concerned state 104, it is advantageous to process the most recent three-seconds of ECG data, i.e., ECG data for the three seconds leading up to the transition to the concerned state 104. This requires a continuous circular buffering of the most recent three seconds of ECG data even while in the not concerned state 102.

Once the time interval has expired, YES in Block 341, morphology characteristics of the signal during the three second time interval for each channel are utilized to determine whether the signals are likely corrupted by noise artifacts and to characterize the morphology of the signal as "shockable" or "not shockable". For example, using the signals associated with the three second time interval as an example, a determination is made for each channel ECG1 and ECG 2 as to whether the channel is likely corrupted by noise (342), and a determination is then made as to whether both channels ECG1 and ECG2 are corrupted by noise (344).

Figure 14:
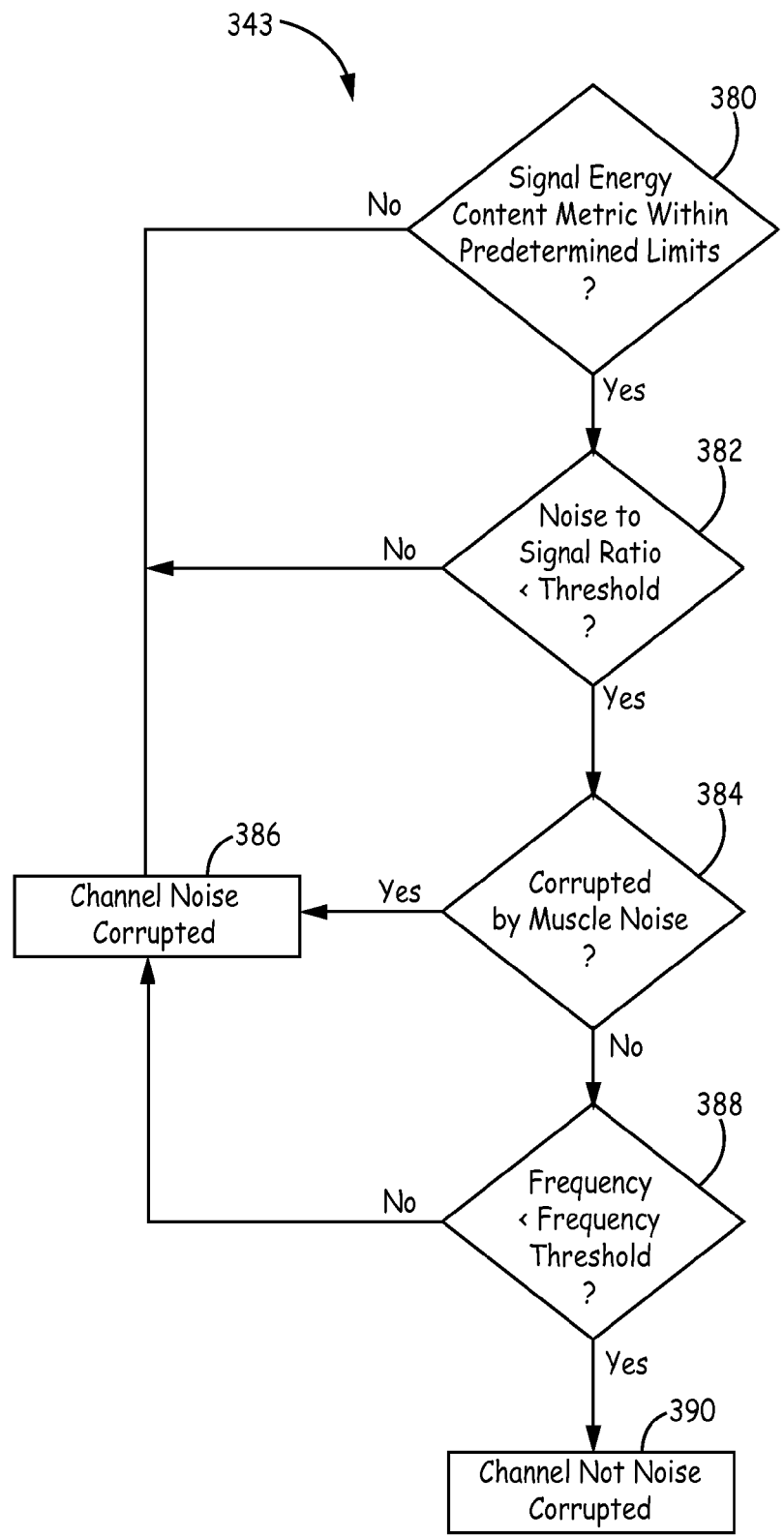
FIG. 14 is a flowchart of a method of determining noise according to one example.

FIG. 14 is a flowchart of a method of determining noise according to one example. As illustrated in FIG. 14, the determination as to whether the signal associated with each of the channels ECG1 and ECG2 is likely corrupted by noise, Block 342 of FIG. 13, includes multiple sequential noise tests that are performed on each channel ECG1 and ECG2. During a first noise test, for example, a determination is made as to whether a metric of signal energy content of the signal for the channel is within predetermined limits, Block 380. For example, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

Once the mean rectified amplitude is calculated, a determination is made as to whether the mean rectified amplitude is between an upper average amplitude limit and a lower average amplitude limit, the lower average amplitude limit being associated with asystole episodes without artifact and the upper average amplitude limit being associated with a value greater than what would be associated with ventricular tachycardia and ventricular fibrillation events. According to an embodiment of the present disclosure, the upper average amplitude limit is set as 1.5 mV, and the lower average amplitude limit is set as 0.013 mV. While the metric of signal energy content is described above as the mean rectified amplitude, it is understood that other signal of energy contents could be utilized.

If the determined mean rectified amplitude is not between the upper average amplitude limit and the lower average amplitude limit, the three second segment for that channel is identified as being likely corrupted with noise, Block 386, and no further noise tests are initiated for that channel's segment.

If the determined mean rectified amplitude is located between the upper average amplitude limit and the lower average amplitude limit, a noise to signal ratio is calculated and a determination is made as to whether the noise to signal ratio is less than a predetermined noise to signal threshold, Block 382. For example, the amplitude of each sample associated with the three second window is determined, resulting in N raw sample amplitudes. The raw signal is lowpass filtered, resulting in L lowpass sample amplitudes. The raw mean rectified amplitude is determined as the average of the absolute values of the raw sample amplitudes. The lowpass mean rectified amplitude is determined as the average of the absolute values of the lowpass sample amplitudes. Next, a highpass mean rectified amplitude is then calculated as the difference between the raw mean rectified amplitude and the lowpass mean rectified amplitude. The noise to signal ratio is then determined as the ratio of the highpass mean rectified amplitude to the lowpass mean rectified amplitude. If the noise to signal ratio is greater than a predetermined threshold, such as 0.0703, for example, the three second segment for that channel is identified as being likely corrupted with noise, Block 386, and no further noise tests are initiated for the segment.

If the noise to signal ratio is less than or equal to the predetermined threshold, a determination is made as to whether the signal is corrupted by muscle noise, Block 384. According to an embodiment of the present disclosure, the determination as to whether the signal is corrupted by muscle noise is made by determining whether the signal includes a predetermined number of signal inflections indicative of the likelihood of the signal being corrupted by muscle noise, using a muscle noise pulse count that is calculated to quantify the number of signal inflections in the three second interval for each channel ECG1 and ECG2. The presence of a significant number of inflections is likely indicative of muscle noise.

Figure 15A:
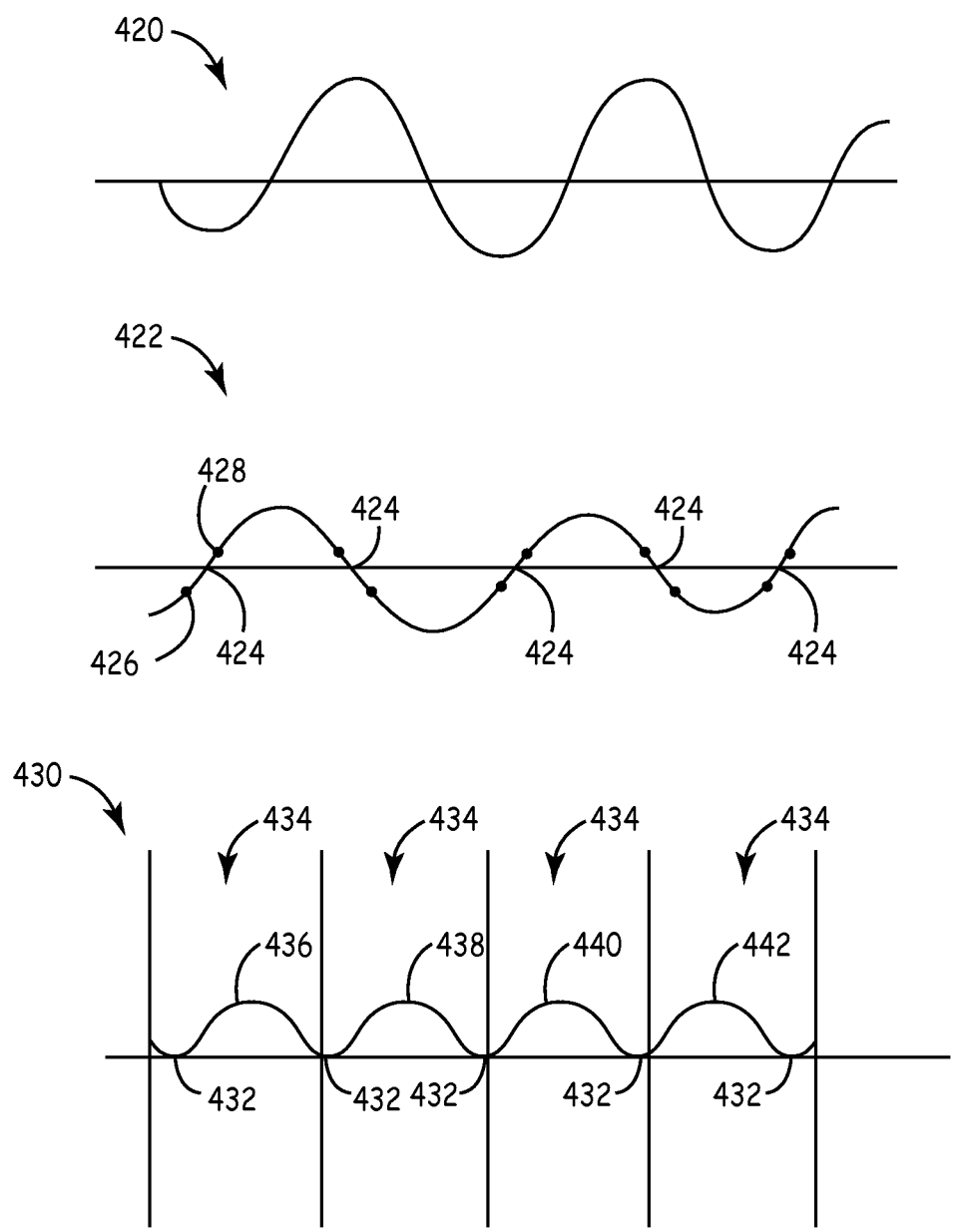
FIG. 15A is a graphical representation of a determination of whether a signal is corrupted by muscle noise according to an embodiment of the present disclosure.
Figure 15B:
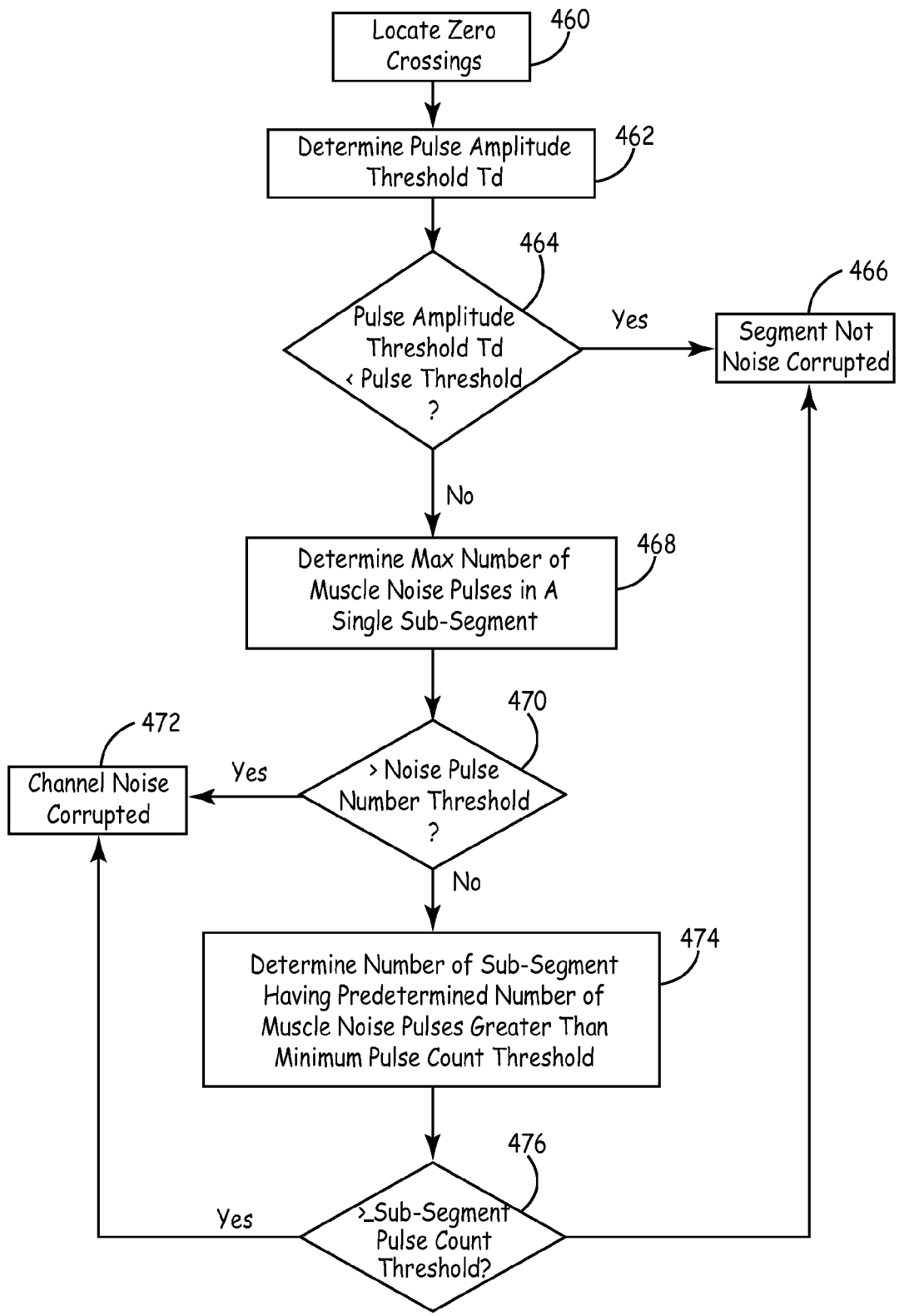
FIG. 15B is a flowchart of a method of determining whether a signal is corrupted by muscle noise according to an embodiment of the present disclosure.

FIG. 15A is a graphical representation of a determination of whether a signal is corrupted by muscle noise according to an embodiment of the present disclosure. FIG. 15B is a flowchart of a method of determining whether a signal is corrupted by muscle noise according to an embodiment of the present disclosure. For example, as illustrated in FIGS. 15A and 15B, in order to determine a muscle noise count for the three second interval, the raw signal 420 is applied to a first order derivative filter to obtain a derivative signal 422, and all of the zero-crossings 424 in the derivative signal 422 are located, Block 460. A data pair corresponding to the data points immediately prior to and subsequent to the zero crossings 424, points 426 and 428 respectively, for each crossing is obtained. The value of the data point in each data pair with smaller absolute value is zeroed in order to allow a clear demarcation of each pulse when a rectified signal 430 is derived from the derivative signal 422 with zeroed zero-crossing points 432.

A pulse amplitude threshold Td, for determining whether the identified inflection is of a significant amplitude to be identified as being associated with muscle noise, is determined, Block 462, by dividing the rectified signal from the three second segment into equal sub-segments 434, estimating a local maximum amplitude 436-442 for each of the sub-segments 434, and determining whether the local amplitudes 436-442 are less than a portion of the maximum amplitude, which is maximum amplitude 440 in the example of FIG. 15A, for the whole three second segment. If the local maximum amplitude is less than the portion of the maximum amplitude for the whole three second segment, the local maximum amplitude is replaced by the maximum for the whole three second segment for the sub-segment corresponding to that local maximum amplitude.

It is understood that while only two or less zero-crossing points are shown as being located within the sub-segments in the illustration of FIG. 15A for the sake of simplicity, in fact each of the sub-segments 434, which have a length of approximately 750 milliseconds, will contain many inflections, such as every 25 milliseconds, for example.

According to an embodiment of the present disclosure, the three second segment is divided into four sub-segments and the local maximum amplitudes are replaced by the maximum amplitude for the whole segment if the local maximum amplitude is less than one fifth of the maximum amplitude for the whole segment. Once the determination of whether to replace the local maximum amplitudes for each of the sub-segments with the maximum amplitude for the whole segment is completed, the pulse amplitude threshold Td for the segment is set equal to a predetermined fraction of the mean of the local maximum amplitudes for each of the sub-segments. According to an embodiment of the present disclosure, the pulse amplitude threshold Td for the three second segment is set equal to one sixth of the mean of the local maximum amplitudes 436-440.

Once the pulse amplitude threshold Td has been determined, the inflections associated with the signal for the three second segment is classified as being of significant level to be likely indicative of noise by determining whether the pulse amplitude threshold Td is less than a pulse threshold, Block 464. According to an embodiment of the present disclosure, the pulse threshold is set as 1 microvolt. If the pulse amplitude threshold Td is less than the pulse threshold, the signal strength is too small for a determination of muscle noise, and therefore the signal is determined to be not likely corrupted by noise and therefore the channel is determined to be not noise corrupted, Block 466.

If the pulse amplitude threshold Td is greater than or equal to the pulse threshold, the three second segment is divided into twelve sub-segments of 250 ms window length, the number of muscle noise pulses in each sub-segment is counted, and both the sub-segment having the maximum number of muscle noise pulses and the number of sub-segments having 6 or more muscle noise pulses that are greater than a predetermined minimum threshold is determined. Muscle noise is determined to be present in the signal if either the maximum number of muscle noise pulses in a single sub-segment is greater than a noise pulse number threshold or the number of sub-segments of the twelve sub-segments having 6 or more muscle noise pulses greater than the minimum threshold is greater than or equal to a sub-segment pulse count threshold. According to an embodiment of the present disclosure, the noise pulse number threshold is set equal to eight and the sub-segment pulse count threshold is set equal to three.

For example, if the pulse amplitude threshold Td is greater than or equal to the pulse threshold, No in Block 464, the maximum number of muscle noise counts in a single sub-segment is determined, Block 468. If the maximum number of muscle noise counts is greater than the noise pulse number threshold, Yes in Block 470, the channel is determined to be noise corrupted, Block 472. If the maximum number of muscle noise counts for the channel is less than or equal to the noise pulse number threshold, No in Block 470, the number of sub-segments of the twelve sub-segments having 6 or more muscle noise pulses greater than the minimum threshold is determined, Block 474, and if the number is greater than or equal to a sub-segment pulse count threshold, Yes in Block 476, the channel is determined to be noise corrupted, Block 472. If the number is less than the sub-segment pulse count threshold, No in Block 476, the channel is determined not to be noise corrupted, Block 466.

Figure 15C:
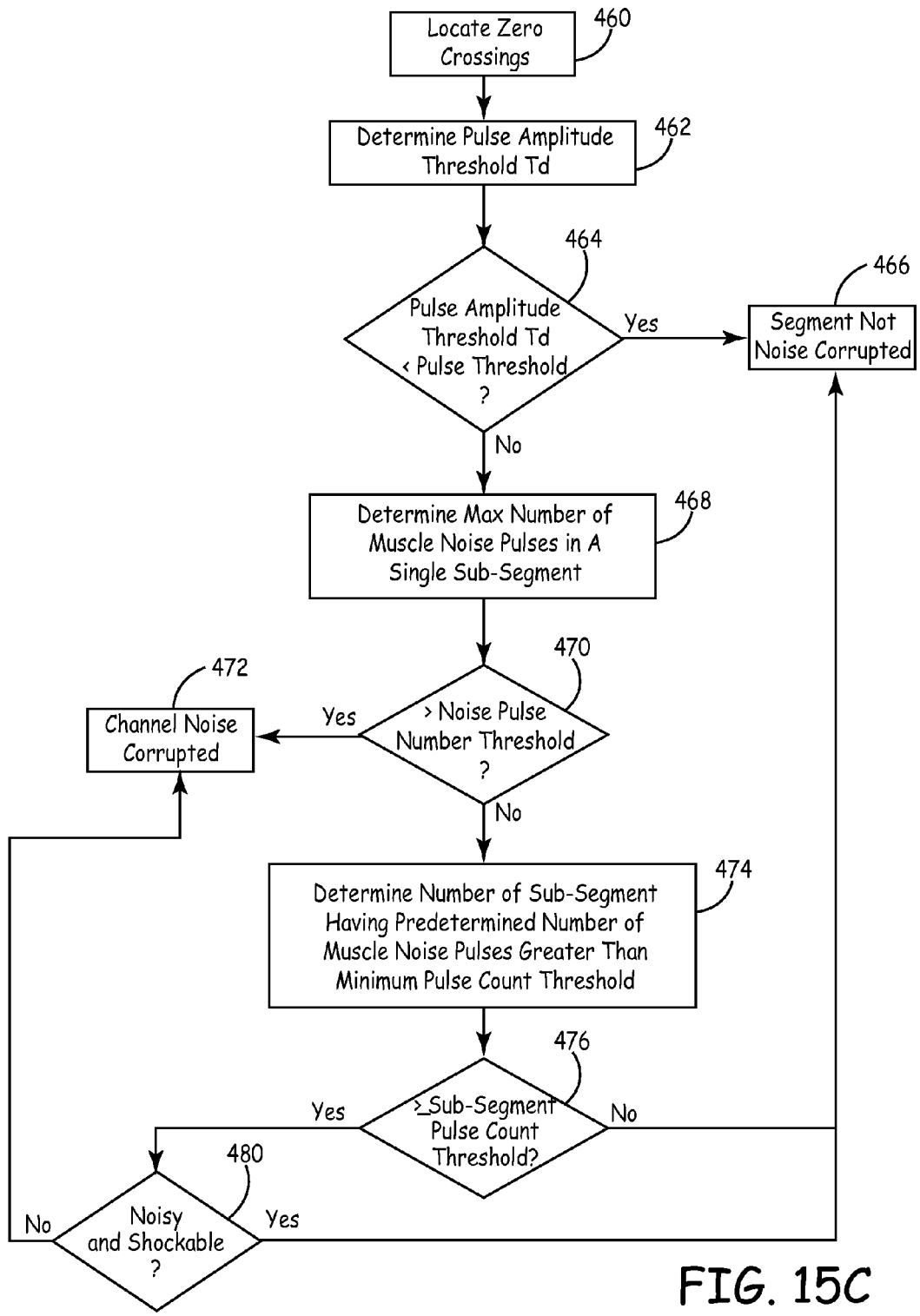
FIG. 15C is a flowchart of a method of determining whether a signal is corrupted by muscle noise according to an embodiment of the present disclosure.

FIG. 15C is a flowchart of a method of determining whether a signal is corrupted by muscle noise according to an embodiment of the present disclosure. Since muscle noise can be present during an episode of ventricular tachycardia, the width of the overall signal pulse waveform is determined in order to distinguish between signals that are determined likely to be purely noise related and signals that are both shockable events and determined to include noise. Therefore, as illustrated in FIG. 15C, according to an embodiment of the present disclosure, once muscle noise is determined to be present as a result of the muscle noise pulse count being satisfied, No in Block 470 and Yes in Block 476, a determination is made as to whether the signal is both noise corrupted and shockable, Block 480.

According to an embodiment of the present disclosure, the determination in Block 480 as to whether the signal is both noisy and shockable is made, for example, by dividing the rectified signal, having 768 data points, into four sub-segments and determining a maximum amplitude for each of the four sub-segments by determining whether a maximum amplitude for the sub-segment is less than a portion of the maximum amplitude for the entire rectified signal in the three second segment. For example, a determination is made for each sub-segment as to whether the maximum amplitude for the sub-segment is less than one fourth of the maximum amplitude for the entire rectified signal. If less than a portion of the maximum amplitude for the entire rectified signal in the three second segment, the maximum amplitude for the sub-segment is set equal to the maximum amplitude for the entire rectified signal.

A mean rectified amplitude for each of the sub-segments is determined by dividing the sum of the rectified amplitudes for the sub-segment by the number of samples in the sub-segment, i.e., 768÷4. Then the normalized mean rectified amplitude for each sub-segment is determined by dividing the mean rectified amplitude for each of the sub-segments by the peak amplitude for the sub-segment. The normalized mean rectified amplitude for the three second segment is then determined as the sum of the normalized mean rectified amplitudes for each sub-segment divided by the number of sub-segments, i.e., four.

Therefore, once muscle noise is suspected as a result of the determination of the muscle noise pulse count, the determination of Block 480 based on whether the normalized mean rectified amplitude for the three second segment is greater than a predetermined threshold for identifying signals that, despite being indicative of a likelihood of being associated with noise, nevertheless are associated with a shockable event. For example, according to an embodiment of the present disclosure, a determination is made as to whether the normalized mean rectified amplitude for the three second segment is greater than 18 microvolts. If the normalized mean rectified amplitude for the three second segment is less than or equal to the predetermined threshold, the channel is likely corrupted by muscle noise and not shockable, No in Block 480, and is therefore identified as being corrupted by noise, Block 472. If the normalized mean rectified amplitude for the three second segment is greater than the predetermined threshold, the channel is determined to be likely corrupted by muscle noise and shockable, Yes in Block 480, and is therefore identified as not to be likely corrupted by muscle noise, Block 478.

Returning to FIG. 14, when the signal is determined to be not likely corrupted by muscle noise, a determination is made as to whether the mean frequency of the signal associated with the channel is less than a predetermined mean frequency threshold, Block 388, such as 11 Hz for example. The mean frequency of the signal during the 3 second segment for each channel ECG 1 and ECG2 is generated, for example, by calculating the ratio of the mean absolute amplitude of the first derivative of the 3 second segment to the mean absolute amplitude of the 3 second segment, multiplied by a constant scaling factor. If the mean frequency is determined to be greater than or equal to the predetermined mean frequency threshold, No in Block 388, the three second segment for that channel is identified as being likely corrupted with noise, Block 386. If the mean frequency is determined to be less than the predetermined mean frequency threshold, Yes in Block 388, the three second segment for that channel is identified as being not noise corrupted, Block 390.

According to an embodiment of the present disclosure, since the mean spectral frequency tends to be low for true ventricular fibrillation events, moderate for organized rhythms such as sinus rhythm and supraventricular tachycardia, for example, and high during asystole and noise, the determination in Block 388 includes determining whether the mean frequency is less than a predetermined upper mean frequency threshold, such as 11 Hz (i.e., mean period T of approximately 91 milliseconds) for example, and whether the mean frequency is less than a predetermined lower mean frequency, such as 3 Hz for example. If the mean frequency is below a second, lower threshold, such as 3 Hz, for example, the signal is also rejected as noise and no further noise tests are initiated. This comparison of the mean frequency to a second lower threshold is intended to identify instances of oversensing, resulting in appropriate transition to the concerned state. If the mean frequency of the signal is less than 3 Hz, it is generally not possible for the heart rate to be greater than 180 beats per minute. In practice, it may be advantageous to set the lower frequency threshold equal to the programmed VT/VF detection rate, which is typically approximately 3 Hz.

Therefore, in the determination of Block 388, if the mean frequency is determined to be either greater than or equal to the predetermined upper mean frequency threshold or less than the lower threshold, the three second segment for that channel is identified as being likely corrupted with noise, Block 386. If the mean frequency is determined to be both less than the predetermined upper mean frequency threshold and greater than the lower threshold, the three second segment for that channel is identified as not being noise corrupted, Block 390.

Returning to FIG. 13, once the determination as to whether the channels ECG1 and ECG2 are corrupted by noise is made, Block 342, a determination is made as to whether both channels are determined to be noise corrupted, Block 344. If the signal associated with both channels ECG1 and ECG2 is determined to likely be corrupted by noise, both channels are classified as being not shockable, Block 347, and therefore a buffer for each channel ECG1 and ECG 2 containing the last three classifications of the channel is updated accordingly and the process is repeated for the next three-second windows. If both channels ECG1 and ECG2 are not determined to be likely corrupted by noise, No in Block 344, the device distinguishes between either one of the channels being not corrupted by noise or both channels being not corrupted by noise by determining whether noise was determined to be likely in only one of the two channels ECG1 and ECG2, Block 346.

If noise was likely in only one of the two channels, a determination is made whether the signal for the channel not corrupted by noise, i.e., the clean channel, is more likely associated with a VT event or with a VF event by determining, for example, whether the signal for that channel includes R-R intervals that are regular and the channel can be therefore classified as being relatively stable, Block 348. If the R-R intervals are determined not to be relatively stable, NO in Block 348, the signal for that channel is identified as likely being associated with VF, which is then verified by determining whether the signal is in a VF shock zone, Block 350, described below. If R-R intervals for that channel are determined to be stable, YES in Block 348, the signal is identified as likely being associated with VT, which is then verified by determining whether the signal is in a VT shock zone, Block 352, described below.

If noise was not likely for both of the channels, No in Block 346, i.e., both channels are determined to be clean channels, a determination is made whether the signal for both channels is more likely associated with a VT event or with a VF event by determining whether the signal for both channels includes R-R intervals that are regular and can be therefore classified as being relatively stable, Block 356. The determination in Block 356 of whether the R-R intervals are determined to be relatively stable may be made using the method described in U.S. Pat. No. 7,894,894 to Stadler et al., incorporated herein by reference in it's entirety. If the R-R intervals are determined not to be relatively stable, NO in Block 356, the signal for both channels is identified as likely being associated with VF, which is then verified by determining whether the signal for each channel is in a VF shock zone, Block 360, described below. If R-R intervals for both channels are determined to be stable, YES in Block 356, the signal is identified as likely being associated with VT, which is then verified by determining, based on both channels, whether the signal is in a VT shock zone, Block 358.

Figure 16:
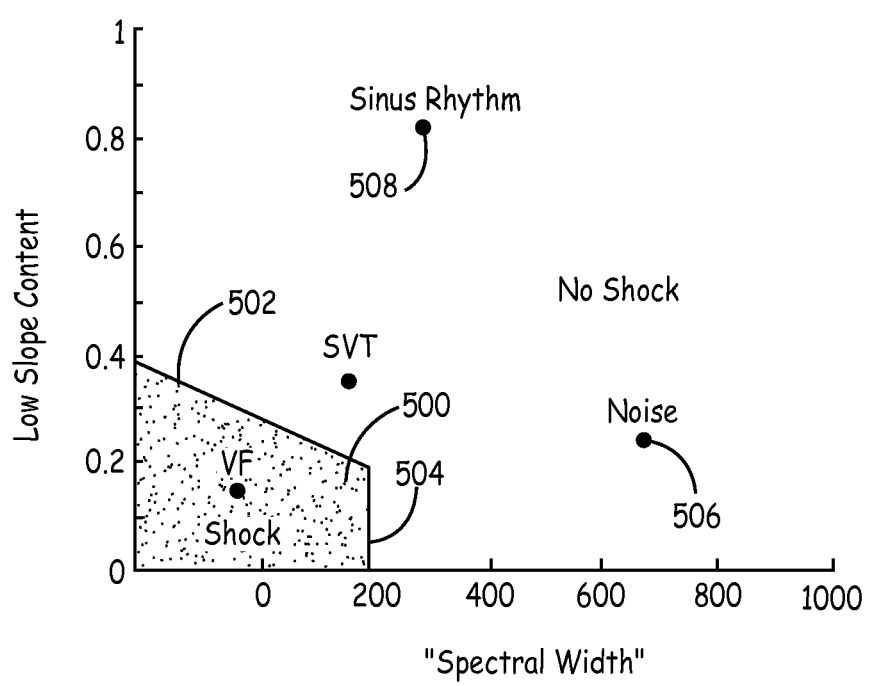
FIG. 16 is a graphical representation of a VF shock zone according to an embodiment of the present disclosure.

FIG. 16 is a graphical representation of a VF shock zone according to an embodiment of the present disclosure. As illustrated in FIG. 16, a VF shock zone 500 is defined for each channel ECG1 and ECG2 based on the relationship between the calculated low slope content and the spectral width associated with the channel. For example, the shock zone is defined by a first boundary 502 associated with the low slope content set for by the equation:

$$\text{Low slope content} = -0.0013 \times \text{spectral width} + 0.415 \quad (1)$$

and a second boundary 504 associated with the spectral width set forth by the equation:

$$\text{spectral width} = 200 \quad (2)$$

The low slope content metric is calculated as the ratio of the number of data points with low slope to the total number of samples in the 3-second segment. For example, according to an embodiment of the present disclosure, the difference between successive ECG samples is determined as an approximation of the first derivative (i.e, the slope) of the ECG signal. In particular, the raw signal for each channel is applied to a first order derivative filter to obtain a derivative signal for the three-second segment. The derivative signal is then rectified, divided into four equal sub-segments, and the largest absolute slope is estimated for each of the four sub-segments.

A determination is made as to whether the largest absolute slopes are less than a portion of the overall largest absolute slope for the whole three-second segment, such as one-fifth of the overall absolute slope, for example. If the largest absolute slope is less than the portion of the overall slope, then the slope value for that sub-segment is set equal to the overall largest absolute slope. If the largest absolute slope is not less than the portion of the overall slope, then the slope value for that sub-segment is set equal to the determined largest absolute slope for the sub-segment.

Once the slope value for each of the sub-segments has been determined and updated by being set equal to the largest slope for the three second segment, if necessary, the average of the four slopes is calculated and divided by a predetermined factor, such as 16 for example, to obtain a low slope threshold. The low slope content is then obtained by determining the number of sample points in the three-second segment having an absolute slope less than or equal to the low slope threshold.

According to an embodiment of the present disclosure, if, during the determination of the low slope threshold, the low slope threshold is a fraction, rather than a whole number, a correction is made to the low slope content to add a corresponding fraction of the samples. For example, if the threshold is determined to be 4.5, then the low slope content is the number of sample points having an absolute slope less than or equal to 4 plus one half of the number of sample points with slope equal to 5.

The spectral width metric, which corresponds to an estimate of the spectral width of the signal for the three-second segment associated with each channel ECG1 and ECG2, is defined, for example, as the difference between the mean frequency and the fundamental frequency of the signal. According to an embodiment of the present disclosure, the spectral width metric is calculated by determining the difference between the most recent estimate of the RR-cycle length and the mean spectral period of the signal for that channel. As is known in the art, the mean spectral period is the inverse of the mean spectral frequency.

As can be seen in FIG. 16, since noise 506 tends to have a relatively higher spectral width, and normal sinus rhythm 508 tends to have a relatively higher low slope content relative to VF, both noise 506 and normal sinus rhythm 508 would be located outside the VF shock zone 500.

A determination is made for each channel ECG1 and ECG2 as to whether the low slope content for that channel is less than both the first boundary 502 and the spectral width is less than the second boundary 504, i.e., the low slope content is less than −0.0013×spectral width+0.415, and the spectral width is less than 200. For example, once the event is determined to be associated with VF, i.e., the intervals for both channels are determined to be irregular, No in Block 356, a determination is made that channel ECG1 is in the VF shock zone, Yes in Block 360, if, for channel ECG1, both the low slope content is less than the first boundary 502 and the spectral width is less than the second boundary 504. The three second segment for that channel ECG1 is then determined to be shockable, Block 363 and the associated buffer for that channel is updated accordingly. If either the low slope content for the channel is not less than the first boundary 502 or the spectral width is not less than the second boundary, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, both the low slope content is less than the first boundary 502 and the spectral width is less than the second boundary 504. The three second segment for that channel ECG2 is then determined to be shockable, Block 369 and the associated buffer for that channel is updated accordingly. If either the low slope content for the channel is not less than the first boundary 502 or the spectral width is not less than the second boundary, the channel ECG2 is determined not to be in the VF shock zone, No in Block 362, the three second segment for that channel ECG2 is then determined to be not shockable, Block 367, and the associated buffer is updated accordingly.

Figure 17A:
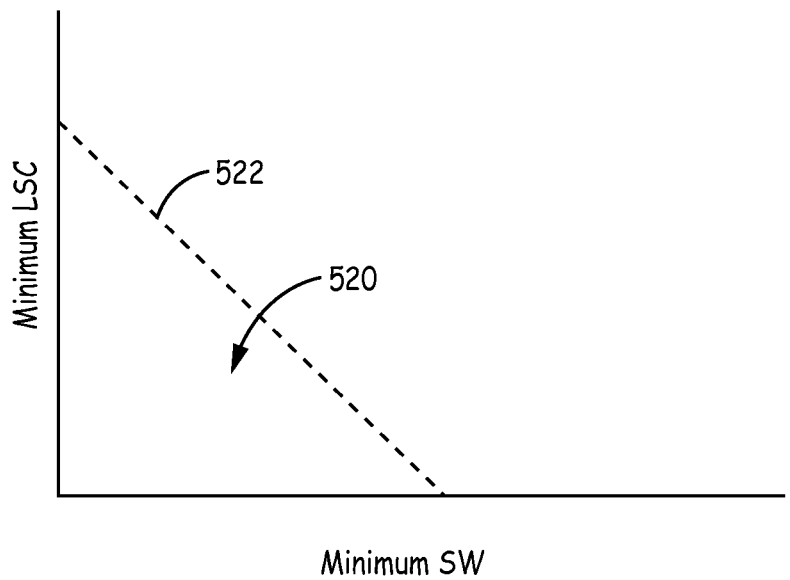
FIGS. 17A and 17B are graphical representations of the determination of whether an event is within a shock zone according to an embodiment of the present disclosure.
Figure 17B:
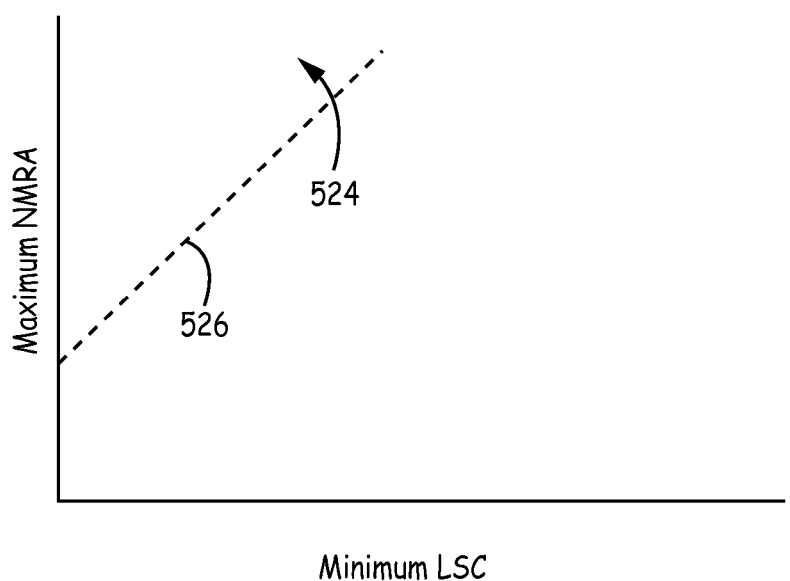

FIGS. 17A and 17B are graphical representations of the determination of whether an event is within a shock zone according to an embodiment of the present disclosure. During the determination of whether the event is within the VT shock zone, Block 358 of FIG. 13, the low slope content and the spectral width is determined for each channel ECG1 and ECG2, as described above in reference to determining the VF shock zone. A determination is made as to which channel of the two signal channels ECG1 and ECG2 contains the minimum low slope content and which channel of the two signal channels ECG 1 and ECG2 contains the minimum spectral width. A first VT shock zone 520 is defined based on the relationship between the low slope content associated with the channel determined to have the minimum low slope content and the spectral width associated with the channel determined to have the minimum spectral width. For example, according to an embodiment of the present disclosure, the first VT shock zone 520 is defined by a boundary 522 associated with the minimum low slope content and the minimum spectral width set forth by the equation:

$$LSC=-0.004 \times SW+0.93 \qquad (3)$$

A second VT shock zone 524 is defined based on the relationship between the low slope content associated with the channel determined to have the minimum low slope content and the normalized mean rectified amplitude associated with the channel determined to have the maximum normalized mean rectified amplitude. In order to determine the normalized mean rectified amplitudes for the two channels ECG1 and ECG2 utilized during the VT shock zone test, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

According to an embodiment of the present disclosure, for example, the second VT shock zone 524 is defined by a second boundary 526 associated with the relationship between the minimum low slope count and the maximum normalized mean rectified amplitude set forth by the equation:

$$NMRA=68 \times LSC+8.16 \qquad (4)$$

If both the minimum low slope count is less than the first boundary 522, i.e., $-0.004 \times$minimum spectral width$+0.93$, and the maximum normalized mean rectified amplitude is greater than the second boundary 526, i.e., $68 \times$minimum low slope count$+8.16$, the event is determined to be in the VT shock zone, YES in Block 358, and both channels ECG1 and ECG2 are determined to be shockable, Block 357, and the associated buffers are updated accordingly. If either the minimum low slope count is not less than the first boundary 522 or the maximum normalized mean rectified amplitude is not greater than the second boundary 526, the event is determined to be outside the VT shock zone, NO in Block 358, and both channels ECG1 and ECG2 are determined to be not shockable, Block 359.

As described, during both the VF shock zone test, Blocks 360 and 362, and the VT shock zone test, Block 358, the test results for each channel ECG1 and ECG2 as being classified as shockable or not shockable are stored in a rolling buffer containing the most recent eight such designations, for example, for each of the two channels ECG1 and ECG2 that is utilized in the determination of Block 356, as described below.

If only one of the two channels ECG1 and ECG2 is determined to be corrupted by noise, Yes in Block 346, a determination is made whether the signal for the channel not corrupted by noise, i.e., the "clean channel", is more likely associated with a VT event or with a VF event by determining whether the signal for the clean channel includes R-R intervals that are regular and can be therefore classified as being relatively stable, Block 348. If the R-R intervals are determined not to be relatively stable, NO in Block 348, the signal for the clean channel is identified as likely being associated with VF, which is then verified by determining whether the signal for the clean channel is in a VF shock zone, Block 350, described below. If R-R intervals for the clean channel are determined to be stable, YES in Block 348, the signal is identified as likely being associated with VT, which is then verified by determining whether the signal for the clean channel is in a VT shock zone, Block 352.

Figure 18:
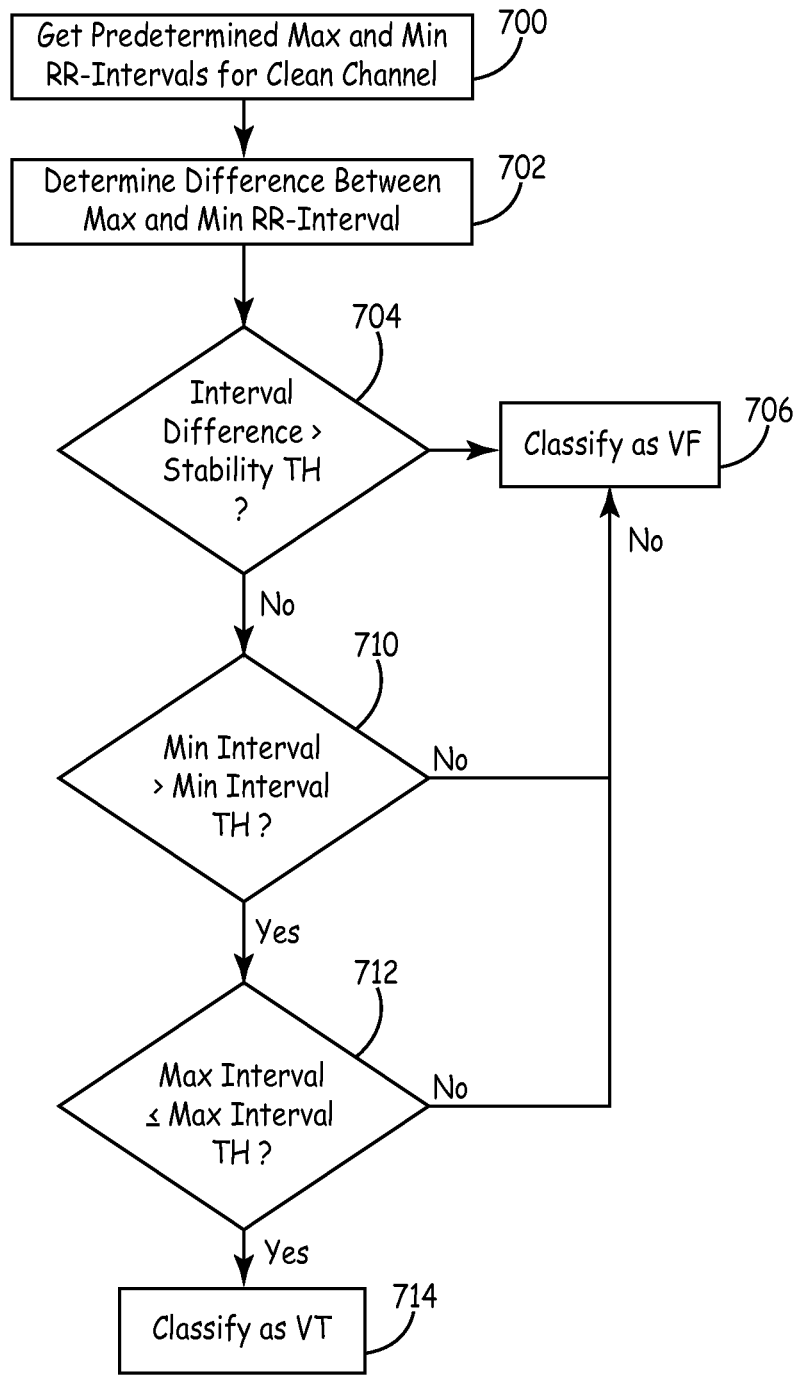
FIG. 18 is a flowchart of a method for discriminating cardiac events according to an embodiment of the disclosure.

According to an embodiment of the present disclosure, in order to determine whether the signal for the clean channel includes R-R intervals that are regular and the clean channel can be therefore classified as being either relatively stable, Yes in Block 348, or relatively unstable, No in Block 348, the device discriminates VT events from VF events in Block 348 by determining whether the relative level of variation in the RR-intervals associated with the clean channel is regular. FIG. 18 is a flowchart of a method for discriminating cardiac events according to an embodiment of the disclosure. For example, as illustrated in FIG. 18, predetermined maximum and minimum intervals for the clean channel are identified from the updated buffer of 12 RR-intervals, Block 342 of FIG. 13. According to an embodiment of the present disclosure, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated to generate an interval difference associated with the clean channel, 702. A determination is then made as to whether the interval difference is greater than a predetermined stability threshold, Block 704, such as 110 milliseconds, for example.

If the interval difference is greater than the stability threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 13, described below. If the interval difference is less than or equal to the stability threshold, No in Block 704, the device determines whether the minimum RR interval is greater than a minimum interval threshold, Block 710, such as 200 milliseconds, for example.

If the minimum interval is less than or equal to the minimum interval threshold, No in Block 710, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 13, described below. If the minimum interval is greater than the minimum interval threshold, Yes in Block 710, the device determines whether the maximum interval is less than or equal to a maximum interval threshold, Block 712, such as 333 milliseconds for example. If the maximum interval is greater than the maximum interval threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 13, described below. If the maximum interval is less than or equal to the maximum interval threshold, the event is classified as a stable event, Block 714, and therefore the clean channel is determined to include regular intervals, Yes in Block 348, and a determination is made as to whether the signal associated with the clean channel is within a predetermined VT shock zone, Block 352 of FIG. 13, described below.

Returning to FIG. 13, the determination of whether the clean channel is within the VF shock zone, Block 350, is made based upon a low slope content metric and a spectral width metric, similar to the VF shock zone determination described above in reference to Blocks 360 and 362, both of which are determined for the clean channel using the method described above. Once the low slope content metric and a spectral width metric are determined for the clean channel, the determination of whether the clean channel is in the VF shock zone is made using Equations 1 and 2, so that if either the low slope content for the clean channel is not less than the first boundary 502 or the spectral width is not less than the second boundary 504, the clean channel is determined not to be in the VF zone, No in Block 350 and both channels are classified as not shockable, Block 351, and the associated buffers are updated accordingly.

If the low slope content for the clean channel is less than the first boundary 502 and the spectral width is less than the second boundary 504, the clean channel is determined to be in the VF zone, Yes in Block 350. A determination is then made as to whether the channel determined to be corrupted by noise, i.e., the "noisy channel", is within the VF shock zone, Block 354. If either the low slope content for the noisy channel is not less than the first boundary 502 or the spectral width is not less than the second boundary 504, the noisy channel is determined not to be in the VF zone, No in Block 354, the clean channel is classified as shockable and the noisy channel is classified as not shockable, Block 355, and the associated buffers are updated accordingly.

If the low slope content for the noisy channel is less than the first boundary 502 and the spectral width is less than the second boundary 504, the noisy channel is determined to be in the VF zone, Yes in Block 354, both the clean channel and the noisy channel are classified as being shockable, Block 353, and the associated buffers are updated accordingly.

Similar to the VT shock zone determination described above in reference to Block 358, during the determination as to whether the clean channel is within the VT shock zone in Block 352, the low slope content and the spectral width is determined for the clean channel as described above in reference to determining the VF shock zone. The first VT shock zone 520 is defined based on the relationship between the low slope content and the spectral width associated with the clean channel according to Equation 3, for example, and the second VT shock zone 524 is defined based on the relationship between the low slope count and the normalized mean rectified amplitude associated with the clean channel. The normalized mean rectified amplitudes for the clean channel is the same as described above in reference to the noise detection tests of Block 344. For example, according to an embodiment of the present disclosure, the second VT shock zone 524 is defined by a second boundary 526 associated with the relationship between the low slope count and the normalized mean rectified amplitude of the clean channel using Equation 4.

If both the low slope count is less than the first boundary 522, i.e., −0.004×spectral width of clean channel+0.93, and the normalized mean rectified amplitude is greater than the second boundary 526, i.e., 68×low slope count of clean channel+8.16, the clean channel is determined to be in the VT shock zone, Yes in Block 352, both channels are classified as being shockable, Block 353, and the associated buffers are updated accordingly.

If either the low slope count is not less than the first boundary 522 or the maximum normalized mean rectified amplitude is not greater than the second boundary 526, the clean channel is determined to be outside the VT shock zone, No in Block 352, both channels are classified as being not shockable, Block 351, and the associated buffers are updated accordingly.

According to an embodiment of the present disclosure, in addition to the classification of the sensing channels ECG1 and ECG2 as being shockable or not shockable using a gross morphology analysis, as described in FIG. 13, for example, the device also performs a beat-based analysis of the beats within each of the three-second windows, Block 368, so that the decision on state transitions (e.g. as to whether to transition from the concerned operating state 104 to the armed operating state 106 in Block 370, or from the armed state 106 to the shock state 108) is made based on the results of both an analysis of the gross morphology of the signal in the three-second window or windows for each sensing channel ECG1 and ECG2, and an analysis of the morphology of individual beats or R-waves in the three-second window or windows for each sensing channel ECG1 and ECG2, as described below. For a three-second segment to be classified as shockable, both the gross morphology and beat-based analysis have to classify the same three-second segment as shockable.

For example, according to an embodiment of the present disclosure, in order to determine whether to transition from the concerned operating state 104 to the armed operating state 106, the device determines whether a predetermined number, such as two out of three for example, of three-second segments for both channels ECG1 and ECG2 have been classified as being shockable during the gross morphology analysis, Blocks 353, 357, 363 and 369, and determines whether those three-second segments for both channels have also been classified as being shockable during the beat-based analysis, Block 368. If the predetermined number of three-second segments in both channels ECG1 and ECG2 have been classified as shockable during both the gross morphology analysis and the beat-based analysis, the device transitions from the concerned state 104 to the armed state 106, Yes in Block 370. When the device determines to transition from the concerned state 104 to the armed state 106, Yes in Block 370, processing continues to be triggered by a three-second time out as is utilized during the concerned state 104, described above.

If the predetermined number of three-second segments in both channels ECG1 and ECG2 have not been classified as shockable during both the gross morphology analysis and the beat-based analysis, the device does not transition from the concerned state 104 to the armed state 106, No in Block 370, and a determination as to whether to transition back to the not concerned state 102 is made, Block 372. The determination as to whether to transition from the concerned state 104 back to the not concerned state 102 is made, for example, by determining whether a heart rate estimate is less than a heart rate threshold level in both of the two channels ECG1 and ECG2, using the method for determining a heart rate estimate as described in U.S. Pat. No. 7,894,894 to Stadler et al., incorporated herein by reference in it's entirety. If it is determined that the device should not transition to the not concerned state 102, i.e., either of the two heart rate estimates are greater than the heart rate threshold, No in Block 372, the process continues using the signal generated during a next three-second window, Block 341.

As described above, the determination of whether the sensing channels ECG1 and ECG2 are shockable or not shockable, Blocks 353, 355, 357, and 363-369, is performed by analyzing the gross morphology of a sensed waveform occurring within the three-second windows. The ECG signal is segmented into n-second intervals, i.e., 3 second intervals, that are used for determining gross morphology features of the three-second waveform. In particular, the gross morphology features are determined across an n-second time interval without relying on R-wave sensing and are therefore features making up the whole waveform signal that can be determined from the ECG signal independent of individual cardiac signals of the cardiac cycle, i.e., individual beats or R-waves contained within the three-second window that are within the entire three-second window. A single waveform in the n-second window begins at the start of the window, extends through entire window, ending at the end of the three-second window so that a single morphology determination is made for the single waveform included within the single three-second window.

On the other hand, multiple cardiac cycles, i.e, R-waves signals, are included within the three-second window, and therefore the n-second window may start and end at any time point relative to each of the individual R-wave signals irrespective of where an individual R-wave signal starts and ends, so that multiple individual beat-based determinations are made for the multiple beat waveforms included within the single three-second window.

Morphology features computed for the single waveform extending across the n-second time period are referred to as "gross" morphology features because the features are characteristics of the single signal, extending from the start to the end of the window, that is extracted, independent of cardiac cycle timing, from a time segment that includes multiple individual cardiac cycles. In contrast, morphology features extracted from the ECG signal during a cardiac cycle are referred to as "beat-based" features. Beat-based features are determined from an ECG signal segment over a time interval of one cardiac cycle of multiple cardiac cycles contained within a single three-second window. Beat-based features may be averaged or determined from multiple cardiac cycles but are representative of a single feature of the ECG signal during a cardiac cycle. Determination of a beat feature is dependent on identifying the timing of a cardiac cycle, or at least a sensed event such as an R-wave, as opposed to determining gross features independent of the cardiac cycle over a time segment that is typically longer than one cardiac cycle.

Figure 19:
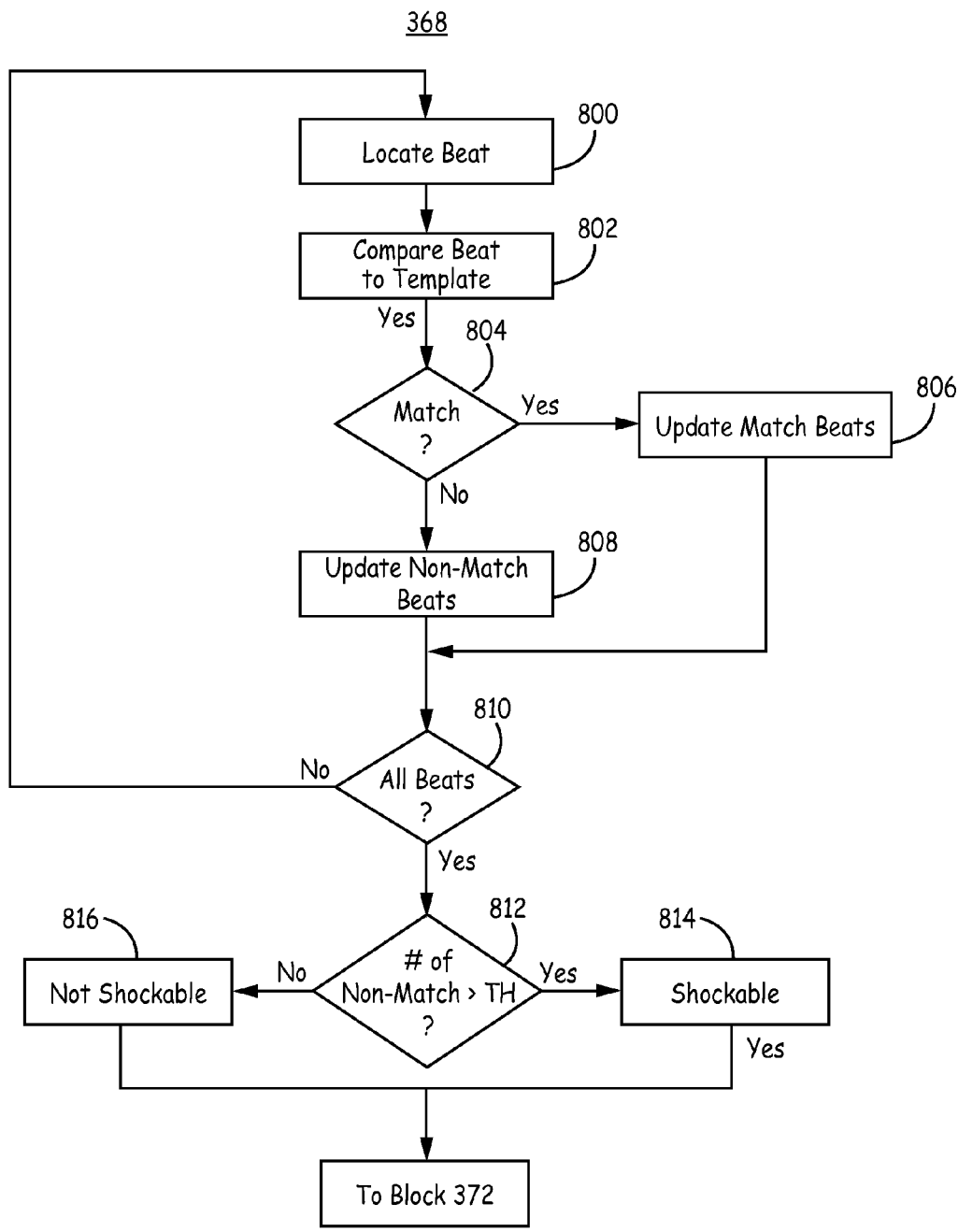
FIG. 19 is a flowchart of a beat-based analysis during detection of arrhythmias in a medical device according to an embodiment of the present disclosure.

FIG. 19 is a flowchart of a beat-based analysis during detection of arrhythmias in a medical device according to an embodiment of the present disclosure. Therefore, as described above, in addition to performing the morphology analysis of the whole waveform within the three-second windows associated with each sensing channel ECG1 and ECG2, the device performs a beat-based analysis of the signal sensed simultaneously within both channels ECG1 and ECG2, Block 368. In particular, as illustrated in FIG. 19, for each three-second sensing window associated with the respective sensing channels ECG1 and ECG2, the device locates a beat, i.e., R-wave, Block 800, and compares the individual beat to a predetermined beat template, Block 802, such as a normal sinus rhythm template, for example. Based upon the comparison of the beat to the template, the device determines whether the beat is either a match beat or a non-match beat by determining the extent to which the beat matches the template, Block 804. For example, in order to identify the beat as either a match beat or a non-match beat, the device determines in Block 804 whether the beat matches the sinus rhythm template within a predetermined percentage, such as 60 percent, for example. If the beat matches the template by the predetermined percentage or greater, Yes in Block 804, the beat is identified as a match beat and the number of match beats for the three-second window is updated, Block 806. If the beat matches the template by less than the predetermined percentage, No in Block 804, the beat is identified as a non-match beat and the number of non-match beats for the three-second window is updated, Block 808.

Once the beat is identified as likely being either a match beat or a non-match beat, the device determines whether the match/non-match determination has been made for all of the beats in the three-second window, Block 810. If the determination has not been made for all of the beats in the three-second window, No in Block 810, the process is repeated with another beat located within the three-second window. Once the determination has been made for all of the beats in the three-second window, Yes in Block 810, a determination is made as to whether the number of non-match beats in the three-second window is greater than a non-match threshold, Block 812. According to an embodiment of the disclosure, the non-match threshold is set as a predetermined percentage, such as 75 percent for example, so that if the number of individual beats in the three-second window that are identified as being non-match beats is greater than 75 percent of the number of all of the beats in the window, Yes in Block 812, the three-second window is identified as being shockable based on beat-based analysis, Block 814. On the other hand, if the number of individual beats in the three-second window that are identified as being non-match beats is not greater than 75 percent of the number of all of the beats in the window, No in Block 812, the three-second window is identified as being not shockable based on beat based analysis, Block 814. The beat-based analysis determination of the three-second windows as being shockable 814 or not shockable, Block 816 is then used in combination with the waveform morphology analysis of both of the three-second windows being shockable, Blocks 353, 357, 363 and 369 or both not shockable, Blocks 351, 355, 359, 365 and 367 to determine whether to transition to the next state, Block 370, as described above.

As can be seen in FIG. 13, the way in which both channels ECG1 and ECG2 could have been determined to be shockable can vary. First, if noise was not determined to be occurring in either channel, No in Block 346, but both channels are determined to have regular intervals, Yes in Block 356, and both channels are determined to be in the VT shock zone, Yes in Block 358, both of the sensing channels ECG1 and ECG2 are determined to be shockable, Block 359. Second, if noise was not determined to be occurring in either channel, No in Block 346, but both channels are not determined to have regular intervals, No in Block 356, and both channels are determined to be in the VF shock zone, Yes in Blocks 360 and 362, both of the sensing channels ECG1 and ECG2 are determined to be shockable.

However, if noise was determined to be occurring in one channel, Yes in Block 346, but the clean channel was determined to have regular intervals, Yes in Block 348, and to be in the VT shock zone, Yes in Block 352, both of the sensing channels ECG1 and ECG2 are determined to be shockable, Block 353. Finally, if noise was determined to be occurring in one channel, Yes in Block 346, the clean channel was determined not to have regular intervals, No in Block 348, and both the clean and the noisy channel are determined to be in the VF shock zone, Yes in Blocks 350 and 354, both of the sensing channels ECG1 and ECG2 are determined to be shockable, Block 353.

In this way, both channels may be determined to be shockable based on a determination that both channels are either in the VF shock zone, Blocks 363 and 369, or Block 353 via Blocks 350 and 354, based on a determination that both channels are in the VT shock zone, Block 357, or based on a determination that only one channel, i.e., the clean channel, is within the VT shock zone, Block 353 via Block 352.

Figure 20:
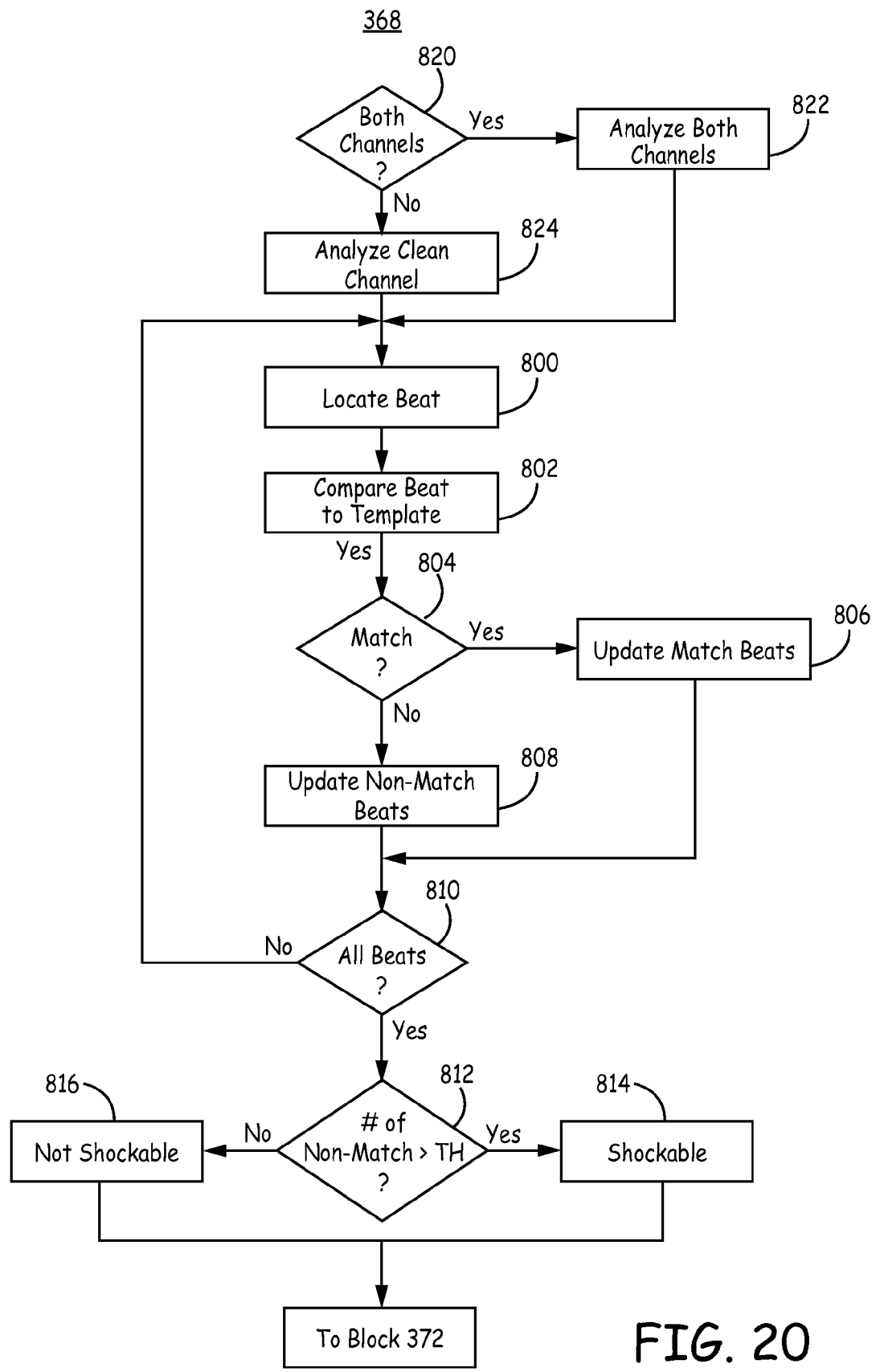
FIG. 20 is a flowchart of a beat-based analysis during detection of arrhythmias in a medical device according to an embodiment of the present disclosure.

FIG. 20 is a flowchart of a beat-based analysis during detection of arrhythmias in a medical device according to an embodiment of the present disclosure. Therefore, according to an embodiment of the present disclosure, the device may initially identify how the three-second windows were determined to be shockable during the gross morphology analysis, i.e., by using both channels or only one channel, and based on this determination, determine which channels that are to be utilized in the beat morphology analysis.

Therefore, as illustrated in FIGS. 13 and 20, according to one embodiment, the device determines whether both channels were used in the identification of both channels being shockable, Block 820, so that if both channels were utilized, Yes in Block 820, the beat-based analysis, Block 368, is performed for both channels, Block 822, as described above in FIG. 19.

If both channels were not utilized, No in Block 820, the beat-based analysis, Block 368, is performed for only one channel, i.e., the clean channel, Block 824. In particular, the device locates a beat, i.e., R-wave, in only the clean channel, Block 800, and compares the individual beat to a predetermined beat template, Block 802, such as a normal sinus rhythm template, for example. Based upon the comparison of the beat to the template, the device determines whether the beat is either a match beat or a non-match beat by determining the extent to which the beat matches the template, Block 804. For example, in order to identify the beat as either a match beat or a non-match beat, the device determines in Block 804 whether the beat matches the sinus rhythm template within a predetermined percentage, such as 60 percent, for example. If the beat matches the template by the predetermined percentage or greater, Yes in Block 804, the beat is identified as a match beat and the number of match beats for the three-second window is updated, Block 806. If the beat matches the template by less than the predetermined percentage, No in Block 804, the beat is identified as a non-match beat and the number of non-match beats for the three-second window is updated, Block 808.

Once the beat is identified as likely being either a match beat or a non-match beat, the device determines whether the match/non-match determination has been made for all of the beats in the three-second window of only the clean channel, Block 810. If the determination has not been made for all of the beats in the three-second window for the clean channel, No in Block 810, the process is repeated with another beat located within the three-second window of the clean channel. Once the determination has been made for all of the beats in the three-second window of the clean channel, Yes in Block 810, a determination is made as to whether the number of non-match beats in the three-second window is greater than a non-match threshold, Block 812. According to an embodiment of the disclosure, the non-match threshold is set as a predetermined percentage, such as 75 percent for example, so that if the number of individual beats in the three-second window that are identified as being non-match beats is greater than 75 percent of the number of all of the beats in the window, Yes in Block 812, the three-second window of the clean channel is identified as being shockable based on the beat-based analysis, Block 814. On the other hand, if the number of individual beats in the three-second window that are identified as being non-match beats is not greater than 75 percent of all of the number of the beats in the window, No in Block 812, the three-second window of the clean channel is identified as being not shockable based on the beat-based analysis, Block 814.

The decision as to whether to transition from the concerned operating state 104 to the armed operating state 106 in Block 370 is made based on the results of both an analysis of the morphology of the signal in the three-second window or windows for each sensing channel ECG1 and ECG2, and an analysis of morphology of individual beats or R-waves in the three-second window or windows for each sensing channel ECG1 and ECG2, as described above. In the instance where the beat-based analysis was performed for only one channel, i.e., the clean channel, Block 824, the determination of whether to transition to the next state, Block 370, would be satisfied if both the predetermined number of three-second segments in both channels ECG1 and ECG2 have been classified as shockable during the gross morphology analysis, and the beat-based analysis, Block 368, is satisfied for only the clean channel, and therefore the device transitions from the concerned state 104 to the armed state 106, Yes in Block 370. If the predetermined number of three-second segments in both channels ECG1 and ECG2 have not been classified as shockable during both the gross morphology analysis and the beat-based analysis of only the clean channel, the device does not transition from the concerned state 104 to the armed state 106, No in Block 370, and a determination as to whether to transition back to the not concerned state 102 is made, Block 372, as described above.

Various examples have been described. These and other examples are within the scope of the following claims.

The invention claimed is:

1. A method comprising:
 obtaining, with a sensing module of a medical device, cardiac electrical signals;
 processing, with a control module of the medical device, the cardiac electrical signals from the sensing module in accordance with a tachyarrhythmia detection algorithm to monitor for a tachyarrhythmia;
 detecting, with the control module of the medical device, initiation of a pacing train delivered by a second implantable medical device;
 determining, with the control module of the medical device, a type of the detected pacing train, wherein determining the type of detected pacing train comprises:
  computing at least two cycle lengths using at least three most recently detected pacing spikes,
  estimating a cycle length of the pacing train based on the at least two computed cycle lengths,
  comparing the estimated cycle length of the pacing train to at least one cycle length threshold, and
  determining the type of the detected pacing train based on the comparison;
 modifying, with the control module of the medical device, a tachyarrhythmia detection algorithm based on the type of the detected pacing train; and
 delivering, with a therapy module of the medical device, a shock therapy based on the tachyarrhythmia detection algorithm.

2. The method of claim 1, wherein determining a type of the detected pacing train comprises analyzing one or more of an onset of the heart rate immediately prior to the detected pacing train, a regularity of the pacing pulse intervals, a consistency of the pacing artifact amplitude, a consistency of the pacing pulse slew rate, and/or a consistency of the pacing pulse polarity.

3. The method of claim 1, further comprising:
obtaining an electrical signal sensed on an implantable electrical lead coupled to the IMD; and
analyzing at least one of an amplitude and a slew rate of the electrical signal to detect pacing pulses in the electrical signal, wherein detecting initiation of the pacing train comprises detecting initiation of the pacing train using the detected pacing pulses.

4. The method of claim 1, further comprising implementing a tachyarrhythmia detection algorithm having one or more stages, wherein at least one of the stages analyzes a morphology of a plurality of predetermined segments of the sensed electrical signal and further wherein modifying the tachyarrhythmia detection algorithm comprises holding the morphology analysis in a current state in response to detecting the type of the pacing train to be anti-tachycardia pacing (ATP).

5. The method of claim 4, further comprising:
detecting termination of the pacing train; and
resuming the morphology analysis of the tachyarrhythmia detection algorithm in response to detecting the termination of the pacing train.

6. The method of claim 5, wherein detecting termination of the pacing train comprises detecting termination of the pacing train when no pacing spikes have been detected for a threshold period of time.

7. The method of claim 6, wherein detecting termination of the pacing train when no pacing spikes have been detected for a threshold period of time comprises detecting termination of the pacing train when no pacing spikes have been detected for at least two times an estimated cycle length of the pacing train.

8. The method of claim 5, wherein detecting termination of the pacing train comprises detecting termination of the pacing train when the amount of time since detecting the initiation of the pacing train exceeds a threshold amount of time.

9. The method of claim 1, wherein detecting initiation of the pacing train by analyzing the sensed electrical signals on the implantable electrical lead comprises detecting initiation of the pacing train pulses when two pacing pulses are detected within a threshold period of time.

10. The method of claim 9, wherein detecting initiation of the pacing train when two pacing pulses are detected within a threshold period of time comprises detecting initiation of the pacing train when two pacing pulses are detected within 1500 milliseconds of one another.

11. The method of claim 1, wherein estimating the cycle length of the pacing train based on the at least two most recently computed cycle lengths comprises estimating the cycle length of the pacing train as a shortest of the two most recent computed cycle lengths.

12. The method of claim 1, further comprising:
implementing a tachyarrhythmia detection algorithm that analyzes segments of the electrical signals of a predetermined length and classifies each segment as shockable or non-shockable;
wherein determining a type of the detected pacing train comprises determining the pacing train to be a fast bradycardia pacing train and modifying to the tachyarrhythmia detection algorithm comprises:
comparing a morphology of a first sensed event within one of the segments with a morphology of a predetermined number of subsequent sensed events within the segments; and
classifying the rhythm as shockable or non-shockable based on at least the number of subsequent sensed events having a morphology that matches the morphology of the first sensed event of the tachyarrhythmia.

13. The method of claim 12, wherein classifying the rhythm as shockable or non-shockable based on at least the number of subsequent sensed events having a morphology that matches the morphology of the first sensed event of the tachyarrhythmia comprises classifying the tachyarrhythmia as non-shockable when the number of subsequent sensed events having a morphology that matches the morphology of the first sensed event of the tachyarrhythmia is greater than or equal to a lower threshold and less than or equal to an upper threshold.

14. A medical device comprising:
a sensing module configured to obtain cardiac electrical signals;
a control module configured to process the cardiac electrical signals from the sensing module in accordance with a tachyarrhythmia detection algorithm to monitor for a tachyarrhythmia, detect initiation of a pacing train delivered by a second implantable medical device, computes at least two cycle lengths using at least three most recently detected pacing spikes, estimates a cycle length of the pacing train based on the at least two computed cycle lengths, compares the estimated cycle length of the pacing train to at least one cycle length threshold, determine a type of the detected pacing train based on the comparison, and modify the tachyarrhythmia detection algorithm based on the type of the detected pacing train; and
a therapy module configured to deliver a shock therapy based on the tachyarrhythmia detection algorithm.

15. The device of claim 14, wherein the control module determines the type of the detected pacing train by analyzing one or more of an onset of a heart rate immediately prior to the detected pacing train, a regularity of pacing pulse intervals, a consistency of a pacing artifact amplitude, a consistency of a pacing pulse slew rate, and/or a consistency of a pacing pulse polarity.

16. The device of claim 14, wherein the control module analyzes at least one of an amplitude and a slew rate of the cardiac electrical signals to detect pacing pulses in the cardiac electrical signals and detects initiation of the pacing train using the detected pacing pulses.

17. The device of claim 14, wherein the tachyarrhythmia detection algorithm includes at least one stage in which the control module analyzes a morphology of a plurality of predetermined segments of the sensed cardiac electrical signal and the control module modifies the tachyarrhythmia detection algorithm by holding the morphology analysis in a current state in response to detecting the type of the pacing train to be anti-tachycardia pacing (ATP).

18. The device of claim 17, wherein the control module detects termination of the pacing train and resumes the morphology analysis of the tachyarrhythmia detection algorithm in response to detecting the termination of the pacing train.

19. The device of claim 18, wherein the control module detects termination of the pacing train when no pacing spikes have been detected for a threshold period of time.

20. The device of claim 19, wherein the threshold period of time is at least two times an estimated cycle length of the pacing train.

21. The device of claim 18, wherein the control module detects termination of the pacing train when the amount of time since detecting the initiation of the pacing train exceeds a threshold amount of time.

22. The device of claim 14, wherein the control module detects initiation of the pacing train pulses when two pacing pulses are detected within a threshold period of time.

23. The device of claim 22, wherein the threshold period of time is 1500 milliseconds.

24. The device of claim 14, wherein the control module estimates the cycle length as a shortest of the at least two computed cycle lengths.

25. The device of claim 14, wherein:
the tachyarrhythmia detection algorithm analyzes segments of the cardiac electrical signals of a predetermined length and classifies each segment as shockable or non-shockable and
the control module determines a type of the detected pacing train to be a fast bradycardia pacing train and modifies to the tachyarrhythmia detection algorithm by comparing a morphology of a first sensed event within one of the segments with a morphology of a predetermined number of subsequent sensed events within the segments and classifying the rhythm as shockable or non-shockable based on at least the number of subsequent sensed events having a morphology that matches the morphology of the first sensed event of the tachyarrhythmia.

26. The device of claim 25, wherein the control module classifies the rhythm as non-shockable when the number of subsequent sensed events having a morphology that matches the morphology of the first sensed event of the tachyarrhythmia is greater than or equal to a lower threshold and less than or equal to an upper threshold.

27. A system comprising:
an implantable cardiac pacemaker device; and
an extravascular implantable cardioverter-defibrillator (ICD) system that includes:
at least one lead comprising one or more electrodes; and
an ICD device electrically connected to the at least one lead, the ICD device comprising:
a sensing module configured to obtain cardiac electrical signals; and
a control module configured to process the cardiac electrical signals from the sensing module in accordance with a tachyarrhythmia detection algorithm to monitor for a tachyarrhythmia, wherein the control module is further configured to detect initiation of a pacing train delivered by the implantable cardiac pacemaker device, determine a type of the detected pacing train, and modify the tachyarrhythmia detection algorithm based on the type of the detected pacing train; and
wherein the control module detects the type of pacing train to be an anti-tachycardia pacing (ATP) train and the modification of the tachyarrhythmia detection algorithm results in a delay of a shock; and
a therapy module configured to deliver the shock after the delay.

28. The system of claim 27, wherein the modification of the tachyarrhythmia detection algorithm results in the delay of the shock for up to 10 seconds.

29. A medical device comprising:
a sensing module configured to obtain cardiac electrical signals; and
a control module configured to process the cardiac electrical signals from the sensing module in accordance with a tachyarrhythmia detection algorithm to monitor for a tachyarrhythmia, detect initiation of a pacing train delivered by a second implantable medical device, determine a type of the detected pacing train, and modify the tachyarrhythmia detection algorithm based on the type of the detected pacing train,
wherein the tachyarrhythmia detection algorithm includes at least one stage in which the control module analyzes a morphology of a plurality of predetermined segments of the sensed cardiac electrical signal and the control module modifies the tachyarrhythmia detection algorithm by holding the morphology analysis in a current state in response to detecting the type of the pacing train to be anti-tachycardia pacing (ATP); and
a therapy module configured to deliver a shock therapy based on the tachyarrhythmia detection algorithm.

30. The device of claim 29, wherein the control module detects termination of the pacing train and resumes the morphology analysis of the tachyarrhythmia detection algorithm in response to detecting the termination of the pacing train.

31. The device of claim 30, wherein the control module detects termination of the pacing train when no pacing spikes have been detected for a threshold period of time.

32. The device of claim 31, wherein the threshold period of time is at least two times an estimated cycle length of the pacing train.

33. The device of claim 30, wherein the control module detects termination of the pacing train when the amount of time since detecting the initiation of the pacing train exceeds a threshold amount of time.

34. A medical device comprising:
a sensing module configured to obtain cardiac electrical signals; and
a control module configured to process the cardiac electrical signals from the sensing module in accordance with a tachyarrhythmia detection algorithm to monitor for a tachyarrhythmia, detect initiation of a pacing train delivered by a second implantable medical device, determine a type of the detected pacing train, and modify the tachyarrhythmia detection algorithm based on the type of the detected pacing train,
wherein the tachyarrhythmia detection algorithm analyzes segments of the cardiac electrical signals of a predetermined length and classifies each segment as shockable or non-shockable and
wherein the control module determines a type of the detected pacing train to be a fast bradycardia pacing train and modifies to the tachyarrhythmia detection algorithm by comparing a morphology of a first sensed event within one of the segments with a morphology of a predetermined number of subsequent sensed events within the segments and classifying the rhythm as shockable or non-shockable based on at least the number of subsequent sensed events having a morphology that matches the morphology of the first sensed event of the tachyarrhythmia; and
a therapy module configured to deliver a shock therapy based on the tachyarrhythmia detection algorithm.

35. The device of claim 34, wherein the control module classifies the rhythm as non-shockable when the number of subsequent sensed events having a morphology that matches the morphology of the first sensed event of the tachyarrhythmia is greater than or equal to a lower threshold and less than or equal to an upper threshold.

36. A medical device comprising:
a sensing module configured to obtain cardiac electrical signals; and
a control module configured to process the cardiac electrical signals from the sensing module in accordance with a tachyarrhythmia detection algorithm to monitor for a tachyarrhythmia, detect initiation of a pacing train delivered by a second implantable medical device, determine a type of the detected pacing train, and modify the tachyarrhythmia detection algorithm based on the type of the detected pacing train, wherein the tachyarrhythmia detection algorithm includes a plurality of stages comprising at least a first stage and a second stage,
wherein the control module is configured to modify the tachyarrhythmia detection algorithm by modifying a tachyarrhythmia detection analysis of the second stage; and
a therapy module configured to deliver a shock therapy based on the tachyarrhythmia detection algorithm.

37. The device of claim 36, wherein the control module is configured to analyze a morphology of a plurality of segments of the sensed cardiac electrical signal in the second stage and modify the tachyarrhythmia detection algorithm by modifying the morphology analysis.

38. A medical device comprising:
a sensing module configured to obtain cardiac electrical signals; and
a control module configured to process the cardiac electrical signals from the sensing module in accordance with a tachyarrhythmia detection algorithm to monitor for a tachyarrhythmia, detect initiation of a pacing train delivered by a second implantable medical device, determine a type of the detected pacing train, and modify the tachyarrhythmia detection algorithm based on the type of the detected pacing train,
wherein the control module is configured to determine the type of the detected pacing train by at least analyzing an onset of the heart rate immediately prior to the detected pacing train; and
a therapy module configured to deliver a shock therapy based on the tachyarrhythmia detection algorithm.

* * * * *